United States Patent
Nelson et al.

(10) Patent No.: US 10,214,760 B2
(45) Date of Patent: Feb. 26, 2019

(54) METHODS FOR AMPLIFYING NUCLEIC ACID USING TAG-MEDIATED DISPLACEMENT

(71) Applicant: Gen-Probe Incorporated, San Diego, CA (US)

(72) Inventors: Norman C. Nelson, San Diego, CA (US); Margarita Batranina-Kaminsky, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 326 days.

(21) Appl. No.: 14/928,796

(22) Filed: Oct. 30, 2015

(65) Prior Publication Data

US 2016/0222426 A1    Aug. 4, 2016

Related U.S. Application Data

(63) Continuation of application No. 14/344,372, filed as application No. PCT/US2012/056666 on Sep. 21, 2012, now Pat. No. 9,175,337.

(Continued)

(51) Int. Cl.
*C12Q 1/68* (2018.01)
*C12P 19/34* (2006.01)
(Continued)

(52) U.S. Cl.
CPC ............ *C12P 19/34* (2013.01); *C12Q 1/6855* (2013.01); *C12Q 1/6844* (2013.01); *C12Q 2537/137* (2013.01)

(58) Field of Classification Search
CPC . C12P 19/34; C12Q 1/6855; C12Q 2537/137; C12Q 1/6844
See application file for complete search history.

(56) References Cited

U.S. PATENT DOCUMENTS 5,470,724 A    11/1995    Ahern
5,714,320 A    2/1998     Kool
(Continued)

FOREIGN PATENT DOCUMENTS

EP    1061135 A2    12/2000
WO    WO 95/003430 A1    2/1995
(Continued)

OTHER PUBLICATIONS

Examination Report, European Application No. 12 772 175.1-1404, dated Feb. 5, 2015.
(Continued)

*Primary Examiner* — Teresa E Strzelecka
(74) *Attorney, Agent, or Firm* — Jeff Landes; Alston & Bird LLP

(57) ABSTRACT

Disclosed are methods for amplifying a nucleic acid target region using an amplification oligomer comprising a target-binding segment and a heterologous displacer tag situated 5' to the target-binding segment. Initiation of an amplification reaction from the tagged amplification oligomer produces an amplicon comprising the displacer tag, such that once the complement of the displacer tag has been incorporated into a second amplicon, a displacer oligonucleotide having a sequence substantially corresponding to the displacer tag sequence is used to participate in subsequent rounds of amplification for displacement of an extension product primed from a site within the second amplicon 5' to the displacer priming site. Also disclosed are related kits and reaction mixtures comprising the displacer-tagged amplification oligomer and corresponding displacer oligonucleotide.

25 Claims, 13 Drawing Sheets

Specification includes a Sequence Listing.

Related U.S. Application Data

(60) Provisional application No. 61/537,452, filed on Sep. 21, 2011.

(51) Int. Cl.
    *C12Q 1/6855*     (2018.01)
    *C07H 21/04*     (2006.01)
    *C12Q 1/6844*     (2018.01)

(56) References Cited

U.S. PATENT DOCUMENTS

| | | |
|---|---|---|
| 5,744,311 A | 4/1998 | Fraiser |
| 7,198,897 B2 | 4/2007 | Wangh et al. |
| 9,175,337 B2 | 11/2015 | Nelson et al. |
| 2009/0286249 A1 | 11/2009 | Becker et al. |
| 2011/0171652 A1 | 7/2011 | You |

FOREIGN PATENT DOCUMENTS

| | | |
|---|---|---|
| WO | WO 97/004126 A1 | 2/1997 |
| WO | WO 13/044097 A1 | 3/2013 |

OTHER PUBLICATIONS

Patent Examination Report, Autstralian Patent Application No. 2012312169, dated Dec. 11, 2014.

U.S. Appl. No. 14/344,372, Non-Final Office Action dated Jan. 15, 2015.

U.S. Appl. No. 14/344,372, Notice of Allowance dated Jun. 23, 2015.

WIPO Application No. PCT/US2012/056666, PCT International Preliminary Report on Patentability dated Mar. 25, 2014.

WIPO Application No. PCT/US2012/056666, PCT International Search Report dated Feb. 22, 2013.

WIPO Application No. PCT/US2012/056666, PCT Written Opinion of the International Searching Authority dated Feb. 22, 2013.

| D4 | S4 | T2 |                                                   AO2

| D4 | S4 | T2 |      TNA      | cT1 | cS1 | cD1 |       AP2

1   | cD4 | cS4 | cT2 |      tna      | T1 | S1 | D1p |   AP4
    | D4p || T2p |
          (POL)

EXTENSION AND DISPLACEMENT

2   | cD4 | cS4 | cT2 |      tna      | T1 | S1 | D1p |   AP4

| cD4p | S4 | T2 |      TNA      | cT1 | cS1 | cD1p |  AP15

| T2 |      TNA      | cT1 | cS1 | cD1p |  AP14

```
                         SEQUENCE LISTING

<160> NUMBER OF SEQ ID NOS: 12

<210> SEQ ID NO 1
<211> LENGTH: 59
<212> TYPE: DNA
<213> ORGANISM: Artificial Sequence
<220> FEATURE:
<223> OTHER INFORMATION: Synthetic Target Capture Oligomer
<220> FEATURE:
<221> NAME/KEY: misc_feature
<222> LOCATION: (27)..(59)

<400> SEQUENCE: 1
cgaacuugcg cacacacguc auuggattta aaaaaaaaaa aaaaaaaaa aaaaaaaa        59

<210> SEQ ID NO 2
<211> LENGTH: 24
<212> TYPE: DNA
<213> ORGANISM: Artificial Sequence
<220> FEATURE:
<223> OTHER INFORMATION: Synthetic Oligomer - Torch

<400> SEQUENCE: 2
ugugucuuca ggaugaaaca caca                                            24

<210> SEQ ID NO 3
```

```
<211> LENGTH: 23
<212> TYPE: DNA
<213> ORGANISM: Artificial Sequence
<220> FEATURE:
<223> OTHER INFORMATION: Synthetic Oligomer - Blocker

<400> SEQUENCE: 3
gaugcagugg gcagcuguga gga                                                 23

<210> SEQ ID NO 4
<211> LENGTH: 39
<212> TYPE: DNA
<213> ORGANISM: Artificial Sequence
<220> FEATURE:
<223> OTHER INFORMATION: Synthetic Promoter-Based Amplification Oligomer
<220> FEATURE:
<221> NAME/KEY: promoter
<222> LOCATION: (1)..(27)

<400> SEQUENCE: 4
aatttaatac gactcactat agggagacca caacggttt                                39

<210> SEQ ID NO 5
<211> LENGTH: 20
<212> TYPE: DNA
<213> ORGANISM: Artificial Sequence
<220> FEATURE:
<223> OTHER INFORMATION: Synthetic Amplification Oligomer

<400> SEQUENCE: 5
gaggtcgtgg ctggagtcat                                                     20

<210> SEQ ID NO 6
<211> LENGTH: 72
<212> TYPE: DNA
<213> ORGANISM: Artificial Sequence
<220> FEATURE:
<223> OTHER INFORMATION: Synthetic Amplification Oligomer
<220> FEATURE:
<221> NAME/KEY: misc_feature
<222> LOCATION: (1)..(20)
<223> OTHER INFORMATION: Displacer Tag
<220> FEATURE:
<221> NAME/KEY: misc_feature
<222> LOCATION: (21)..(30)
<223> OTHER INFORMATION: Spacer
<220> FEATURE:
<221> NAME/KEY: misc_feature
<222> LOCATION: (31)..(50)
<223> OTHER INFORMATION: S-Oligo hybridizing region

<400> SEQUENCE: 6
gaggtcgtgg ctggagtcat atgtcaacgt gtcatatgcg acgatctcag gctgtggctg         60
acctgaaata cc                                                             72

<210> SEQ ID NO 7
<211> LENGTH: 72
<212> TYPE: DNA
<213> ORGANISM: Artificial Sequence
<220> FEATURE:
<223> OTHER INFORMATION: Synthetic Amplification Oligomer
<220> FEATURE:
<221> NAME/KEY: misc_feature
<222> LOCATION: (1)..(20)
<223> OTHER INFORMATION: S-Oligo hybridizing region
<220> FEATURE:
<221> NAME/KEY: misc_feature
<222> LOCATION: (21)..(30)
<223> OTHER INFORMATION: spacer
<220> FEATURE:
```

```
<221> NAME/KEY: misc_feature
<222> LOCATION: (31)..(50)
<223> OTHER INFORMATION: S-Oligo hybridizing region

<400> SEQUENCE: 7
gtcatatgcg acgatctcag atgtcaacgt gtcatatgcg acgatctcag gctgtggctg        60
acctgaaata cc                                                            72

<210> SEQ ID NO 8
<211> LENGTH: 62
<212> TYPE: DNA
<213> ORGANISM: Artificial Sequence
<220> FEATURE:
<223> OTHER INFORMATION: Synthetic Amplification Oligomer
<220> FEATURE:
<221> NAME/KEY: misc_feature
<222> LOCATION: (1)..(20)
<223> OTHER INFORMATION: Displacer Tag
<220> FEATURE:
<221> NAME/KEY: misc_feature
<222> LOCATION: (21)..(40)
<223> OTHER INFORMATION: S-Oligo hybridizing region

<400> SEQUENCE: 8
gaggtcgtgg ctggagtcat gtcatatgcg acgatctcag gctgtggctg acctgaaata        60
cc                                                                       62

<210> SEQ ID NO 9
<211> LENGTH: 42
<212> TYPE: DNA
<213> ORGANISM: Artificial Sequence
<220> FEATURE:
<223> OTHER INFORMATION: Synthetic Amplification Oligomer
<220> FEATURE:
<221> NAME/KEY: misc_feature
<222> LOCATION: (1)..(20)
<223> OTHER INFORMATION: S-Oligo hybridizing region

<400> SEQUENCE: 9
gtcatatgcg acgatctcag gctgtggctg acctgaaata cc                           42

<210> SEQ ID NO 10
<211> LENGTH: 20
<212> TYPE: DNA
<213> ORGANISM: Artificial Sequence
<220> FEATURE:
<223> OTHER INFORMATION: Synthetic Amplification Oligomer

<400> SEQUENCE: 10
gtcatatgcg acgatctcag                                                    20

<210> SEQ ID NO 11
<211> LENGTH: 61
<212> TYPE: DNA
<213> ORGANISM: Artificial Sequence
<220> FEATURE:
<223> OTHER INFORMATION: Synthetic Promoter-Based Amplification Oligomer
<220> FEATURE:
<221> NAME/KEY: promoter
<222> LOCATION: (1)..(27)
<220> FEATURE:
<221> NAME/KEY: misc_feature
<222> LOCATION: (28)..(39)
<223> OTHER INFORMATION: S-Oligo Hybridizing Region

<400> SEQUENCE: 11
aatttaatac gactcactat agggagacca caacggttta cccagcaaga tcacgctttt        60
```

-continued

```
<210> SEQ ID NO 12
<211> LENGTH: 42
<212> TYPE: DNA
<213> ORGANISM: Artificial Sequence
<220> FEATURE:
<223> OTHER INFORMATION: Synthetic S-Oligomer
<220> FEATURE:
<221> NAME/KEY: misc_feature
<222> LOCATION: (1)..(12)
<223> OTHER INFORMATION: T7 hybridizing region
<220> FEATURE:
<221> NAME/KEY: misc_feature
<222> LOCATION: (23)..(42)
<223> OTHER INFORMATION: Non-T7 hybridizing region

<400> SEQUENCE: 12
aaaccgttgt ggtctccta tactgagatc gtcgcatatg ac                           42
```

METHODS FOR AMPLIFYING NUCLEIC ACID USING TAG-MEDIATED DISPLACEMENT

CROSS-REFERENCE TO RELATED APPLICATIONS

This application is a continuation of U.S. application Ser. No. 14/344,372, filed Mar. 12, 2014, now U.S. Pat. No. 9,175,337, which is a National Stage Entry of International Application No. PCT/US2012/056666, filed Sep. 21, 2012, and which claims the benefit under 35 U.S.C. § 119(e) of U.S. Provisional Application No. 61/537,452, filed Sep. 21, 2011; the contents of which are incorporated herein by reference.

BACKGROUND OF THE INVENTION

Field of the Invention

The present invention resides in the technical fields of molecular biology and diagnostics and relates in particular to amplification of nucleic acids.

Background Art

The detection and/or quantitation of specific nucleic acid sequences is an important technique for identifying and classifying microorganisms, diagnosing infectious diseases, measuring response to various types of treatment, and the like. Such procedures are also useful in detecting and quantitating microorganisms in foodstuffs, water, beverages, industrial and environmental samples, seed stocks, and other types of material where the presence of specific microorganisms may need to be monitored.

Numerous amplification-based methods for the detection and quantitation of target nucleic acids are well-known and established in the art. The polymerase chain reaction, commonly referred to as PCR, uses multiple cycles of denaturation, annealing of primer pairs to opposite strands, and primer extension to exponentially increase copy numbers of the target sequence. (See, e.g., U.S. Pat. Nos. 4,683,195, 4,683,202, and 4,800,159 to Mullis et al.; U.S. Pat. No. 5,804,375 to Gelfand et al.; Mullis et al., *Meth. Enzymol.* 155:335-350, 1987; and Murakawa et al., *DNA* 7:287-295, 1988).

In a variation called RT-PCR, reverse transcriptase (RT) is used to make a complementary DNA (cDNA) from RNA, and the cDNA is then amplified by PCR to produce multiple copies of DNA. (See, e.g., U.S. Pat. Nos. 5,322,770 and 5,310,652 to Gelfand et al.)

Another well-known amplification method is strand displacement amplification, commonly referred to as SDA, which uses cycles of annealing pairs of primer sequences to opposite strands of a target sequence, primer extension in the presence of a dNTP to produce a duplex hemiphosphorothioated primer extension product, endonuclease-mediated nicking of a hemimodified restriction endonuclease recognition site, and polymerase-mediated primer extension from the 3'-end of the nick to displace an existing strand and produce a strand for the next round of primer annealing, nicking and strand displacement, resulting in geometric amplification of product. (See, e.g., Walker et al., *Proc. Natl. Acad. Sci. USA* 89:392-396, 1992; U.S. Pat. Nos. 5,270,184 and 5,455,166 to Walker et al.; Walker et al., *Nucleic Acids Research* 20, 1691-1696, 1992). Thermophilic SDA (tSDA) uses thermophilic endonucleases and polymerases at higher temperatures in essentially the same method. (See, e.g., European Pat. No. 0 684 315.)

Other amplification methods include rolling circle amplification (RCA) (see, e.g., U.S. Pat. No. 5,854,033 to Lizardi); helicase dependent amplification (HDA) (see, e.g., Kong et al., U.S. Pat. Appln. Pub. No. US 2004-0058378 A1); and loop-mediated isothermal amplification (LAMP) (see, e.g., U.S. Pat. No. 6,410,278 to Notomi et al.).

Transcription-based amplification methods commonly used in the art include nucleic acid sequence based amplification, also referred to as NASBA (see, e.g., U.S. Pat. No. 5,130,238 to Malek et al.); methods which rely on the use of an RNA replicase to amplify the probe molecule itself, commonly referred to as Qβ replicase (see, e.g., Lizardi et al., *BioTechnol.* 6:1197-1202, 1988); transcription-based amplification methods (see, e.g., Kwoh et al., *Proc. Natl. Acad. Sci. USA* 86:1173-1177, 1989) and self-sustained sequence replication (see, e.g., Guatelli et al., *Proc. Natl. Acad. Sci. USA* 87:1874-1878, 1990; Landgren, *Trends in Genetics* 9:199-202, 1993; and HELEN H. LEE et al., *Nucleic Acid Amplification Technologies* (1997)).

Another transcription-based amplification method is transcription-mediated amplification, commonly referred to as TMA, which synthesizes multiple copies of a target nucleic acid sequence autocatalytically under conditions of substantially constant temperature, ionic strength, and pH, in which multiple RNA copies of the target sequence autocatalytically generate additional copies (see, e.g., U.S. Pat. Nos. 5,480,784 and 5,399,491 to Kacian et al.). TMA is a robust and highly sensitive amplification system with demonstrated efficacy, which overcomes many of the problems associated with PCR-based amplification systems. In particular, temperature cycling is not required.

SUMMARY OF THE INVENTION

In one aspect, the present invention provides a method for amplifying nucleic acid target region. The method generally includes using amplification oligonucleotide equipped with a heterologous displacer tag situated 5' to a target-binding segment and having a sequence that substantially corresponds to the priming sequence of a displacer oligonucleotide. Initiation of an amplification reaction from the tagged amplification oligomer produces an amplicon comprising the displacer tag. Once the complement of the displacer tag has been incorporated into a second amplicon, thereby providing a displacer priming site, the displacer oligonucleotide participates in a subsequent round of amplification for displacement of an extension product primed from a site within the second amplicon 5' to the displacer priming site.

In some embodiments, the method of amplifying a nucleic acid target region uses a first forward amplification oligomer comprising (a) a target-binding priming segment (T1) substantially complementary to a 3'-end of the target region, (b) a first heterologous displacer tag (D1) located 5' to T1, and (c) optionally, an intervening spacer segment (S1) between T1 and D1 (also referred to herein as a "T1-D1 forward amplification oligomer"). The method generally comprises contacting a target nucleic acid comprising the target region with (1) the first amplification oligomer, wherein the contacting includes conditions whereby the target nucleic acid serves as a template for extension from the first amplification oligomer to produce a first amplification product comprising T1 and D1; (2) a second amplification oligomer comprising a target-binding segment T2 substantially complementary to a region of the first amplicon that is the complement of a 5'-end of the target region, wherein the contacting further includes conditions whereby the first amplicon serves as a template to produce a second amplicon comprising segments cT1 and cD1, complementary to T1 and D1, respectively; (3) a third amplification oligomer comprising target-binding priming segment $T1_p$ having a nucleotide sequence substantially corresponding to T1, or substantially corresponding to the complement of a second amplicon target sequence cT1' near or overlapping with cT1 and situated 5' to cD1; and (4) a fourth amplification oligomer comprising a displacer priming segment $D1_p$ having a nucleotide sequence substantially corresponding to D1; wherein the contacting further includes conditions whereby the second amplicon serves as a template for extension from both the third and fourth amplification oligomers, wherein extension of $T1_p$ from a $T1_p$:cT1 or $T1_p$:cT1' hybrid produces a third amplicon, and wherein extension of $D1_p$ from a $D1_p$:cD1 hybrid produces a fourth amplicon while displacing the third amplicon.

In certain embodiments of the above method, the first amplification oligomer further comprises a second heterologous displacer tag (D2) located 5' to D1 and, optionally, a second intervening spacer segment (S2) between D1 and D2, such that the first amplicon further comprises D2 and the second amplicon further comprises segment cD2, complementary to D2. Typically, in such embodiments, the target nucleic acid is further contacted with (5) a fifth amplification oligomer comprising a second displacer priming segment $D2_p$ having a nucleotide sequence substantially corresponding to D2, under conditions whereby (i) the second amplicon serves as a template for extension from the fifth amplification oligomer, wherein extension of $D2_p$ from a $D2_p$:cD2 hybrid produces a fifth amplicon comprising T1, D1, and $D2_p$, and (ii) the fifth amplicon serves as a template for amplification from the second amplification oligomer to produce a sixth amplicon comprising cT1, cD1, and $cD2_p$. In a further variation, the target nucleic acid is also contacted with (6) a sixth amplification oligomer comprising (a) priming segment $D1_p$ and (b) displacer tag D2 located 5' to $D1_p$, under conditions whereby (i) the fourth amplicon serves as a template for amplification from the second amplification oligomer to produce a seventh amplicon comprising segments cT1 and $cD1_p$, (ii) at least one of the second, sixth, and seventh amplicons serves as a template for extension from the sixth amplification oligomer, wherein extension of $D1_p$ from a $D1_p$:cD1 or $D1_p$:$cD1_p$ hybrid produces an eighth amplicon comprising T1, $D1_p$, and D2, and (iii) the eighth amplicon serves as a template for amplification from the second amplification oligomer to produce a ninth amplicon comprising cT1, $cD1_p$, and cD2. In some embodiments, the first amplification oligomer further comprises a third heterologous displacer tag (D3) located 5' to D2 and, optionally, a third intervening spacer segment (S3) between D2 and D3, whereby the first amplicon further comprises D3 and the second amplicon further comprises a segment cD3, complementary to D3; typically, in these variations, the target nucleic acid is further contacted with (7) a seventh oligonucleotide amplification oligomer comprising a third displacer priming segment $D3_p$ having a nucleotide sequence substantially corresponding to D3, under conditions whereby (i) the second amplicon serves as a template for extension from the seventh amplification oligomer, wherein extension of $D3_p$ from a $D3_p$:cD3 hybrid produces a tenth amplicon comprising T1, D1, D2, and $D3_p$, and (ii) the tenth amplicon serves as a template for amplification from the second amplification oligomer to produce an eleventh amplicon comprising cT1, cD1, cD2, and $cD3_p$. In yet another variation, the target nucleic acid is further contacted with (8) an eighth amplification oligomer comprising (a) priming segment $D2_p$ and (b) displacer tag D3 located 5' to $D2_p$, under conditions whereby (i) at least one of the second, sixth, ninth, and eleventh amplicons serves as a template for extension from the eighth amplification oligomer, wherein extension of $D2_p$ from a $D2_p$:cD2 or $D2_p$:$cD2_p$ hybrid produces a twelfth amplicon comprising T1, D1 (or $D1_p$), $D2_p$, and D3; and (ii) the twelfth amplicon serves as a template for amplification from the second amplification oligomer to produce a thirteenth amplicon comprising cT1, cD1 (or $cD1_p$), $cD2_p$, and cD3.

In other embodiments of the method using a T1-D1 forward amplification oligomer as set forth above, the target nucleic acid is further contacted with (5) a fifth amplification oligomer comprising (a) priming segment $D1_p$ and (b) displacer tag D2 located 5' to $D1_p$; and (6) a sixth amplification oligomer comprising a second displacer priming segment $D2_p$ having a nucleotide sequence substantially corresponding to D2. In such variations, the contacting typically includes conditions whereby (i) the fourth amplicon serves as a template for amplification from the second amplification oligomer to produce a fifth amplicon comprising segments cT1 and $cD1_p$, (ii) at least one of the second and fifth amplicons serves as a template for extension from the fifth amplification oligomer, wherein extension of $D1_p$ from a $D1_p$:cD1 or $D1_p$:$cD1_p$ hybrid produces a sixth amplicon comprising T1, $D1_p$, and D2, (iii) the sixth amplicon serves as a template for amplification from the second amplification oligomer to produce a seventh amplicon comprising cT1, $cD1_p$, and cD2, (iv) the seventh amplicon serves as a template for extension from the sixth amplification oligomer, wherein extension of $D2_p$ from a $D2_p$:cD2 hybrid produces an eighth amplicon comprising T1, $D1_p$, and $D2_p$, and (v) the eighth amplicon serves as a template for amplification from the second amplification oligomer to produce a ninth amplicon comprising cT1, $cD1_p$, and $cD2_p$. In a further variation, the target nucleic acid is further contacted with (7) a seventh amplification oligomer comprising (a) priming segment $D2_p$ and (b) displacer tag D3 located 5' to $D2_p$, and (8) an eighth oligonucleotide amplification oligomer comprising a third displacer priming segment $D3_p$ having a nucleotide sequence substantially corresponding to D3. In such embodiments, the contacting typically includes conditions whereby (i) at least one of the seventh and ninth amplicons serves as a template for extension from the seventh amplification oligomer, wherein extension of $D2_p$ from a $D2_p$:cD2 or $D2_p$:$cD2_p$ hybrid produces a tenth amplicon comprising T1, D1 (or $D1_p$), $D2_p$, and D3, (ii) the tenth amplicon serves as a template for amplification from the second amplification oligomer to produce an eleventh amplicon comprising cT1, cD1 (or $cD1_p$), $cD2_p$, and cD3, (iii) the eleventh amplicon serves as a template for extension from the eighth amplification oligomer, wherein extension of $D3_p$ from a $D3_p$:cD3 hybrid produces a twelfth amplicon comprising T1, D1, D2, and $D3_p$, and (iv) the twelfth amplicon serves as a template for amplification from the second amplification oligomer to produce a thirteenth amplicon comprising cT1, cD1, cD2, and $cD3_p$.

In any of the above embodiments, the second amplification oligomer may further comprise a fourth heterologous displacer tag (D4) located 5' to T2 and, optionally, a fourth intervening spacer segment (S4) between T2 and D4, such that the second amplicon comprises T2 and D4, and each of the third and fourth amplicons comprises segments cT2 and cD4, complementary to T2 and D4, respectively. In such variations, the target nucleic acid is further contacted with (9) a ninth amplification oligomer comprising a priming segment $T2_p$ having a nucleotide sequence substantially corresponding to T2, or substantially corresponding to the complement of a third or fourth amplicon target sequence cT2' near or overlapping with cT2 and situated 5' to cD4; and (10) a tenth amplification oligomer comprising a fourth displacer priming segment $D4_p$ having a nucleotide sequence substantially corresponding to D4, under conditions whereby at least one of the third and fourth amplicons serves as a template for extension from both the ninth and tenth amplification oligomers, wherein extension of $T2_p$ from a $T2_p$:cT2 or $T2_p$:cT2' hybrid produces a fourteenth amplicon, and wherein extension of $D4_p$ from a $D4_p$:cD4 hybrid produces a fifteenth amplicon while displacing the fourteenth amplicon.

In certain embodiments of the method as above, the affinity of $D1_p$ for its complement is lower than that of T1. In other embodiments comprising the use of a $D2_p$ displacer oligomer, (a) the affinity of $D1_p$ for its complement is lower than that of T1 and/or (b) the affinity of $D2_p$ for its complement is lower than that of $D1_p$. In yet other embodiments comprising the use of a $D3_p$ displacer oligomer, (a) the affinity of $D1_p$ for its complement is lower than that of T1 and/or (b) the affinity of $D2_p$ for its complement is lower than that of $D1_p$ and/or (c) the affinity of $D3_p$ for its complement is lower than that of $D2_p$.

In some embodiments of the method as above, the target nucleic acid is RNA. In some such embodiments, extension from the first amplification oligomer comprises contacting the target nucleic acid with a reverse transcriptase (RT). In more particular variations, the second amplification oligomer further comprises an RNA polymerase promoter sequence (P) (e.g., a T7 promoter sequence) located 5' to T2, such that each of the third and fourth amplicons comprises a segment cP, complementary to the promoter sequence; and contacting the target nucleic acid further includes conditions whereby an RNA polymerase initiates transcription upon recognizing a double stranded promoter sequence (P:cP) formed by extension of either the third or fourth amplification oligomer on the second amplicon, thereby producing an RNA amplicon. In a related variation, the second amplification oligomer further comprises an RNA polymerase promoter sequence (P) (e.g., a T7 promoter sequence) located 5' to T2 and is modified to prevent the initiation of DNA synthesis from its 3'-end, and the target nucleic acid is further contacted with a terminating oligonucleotide comprising a target-binding sequence substantially complementary to a target sequence that is adjacent to the 5'-end of the target region. In these embodiments, contacting the target nucleic acid typically includes conditions whereby extension of the first amplification oligomer is terminated at the 3'-end of the terminating oligonucleotide, thereby providing a 3'-end for the first amplicon that corresponds to the 5'-end of the target region; the promoter sequence P of the second amplification oligonucleotide serves as a template for extension from the 3'-end of the first amplicon, whereby the first amplicon comprises a segment cP, complementary to the promoter sequence, thereby forming a double stranded promoter sequence (P:cP); and an RNA polymerase initiates transcription upon recognizing the double stranded promoter sequence, thereby producing an RNA amplicon as the second amplicon.

In some embodiments, the method of amplifying a nucleic acid target region uses a second reverse amplification oligomer comprising (a) a target-binding segment T2 substantially complementary to a region of a first amplicon that is the complement of a 5'-end of the target region, (b) a first heterologous displacer tag (D1) located 5' to T2, and (c) optionally, an intervening spacer segment (S1) between T2 and D1 (also referred to herein as a "T2-D1 reverse amplification oligomer"). The method generally comprises contacting a target nucleic acid comprising the target region with (1) a first amplification oligomer comprising a target-binding priming segment (T1) substantially complementary to a 3'-end of the target region; wherein the contacting includes conditions whereby the target nucleic acid serves as a template for extension from the first amplification oligomer to produce a first amplicon; (2) the second amplification oligomer, wherein the contacting further includes conditions whereby the first amplicon serves as a template for amplification from the second amplification oligomer to produce a second amplicon comprising T2 and D1, and whereby the second amplicon serves as a template for extension from the first amplification oligomer to produce a third amplicon comprising segments cT2 and cD1, complementary to T2 and D1, respectively; (3) a third amplification oligomer comprising target-binding priming segment $T2_p$ having a nucleotide sequence substantially corresponding to T2, or substantially corresponding to the complement of a third amplicon target sequence cT2' near or overlapping with cT2 and situated 5' to cD1; and (4) a fourth amplification oligomer comprising a displacer priming segment $D1_p$ having a nucleotide sequence substantially corresponding to D1; wherein the contacting further includes conditions whereby the third amplicon serves as a template for extension from both the third and fourth amplification oligomers, wherein extension of $T2_p$ from a $T2_p$:cT2 or $T2_p$:cT2' hybrid produces a fourth amplicon, and wherein extension of $D1_p$ from a $D1_p$:cD1 hybrid produces a fifth amplicon while displacing the fourth amplicon.

In certain embodiments of the above method using a T2-D1 reverse amplification oligomer, the second (T2-D1 reverse) amplification oligomer further comprises a second heterologous displacer tag (D2) located 5' to D1 and, optionally, a second intervening spacer segment (S2) between D1 and D2, such that the second amplicon further comprises D2 and the third amplicon further comprises segment cD2, complementary to D2. Typically, in such embodiments, the target nucleic acid is further contacted with (5) a fifth amplification oligomer comprising a second displacer priming segment $D2_p$ having a nucleotide sequence substantially corresponding to D2, under conditions whereby (i) the third amplicon serves as a template for extension from the fifth amplification oligomer, wherein extension of $D2_p$ from a $D2_p$:cD2 hybrid produces a sixth amplicon comprising T2, D1, and $D2_p$, and (ii) the sixth amplicon serves as a template for extension from the first amplification oligomer to produce a seventh amplicon comprising cT2, cD1, and $cD2_p$. In a further variation, the target nucleic acid is also contacted with (6) a sixth amplification oligomer comprising (a) priming segment $D1_p$ and (b) displacer tag D2 located 5' to $D1_p$, under conditions whereby (i) the fifth amplicon serves as a template for extension from the first amplification oligomer to produce an eighth amplicon comprising segments cT2 and $cD1_p$, (ii) at least one of the third, seventh, and eighth amplicons serves as a template for extension from the sixth amplification oligomer, wherein extension of $D1_p$ from a $D1_p$:cD1 or $D1_p$:$cD1_p$ hybrid produces a ninth amplicon comprising T2, $D1_p$, and D2, and (iii) the ninth amplicon serves as a template for extension from the first amplification oligomer to produce a tenth amplicon comprising cT2, $cD1_p$, and cD2. In some embodiments, the second amplification oligomer further comprises a third heterologous displacer tag (D3) located 5' to D2 and, optionally, a third intervening spacer segment (S3) between D2 and D3, whereby the second amplicon further comprises D3 and the third amplicon further comprises a segment cD3, complementary to D3; in these variations, the target nucleic acid is further contacted with (7) a seventh amplification oligomer comprising a third displacer priming segment $D3_p$ having a nucleotide sequence substantially corresponding to D3, under conditions whereby (i) the third amplicon serves as a template for extension from the seventh amplification oligomer, wherein extension of $D3_p$ from a $D3_p$:cD3 hybrid produces an eleventh amplicon comprising T2, D1, D2, and $D3_p$, and (ii) the eleventh amplicon serves as a template for extension from the first amplification oligomer to produce a twelfth amplicon comprising cT2, cD1, cD2, and $cD3_p$. In yet a another variation, the target nucleic acid is further contacted with (8) an eighth amplification oligomer comprising (a) priming segment $D2_p$ and (b) displacer tag D3 located 5' to $D2_p$, under conditions whereby (i) at least one of the third, seventh, tenth, and twelfth amplicons serves as a template for extension from the eighth amplification oligomer, wherein extension of $D2_p$ from a $D2_p$:cD2 or $D2_p$:$cD2_p$ hybrid produces a thirteenth amplicon comprising T2, D1 (or $D1_p$), $D2_p$, and D3, and (ii) the thirteenth amplicon serves as a template for extension from the first amplification oligomer to produce a fourteenth amplicon comprising cT2, cD1 (or $cD1_p$), $cD2_p$, and cD3.

In other embodiments of the method using a T2-D1 reverse amplification oligomer as set forth above, the target nucleic acid is further contacted with (5) a fifth amplification oligomer comprising (a) priming segment $D1_p$ and (b) displacer tag D2 located 5' to $D1_p$; and (6) a sixth amplification oligomer comprising a second displacer priming segment $D2_p$ having a nucleotide sequence substantially corresponding to D2. In such variations, the contacting typically includes conditions whereby (i) the fifth amplicon serves as a template for extension from the first amplification oligomer to produce a sixth amplicon comprising segments cT2 and $cD1_p$, (ii) at least one of the third and sixth amplicons serves as a template for extension from the fifth amplification oligomer, wherein extension of $D1_p$ from a $D1_p$:cD1 or $D1_p$:$cD1_p$ hybrid produces a seventh amplicon comprising T2, $D1_p$, and D2, (iii) the seventh amplicon serves as a template for extension from the first amplification oligomer to produce an eighth amplicon comprising cT2, $cD1_p$, and cD2, (iv) the eighth amplicon serves as a template for extension from the sixth amplification oligomer, wherein extension of $D2_p$ from a $D2_p$:cD2 hybrid produces a ninth amplicon comprising T2, D1, and $D2_p$, and (v) the ninth amplicon serves as a template for extension from the first amplification oligomer to produce a tenth amplicon comprising cT2, cD1, and $cD2_p$. In a further variation, the target nucleic acid is further contacted with (7) a seventh amplification oligomer comprising (a) priming segment $D2_p$ and (b) displacer tag D3 located 5' to $D2_p$, and (8) an eighth amplification oligomer comprising a third displacer priming segment $D3_p$ having a nucleotide sequence substantially corresponding to D3. In such embodiments, the contacting typically includes conditions whereby (i) at least one of the eighth and tenth amplicons serves as a template for extension from the seventh amplification oligomer, wherein extension of $D2_p$ from a $D2_p$:cD2 or $D2_p$:$cD2_p$ hybrid produces an eleventh amplicon comprising T2, D1 (or $D1_p$), $D2_p$, and D3, (ii) the eleventh amplicon serves as a template for extension from the first amplification oligomer to produce a twelfth amplicon comprising cT2, cD1 (or $cD1_p$), $cD2_p$, and cD3, (iii) the twelfth amplicon serves as a template for extension from the eighth amplification oligomer, wherein extension of $D3_p$ from a $D3_p$:cD3 hybrid produces an thirteenth amplicon comprising T2, D1, D2, and $D3_p$, and (iv) the thirteenth amplicon serves as a template for extension from the first amplification oligomer to produce a fourteenth amplicon comprising cT2, cD1, cD2, and $cD3_p$.

In any of the above embodiments, the first amplification oligomer may further comprise a fourth heterologous displacer tag (D4) located 5' to T1 and, optionally, a fourth intervening spacer segment (S4) between T1 and D4, such that the first amplicon comprises T1 and D4, and the second amplicon comprises segments cT1 and cD4, complementary to T1 and D4, respectively. In such variations, the target nucleic acid is further contacted with a (9) a ninth amplification oligomer comprising a priming segment $T1_p$ having a nucleotide sequence substantially corresponding to T1, or substantially corresponding to the complement of a second amplicon target sequence cT1' near or overlapping with cT1 and situated 5' to cD4; and (10) a tenth amplification oligomer comprising a fourth displacer priming segment $D4_p$ having a nucleotide sequence substantially corresponding to D4, under conditions whereby the second amplicon serves as a template for extension from both the ninth and tenth amplification oligomers, wherein extension of $T1_p$ from a $T1_p$:cT1 or $T1_p$:cT1' hybrid produces a fifteenth amplicon, and wherein extension of $D4_p$ from a $D4_p$:cD4 hybrid produces a sixteenth amplicon while displacing the fifteenth amplicon.

In certain embodiments of the method using a T2-D1 reverse amplification oligomer as set forth above, the affinity of $D1_p$ for its complement is lower than that of T1. In other embodiments comprising the use of a D2p displacer oligomer, (a) the affinity of $D1_p$ for its complement is lower than that of T2 and/or (b) the affinity of $D2_p$ for its complement is lower than that of $D1_p$. In yet other embodiments comprising the use of a D3p displacer oligomer, (a) the affinity of $D1_p$ for its complement is lower than that of T2 and/or (b) the affinity of $D2_p$ for its complement is lower than that of $D1_p$ and/or (c) the affinity of $D3_p$ for its complement is lower than that of $D2_p$.

In some embodiments of the method using a T2-D1 reverse amplification oligomer as set forth above, the target nucleic acid is RNA. In some such embodiments, extension from the first amplification oligomer comprises contacting the target nucleic acid with a reverse transcriptase (RT). In more particular variations, the first amplification oligomer further comprises an RNA polymerase promoter sequence (P) (e.g., at T7 promoter sequence) located 5' to T1, such that the second amplicon comprises a segment cP, complementary to the promoter sequence; and contacting the target nucleic acid further includes conditions whereby an RNA polymerase initiates transcription upon recognizing a double-stranded promoter sequence (P:cP) formed by extension of the second amplification oligomer on the first amplicon, thereby producing an RNA amplicon.

In more particular embodiments of the above method utilizing either a T1-D1 forward amplification oligomer or a T2-D1 reverse amplification oligomer and further comprising a D2 displacer tag, D1 and D2 are different (i.e., have different nucleotide sequences); in alternative embodiments, D1 and D2 are the same. In more particular embodiments of the above method further comprising a D3 displacer tag, at least two (e.g., all three) of D1, D2, and D3 are different; in alternative embodiments, at least two (e.g., all three) of D1, D2, and D3 are the same.

In other embodiments, the method of amplifying a nucleic acid target region uses a first forward amplification oligomer comprising (a) a target-binding priming segment (T1) substantially complementary to a 3'-end of the target region, (b) a heterologous universal tag (U1) located 5' to T1, (c) a first heterologous displacer tag (D1) located 5' to U1, and (d) optionally, an intervening spacer segment (S1) between U1 and D1 (also referred to herein as a "T1-U1-D1 forward amplification oligomer"). The method generally comprises contacting a target nucleic acid comprising the target region with (1) the first amplification oligomer, wherein the contacting includes conditions whereby the target nucleic acid serves as a template for extension from the first amplification oligomer to produce a first amplicon comprising U1 and D1; (2) a second amplification oligomer comprising (a) a target-binding segment T2 substantially complementary to a region of the first amplicon that is the complement of a 5'-end of the target region and (b) optionally, a heterologous universal tag (U2) located 5' to T2, wherein the contacting further includes conditions whereby the first amplicon serves as a template for amplification from the second amplification oligomer to produce a second amplicon comprising segments cU1 and cD1, complementary to U1 and D1, respectively, and optionally comprising U2; (3) a third amplification oligomer comprising a universal priming segment $U1_p$ having a nucleotide sequence substantially corresponding to U1; (4) a fourth amplification oligomer comprising a displacer priming segment $D1_p$ having a nucleotide sequence substantially corresponding to D1; and (5) if the second amplification oligomer comprises U2, a fifth amplification oligomer comprising a second universal priming segment $U2_p$ having a nucleotide sequence substantially corresponding to U2; wherein the contacting further includes conditions whereby the second amplicon serves as a template for extension from both the third and fourth amplification oligomers, wherein extension of $U1_p$ from a $U1_p$:cU1 hybrid produces a third amplicon, and wherein extension of $D1_p$ from a $D1_p$:cD1 hybrid produces a fourth amplicon while displacing the third amplicon.

In certain embodiments of the above method utilizing a T1-U1-D1 forward amplification oligomer, the first amplification oligomer further comprises a second heterologous displacer tag (D2) located 5' to D1 and, optionally, a second intervening spacer segment (S2) between D1 and D2, such that the first amplicon further comprises D2 and the second amplicon further comprises segment cD2, complementary to D2. Typically, in such embodiments, the target nucleic acid is further contacted with (6) a sixth amplification oligomer comprising a second displacer priming segment $D2_p$ having a nucleotide sequence substantially corresponding to D2, wherein the contacting includes conditions whereby (i) the second amplicon serves as a template for extension from the sixth amplification oligomer, wherein extension of $D2_p$ from a $D2_p$:cD2 hybrid produces a fifth amplicon comprising U1, D1, and $D2_p$, and (ii) the fifth amplicon serves as a template for amplification from the second or fifth amplification oligomer to produce a sixth amplicon comprising cU1, cD1, and $cD2_p$. In a further variation, the target nucleic acid is also contacted with (7) a seventh amplification oligomer comprising (a) priming segment $D1_p$ and (b) displacer tag D2 located 5' to $D1_p$, under conditions whereby (i) the fourth amplicon serves as a template for amplification from the second or fifth amplification oligomer to produce a seventh amplicon comprising segments cT1 and $cD1_p$, (ii) at least one of the second, sixth, and seventh amplicons serves as a template for extension from the seventh amplification oligomer, wherein extension of $D1_p$ from a $D1_p$:cD1 or $D1_p$:$cD1_p$ hybrid produces an eighth amplicon comprising U1, $D1_p$, and D2, and (iii) the eighth amplicon serves as a template for amplification from the second or fifth amplification oligomer to produce a ninth amplicon comprising cU1, $cD1_p$, and cD2. In some embodiments, the first amplification oligomer further comprises a third heterologous displacer tag (D3) located 5' to D2 and, optionally, a third intervening spacer segment (S3) between D2 and D3, whereby the first amplicon further comprises D3 and the second amplicon further comprises a segment cD3, complementary to D3; typically, in these variations, the target nucleic acid is further contacted with (8) an eighth amplification oligomer comprising a third displacer priming segment $D3_p$ having a nucleotide sequence substantially corresponding to D3, under conditions whereby (i) the second amplicon serves as a template for extension from the eighth amplification oligomer, wherein extension of $D3_p$ from a $D3_p$:cD3 hybrid produces a tenth amplicon comprising U1, D1, D2, and $D3_p$; and (ii) the tenth amplicon serves as a template for amplification from the second or fifth amplification oligomer to produce an eleventh amplicon comprising cU1, cD1, cD2, and $cD3_p$. In yet another variation, the target nucleic acid is further contacted with (9) a ninth amplification oligomer comprising (a) priming segment $D2_p$ and (b) displacer tag D3 located 5' to $D2_p$, under conditions whereby (i) at least one of the second, sixth, ninth, and eleventh amplicons serves as a template for extension from the seventh amplification oligomer, wherein extension of $D2_p$ from a $D2_p$:cD2 or $D2_p$:$cD2_p$ hybrid produces a twelfth amplicon comprising U1, D1 (or $D1_p$), D2p, and D3, and (ii) the twelfth amplicon serves as a template for amplification from the second or fifth amplification oligomer to produce a thirteenth amplicon comprising cU1, cD1 (or $cD1_p$), $cD2_p$, and cD3.

In other embodiments of the method using a T1-U1-D1 forward amplification oligomer as set forth above, the target nucleic acid is further contacted with (6) a sixth amplification oligomer comprising (a) priming segment $D1_p$ and (b) displacer tag D2 located 5' to $D1_p$, and (7) a seventh amplification oligomer comprising a second displacer priming segment $D2_p$ having a nucleotide sequence substantially corresponding to D2. In such variations, the contacting typically includes conditions whereby (i) the fourth amplicon serves as a template for amplification from the second or fifth amplification oligomer to produce a fifth amplicon comprising segments cU1 and $cD1_p$, (ii) at least one of the second and fifth amplicons serves as a template for extension from the sixth amplification oligomer, wherein extension of $D1_p$ from a $D1_p$:cD1 or $D1_p$:$cD1_p$ hybrid produces a sixth amplicon comprising U1, $D1_p$, and D2, (iii) the sixth amplicon serves as a template for amplification from the second amplification oligomer to produce a seventh amplicon comprising cU1, $cD1_p$, and cD2; (iv) the seventh amplicon serves as a template for extension from the seventh amplification oligomer, wherein extension of $D2_p$ from a $D2_p$:cD2 hybrid produces an eighth amplicon comprising U1, $D1_p$, and $D2_p$, and (v) the eighth amplicon serves as a template for amplification from the second or fifth amplification oligomer to produce a ninth amplicon comprising cU1, $cD1_p$, and $cD2_p$. In a further variation, the target nucleic acid is further contacted with (8) an eighth amplification oligomer comprising (a) priming segment $D2_p$ and (b) displacer tag D3 located 5' to $D2_p$, and (9) a ninth oligonucleotide amplification oligomer comprising a third displacer priming segment $D3_p$ having a nucleotide sequence substantially corresponding to D3. In such embodiments, the contacting typically includes conditions whereby (i) at least one of the seventh and ninth amplicons serves as a template for extension from the eighth amplification oligomer, wherein extension of $D2_p$ from a $D2_p$:cD2 or $D2_p$:$cD2_p$ hybrid produces a tenth amplicon comprising U1, $D1/D1_p$, $D2_p$, and D3, (ii) the tenth amplicon serves as a template for amplification from the second or fifth amplification oligomer to produce an eleventh amplicon comprising cU1, cD1 (or cD1$_p$), cD2$_p$, and cD3, (iii) the eleventh amplicon serves as a template for extension from the ninth amplification oligomer, wherein extension of D3$_p$ from a D3$_p$:cD3 hybrid produces a twelfth amplicon comprising U1, D1, D2, and D3$_p$, and (iv) the twelfth amplicon serves as a template for amplification from the second or fifth amplification oligomer to produce a thirteenth amplicon comprising cU1, cD1, cD2, and cD3$_p$.

In any of the above embodiments using a T1-U1-D1 forward amplification oligomer, the second amplification oligomer may further comprise a fourth heterologous displacer tag (D4) located 5' to T2 and, optionally, a fourth intervening spacer segment between T2 and D4, whereby the second amplicon comprises T2 and D4; and whereby each of the third and fourth amplicons comprises segments cT2 and cD4, complementary to T2 and D4, respectively. Typically, in such variations, the target nucleic acid is further contacted with (10) a tenth amplification oligomer comprising a priming segment T2$_p$ having a nucleotide sequence substantially corresponding to T2, or substantially corresponding to the complement of a third or fourth amplicon target sequence cT2' near or overlapping with cT2 and situated 5' to cD4, and (11) an eleventh amplification oligomer comprising a fourth displacer priming segment D4$_p$ having a nucleotide sequence substantially corresponding to D4, under conditions whereby at least one of the third and fourth amplicons serves as a template for extension from both the tenth and eleventh amplification oligomers, wherein extension of T2$_p$ from a T2$_p$:cT2 or T2$_p$:cT2' hybrid produces a fourteenth amplicon, and wherein extension of D4$_p$ from a D4$_p$:cD4 hybrid produces a fifteenth amplicon while displacing the fourteenth amplicon.

In other embodiments of the method using a T1-U1-D1 forward amplification oligomer as set forth above, the second amplification oligomer comprises U2 and further comprises a fourth heterologous displacer tag (D4) located 5' to U2 and, optionally, a fourth intervening spacer segment (S4) between U2 and D4, whereby the second amplicon comprises U2 and D4; and whereby each of the third and fourth amplicons comprises segments cU2 and cD4, complementary to U2 and D4, respectively. Typically, in such variations, the target nucleic acid is further contacted with (10) a tenth amplification oligomer comprising a fourth displacer priming segment D4$_p$ having a nucleotide sequence substantially corresponding to D4, under conditions whereby at least one of the third and fourth amplicons serves as a template for extension from both the fifth and tenth amplification oligomers, wherein extension of U2$_p$ from a U2$_p$:cU2 hybrid produces a fourteenth amplicon, and wherein extension of D4$_p$ from a D4$_p$:cD4 hybrid produces a fifteenth amplicon while displacing the fourteenth amplicon.

In certain embodiments of the method using a T1-U1-D1 forward amplification oligomer as set forth above, the affinity of D1$_p$ for its complement is lower than that of U1. In other embodiments comprising the use of a D2p displacer oligomer, (a) the affinity of D1$_p$ for its complement is lower than that of U1 and/or (b) the affinity of D2$_p$ for its complement is lower than that of D1$_p$. In yet other embodiments comprising the use of a D3$_p$ displacer oligomer, (a) the affinity of D1$_p$ for its complement is lower than that of U1 and/or (b) the affinity of D2$_p$ for its complement is lower than that of D1$_p$ and/or (c) the affinity of D3$_p$ for its complement is lower than that of D2$_p$.

In some embodiments of the method using a T1-U1-D1 forward amplification oligomer as set forth above, the target nucleic acid is RNA. In some such embodiments, extension from the first amplification oligomer comprises contacting the target nucleic acid with a reverse transcriptase (RT). In more particular variations, the second amplification oligomer further comprises an RNA polymerase promoter sequence (P) (e.g., a T7 promoter sequence) located 5' to T2, such that each of the third and fourth amplicons comprises a segment cP, complementary to the promoter sequence; and contacting the nucleic acid further comprises conditions whereby an RNA polymerase initiates transcription upon recognizing a double-stranded promoter sequence (P:cP) formed by extension of either the third or fourth amplification oligomer on the second amplicon, thereby producing an RNA amplicon. In a related variation, the second amplification oligomer further comprises an RNA polymerase promoter sequence (P) (e.g., a T7 promoter sequence) located 5' to T2 and is modified to prevent the initiation of DNA synthesis from its 3'-end, and the target nucleic acid is further contacted with a terminating oligonucleotide comprising a target-binding sequence substantially complementary to a target sequence that is adjacent to the 5'-end of the target region. In these embodiments, contacting the target nucleic acid typically includes conditions whereby extension of the first amplification oligomer is terminated at the 3'-end of the terminating oligonucleotide, thereby providing a 3'-end for the first amplicon that corresponds to the 5'-end of the target region; the promoter sequence P of the second amplification oligonucleotide serves as a template for extension from the 3'-end of the first amplicon, whereby the first amplicon comprises a segment cP, complementary to the promoter sequence, thereby forming a double stranded promoter sequence (P:cP); and an RNA polymerase initiates transcription upon recognizing the double stranded promoter sequence, thereby producing an RNA amplicon as the second amplicon.

In some embodiments, the method of amplifying a nucleic acid target region uses a second reverse amplification oligomer comprising (a) a target-binding segment T2 substantially complementary to a region of the first amplicon that is the complement of a 5'-end of the target region, (b) a heterologous universal tag (U1) located 5' to T2, (c) a first heterologous displacer tag (D1) located 5' to U1, and (d) optionally, an intervening spacer segment (S1) between U1 and D1 (also referred to herein as a "T2-U1-D1 reverse amplification oligomer"). The method generally comprises contacting a target nucleic acid comprising the target region with (1) a first amplification oligomer comprising (a) a target-binding priming segment (T1) substantially complementary to a 3'-end of the target region, and (b) optionally, a heterologous universal tag (U2) located 5' to T1; wherein the contacting includes conditions whereby the target nucleic acid serves as a template for extension from the first amplification oligomer to produce a first amplicon; (2) the second amplification oligomer comprising, wherein the contacting further includes conditions whereby the first amplicon serves as a template for amplification from the second amplification oligomer to produce a second amplicon comprising U1 and D1, and whereby the second amplicon serves as a template for extension from the first amplification oligomer to produce a third amplicon comprising segments cU1 and cD1, complementary to U1 and D1, respectively; (3) a third amplification oligomer comprising a universal priming segment U1$_p$ having a nucleotide sequence substantially corresponding to U1; (4) a fourth amplification oligomer comprising a displacer priming segment D1$_p$ having a nucleotide sequence substantially corresponding to D1; and (5) if the first amplification oligomer comprises U2, a fifth amplification oligomer comprising a second universal priming segment $U2_p$ having a nucleotide sequence substantially corresponding to U2; wherein the contacting further includes conditions whereby the third amplicon serves as a template for extension from both the third and fourth amplification oligomers, wherein extension of $U1_p$ from a $U1_p$:cU1 hybrid produces a fourth amplicon, and wherein extension of $D1_p$ from a $D1_p$:cD1 hybrid produces a fifth amplicon while displacing the fourth amplicon.

In certain embodiments of the above method using a T2-U1-D1 reverse amplification oligomer, the second (T2-U1-D1 reverse) amplification oligomer further comprises a second heterologous displacer tag (D2) located 5' to D1 and, optionally, a second intervening spacer segment (S2) between D1 and D2, whereby the second amplicon further comprises D2 and the third amplicon further comprises segment cD2, complementary to D2. Typically, in such embodiments, the target nucleic acid is further contacted with (6) a sixth amplification oligomer comprising a second displacer priming segment $D2_p$ having a nucleotide sequence substantially corresponding to D2, under conditions whereby (i) the third amplicon serves as a template for extension from the sixth amplification oligomer, wherein extension of $D2_p$ from a $D2_p$:cD2 hybrid produces a sixth amplicon comprising U1, D1, and $D2_p$, and (ii) the sixth amplicon serves as a template for extension from the first or fifth amplification oligomer to produce a seventh amplicon comprising cU1, cD1, and $cD2_p$. In a further variation, the target nucleic acid is also contacted with (7) a seventh amplification oligomer comprising (a) priming segment $D1_p$ and (b) displacer tag D2 located 5' to $D1_p$, under conditions whereby (i) the fifth amplicon serves as a template for extension from the first or fifth amplification oligomer to produce an eighth amplicon comprising segments cU1 and $cD1_p$, (ii) at least one of the third, seventh, and eighth amplicons serves as a template for extension from the seventh amplification oligomer, wherein extension of $D1_p$ from a $D1_p$:cD1 or $D1_p$:$cD1_p$ hybrid produces a ninth amplicon comprising U1, $D1_p$, and D2, and (iii) the ninth amplicon serves as a template for extension from the first or fifth amplification oligomer to produce a tenth amplicon comprising cU1, $cD1_p$, and cD2. In some embodiments, the second amplification oligomer further comprises a third heterologous displacer tag (D3) located 5' to D2 and, optionally, a third intervening spacer segment (S3) between D2 and D3, whereby the second amplicon further comprises D3 and the third amplicon further comprises a segment cD3, complementary to D3; and wherein the target nucleic acid is further contacted with (8) an eighth amplification oligomer comprising a third displacer priming segment $D3_p$ having a nucleotide sequence substantially corresponding to D3, under conditions whereby (i) the third amplicon serves as a template for extension from the eighth amplification oligomer, wherein extension of $D3_p$ from a $D3_p$:cD3 hybrid produces an eleventh amplicon comprising U1, D1, D2, and $D3_p$, (ii) the eleventh amplicon serves as a template for extension from the first or fifth amplification oligomer to produce an twelfth amplicon comprising cU1, cD1, cD2, and $cD3_p$. In yet another variation, the target nucleic acid is further contacted with (9) a ninth amplification oligomer comprising (a) priming segment $D2_p$ and (b) displacer tag D3 located 5' to $D2_p$, under conditions whereby (i) at least one of the third, seventh, tenth, and twelfth amplicons serves as a template for extension from the eighth amplification oligomer, wherein extension of $D2_p$ from a $D2_p$:cD2 or $D2_p$:$cD2_p$ hybrid produces a thirteenth amplicon comprising U1, D1 (or $D1_p$), $D2_p$, and D3, and (ii) the thirteenth amplicon serves as a template for extension from the first or fifth amplification oligomer to produce a fourteenth amplicon comprising cU1, cD1 (or $cD1_p$), $cD2_p$, and cD3.

In other embodiments of the method using a T2-U1-D1 reverse amplification oligomer as set forth above, the target nucleic acid is further contacted with (6) a sixth amplification oligomer comprising (a) priming segment $D1_p$ and (b) displacer tag D2 located 5' to $D1_p$, and (7) a seventh amplification oligomer comprising a second displacer priming segment $D2_p$ having a nucleotide sequence substantially corresponding to D2. In such variations, the contacting includes conditions whereby (i) the fifth amplicon serves as a template for extension from the first or fifth amplification oligomer to produce a sixth amplicon comprising segments cU2 and $cD1_p$, (ii) at least one of the third and sixth amplicons serves as a template for extension from the sixth amplification oligomer, wherein extension of $D1_p$ from a $D1_p$:cD1 or $D1_p$:$cD1_p$ hybrid produces a seventh amplicon comprising U2, $D1_p$, and D2, (iii) the seventh amplicon serves as a template for extension from the first amplification oligomer to produce an eighth amplicon comprising cU2, $cD1_p$, and cD2, (iv) the eighth amplicon serves as a template for extension from the seventh amplification oligomer, wherein extension of $D2_p$ from a $D2_p$:cD2 hybrid produces a ninth amplicon comprising U2, D1, and $D2_p$, and (v) the ninth amplicon serves as a template for extension from the first or fifth amplification oligomer to produce a tenth amplicon comprising cU2, cD1, and $cD2_p$. In a further variation, the target nucleic acid is also contacted with (8) an eighth amplification oligomer comprising (a) priming segment $D2_p$ and (b) displacer tag D3 located 5' to $D2_p$, and (9) a ninth amplification oligomer comprising a third displacer priming segment $D3_p$ having a nucleotide sequence substantially corresponding to D3. In such embodiments, the contacting typically includes conditions whereby (i) at least one of the eighth and tenth amplicons serves as a template for extension from the eighth amplification oligomer, wherein extension of $D2_p$ from a $D2_p$:cD2 or $D2_p$:$cD2_p$ hybrid produces an eleventh amplicon comprising U2, D1 (or $D1_p$), $D2_p$, and D3, (ii) the eleventh amplicon serves as a template for extension from the first or fifth amplification oligomer to produce a twelfth amplicon comprising cU2, cD1 (or $cD1_p$), $cD2_p$, and cD3, (iii) the twelfth amplicon serves as a template for extension from the ninth amplification oligomer, wherein extension of $D3_p$ from a $D3_p$:cD3 hybrid produces an thirteenth amplicon comprising U2, D1, D2, and $D3_p$, and (iv) the thirteenth amplicon serves as a template for extension from the first or fifth amplification oligomer to produce a fourteenth amplicon comprising cU2, cD1, cD2, and cD3p.

In any of the above embodiments using a T2-U1-D1 reverse amplification oligomer, the first amplification oligomer may further comprise a fourth heterologous displacer tag (D4) located 5' to T1 and, optionally, a fourth intervening spacer segment (S4) between T1 and D4, whereby the first amplicon comprises T1 and D4; and whereby the second amplicon comprises segments cT1 and cD4, complementary to T1 and D4, respectively. In such variations, the target nucleic acid is further contacted with (10) a tenth amplification oligomer comprising a priming segment $T1_p$ having a nucleotide sequence substantially corresponding to T1, or substantially corresponding to the complement of a second amplicon target sequence cT1' near or overlapping with cT1 and situated 5' to cD4, and (11) an eleventh amplification oligomer comprising a fourth displacer priming segment $D4_p$ having a nucleotide sequence substantially corresponding to D4, under conditions whereby the second amplicon serves as a template for extension from both the tenth and eleventh amplification oligomers, wherein extension of $T1_p$ from a $T1_p$:cT1 or $T1_p$:cT1' hybrid produces a fifteenth amplicon, and wherein extension of $D4_p$ from a $D4_p$:cD4 hybrid produces a sixteenth amplicon while displacing the fifteenth amplicon.

In other embodiments using a T2-U1-D1 reverse amplification oligomer as set forth above, the first amplification oligomer comprises U2 and further comprises a fourth heterologous displacer tag (D4) located 5' to U2 and, optionally, a fourth intervening spacer segment (S4) between U2 and D4, whereby the first amplicon comprises U2 and D4, and whereby the second amplicon comprises segments cU2 and cD4, complementary to U2 and D4, respectively. Typically, in such variations, the target nucleic acid is further contacted with (10) an eleventh amplification oligomer comprising a fourth displacer priming segment $D4_p$ having a nucleotide sequence substantially corresponding to D4, under conditions whereby the second amplicon serves as a template for extension from both the fifth and tenth amplification oligomers, wherein extension of $U2_p$ from a $U2_p$:cU2 hybrid produces a fifteenth amplicon, and wherein extension of $D4_p$ from a $D4_p$:cD4 hybrid produces a sixteenth amplicon while displacing the fifteenth amplicon.

In certain embodiments of the method using a T2-U1-D1 reverse amplification oligomer as set forth above, the affinity of $D1_p$ for its complement is lower than that of U1. In other embodiments comprising the use of a D2p displacer oligomer, (a) the affinity of $D1_p$ for its complement is lower than that of U1 and/or (b) the affinity of $D2_p$ for its complement is lower than that of $D1_p$. In yet other embodiments comprising the use of a $D3_p$ displacer oligomer, (a) the affinity of $D1_p$ for its complement is lower than that of U1 and/or (b) the affinity of $D2_p$ for its complement is lower than that of $D1_p$ and/or (c) the affinity of $D3_p$ for its complement is lower than that of $D2_p$.

In some embodiments of the method using a T2-U1-D1 reverse amplification oligomer as set forth above, the target nucleic acid is RNA. In some such embodiments, extension from the first amplification oligomer comprises contacting the target nucleic acid with a reverse transcriptase (RT). In more particular variations, the first amplification oligomer further comprises an RNA polymerase promoter sequence (P) (e.g., a T7 promoter sequence) located 5' to T1, such that the second amplicon comprises a segment cP, complementary to the promoter sequence; and contacting the target nucleic acid further includes conditions whereby an RNA polymerase initiates transcription upon recognizing a double-stranded promoter sequence (P:cP) formed by extension of the second amplification oligomer on the first amplicon, thereby producing an RNA amplicon.

In more particular embodiments of the above method utilizing either a T1-U1-D1 forward amplification oligomer or a T2-U1-D1 reverse amplification oligomer, U1 and D1 are different (i.e., have different nucleotide sequences); in alternative embodiments, U1 and D1 are the same. In more particular embodiments of the above method utilizing either a T1-U1-D1 forward amplification oligomer or a T2-U1-D1 reverse amplification oligomer and further comprising a D2 displacer tag, at least two (e.g., all three) of U1, D1, and D2 are different; in alternative embodiments, at least two (e.g., all three) of U1, D1, and D2 are the same. In yet other embodiments further comprising a D3 displacer tag, at least two (e.g., three or all four) of U1, D1, D2, and D3 are different; in alternative embodiments, at least two (e.g., three or all four) of U1, D1, D2, and D3 are the same.

In other aspects, the present invention provides a kit or reaction mixture for amplifying nucleic acid target region. In some embodiments, the kit or reaction mixture includes (1) a first amplification oligomer comprising (a) a target-binding priming segment (T1) substantially complementary to a 3'-end of the target region, (b) a first heterologous displacer tag (D1) located 5' to T1, and (c) optionally, an intervening spacer segment (S1) between T1 and D1; (2) a second amplification oligomer comprising a second priming segment T2 substantially complementary to the complement of a 5'-end of the target region; (3) a third amplification oligomer comprising target-binding priming segment $T1_p$ having a nucleotide sequence substantially corresponding to T1, or substantially corresponding to the complement of a target sequence that is within the target region and near or overlapping with the T1 target sequence; and (4) a fourth amplification oligomer comprising a displacer priming segment $D1_p$ having a nucleotide sequence substantially corresponding to D1. In some such embodiments, the first amplification oligomer further comprises a second heterologous displacer tag (D2) located 5' to D1 and, optionally, a second intervening spacer segment (S2) between D1 and D2; alternatively or additionally, the kit or reaction mixture further includes a fifth amplification oligomer comprising (a) priming segment $D1_p$ and (b) displacer tag D2 located 5' to $D1_p$. In some such variations, the kit or reaction mixture further includes a sixth amplification oligomer comprising a second displacer priming segment $D2_p$ having a nucleotide sequence substantially corresponding to D2. In other embodiments of the above kit or reaction mixture, the first amplification oligomer further comprises a third heterologous displacer tag (D3) located 5' to D2 and, optionally, a third intervening spacer segment (S3) between D2 and D3. In some variations, the kit or reaction mixture further includes a seventh amplification oligomer comprising (a) priming segment $D2_p$ and (b) displacer tag D3 located 5' to $D2_p$. In more particular variations of a kit or reaction mixture comprising a D3 tag, the kit or reaction mixture further includes an eighth amplification oligomer comprising a third displacer priming segment $D3_p$ having a nucleotide sequence substantially corresponding to D3. In some embodiments of a kit or reaction mixture as above, the second amplification oligomer further includes a fourth heterologous displacer tag (D4) located 5' to T2 and, optionally, a fourth intervening spacer segment (S4) between T2 and D4, and the kit or reaction mixture further includes a ninth amplification oligomer comprising a priming segment $T2_p$ having a nucleotide sequence substantially corresponding to T2 or substantially corresponding to a target sequence that is within the complement of the target region and near or overlapping with the T2 target sequence, and a tenth amplification oligomer comprising a fourth displacer priming segment $D4_p$ having a nucleotide sequence substantially corresponding to D4. In certain variations, the kit or reaction mixture further includes a reverse transcriptase (RT); in some such variations, the kit or reaction mixture further includes an RNA polymerase (e.g., a T7 polymerase), wherein the second amplification oligomer further comprises an RNA polymerase promoter sequence located 5' to T2.

In other embodiments, a kit or reaction mixture for amplifying a nucleic acid target region includes (1) a first amplification oligomer comprising a target-binding priming segment (T1) substantially complementary to a 3'-end of the target region; (2) a second amplification oligomer comprising (a) a target-binding segment T2 substantially complementary to the complement of a 5'-end of the target region, (b) a first heterologous displacer tag (D1) located 5' to T2, and (c) optionally, an intervening spacer segment (S1) between T2 and D1; (3) a third amplification oligomer comprising target-binding priming segment $T2_p$ having a nucleotide sequence substantially corresponding to T2, or substantially corresponding to a target sequence that is within the complement of the target region and near or overlapping with the T2 target sequence; and (4) a fourth amplification oligomer comprising a displacer priming segment $D1_p$ having a nucleotide sequence substantially corresponding to D1. In some such embodiments, the second amplification oligomer further comprises a second heterologous displacer tag (D2) located 5' to D1 and, optionally, a second intervening spacer segment (S2) between D1 and D2; alternatively or additionally, the kit or reaction mixture further includes a fifth amplification oligomer comprising (a) priming segment $D1_p$ and (b) displacer tag D2 located 5' to $D1_p$. In some such variations, the kit or reaction mixture further includes a sixth amplification oligomer comprising a second displacer priming segment $D2_p$ having a nucleotide sequence substantially corresponding to D2. In other embodiments of the above kit or reaction mixture, the second amplification oligomer further comprises a third heterologous displacer tag (D3) located 5' to D2 and, optionally, a third intervening spacer segment (S3) between D2 and D3. In some variations, the kit or reaction mixture further includes a seventh amplification oligomer comprising (a) priming segment $D2_p$ and (b) displacer tag D3 located 5' to $D2_p$. In more particular variations of a kit or reaction mixture comprising a D3 tag, the kit or reaction mixture further includes an eighth amplification oligomer comprising a third displacer priming segment $D3_p$ having a nucleotide sequence substantially corresponding to D3. In some embodiments of a kit or reaction mixture as above, the first amplification oligomer further includes a fourth heterologous displacer tag (D4) located 5' to T1 and, optionally, a fourth intervening spacer segment (S4) between T1 and D4, and the kit or reaction mixture further includes a ninth amplification oligomer comprising a priming segment $T1_p$ having a nucleotide sequence substantially corresponding to T1 or substantially corresponding to the complement of a target sequence that is within the target region and near or overlapping with the T1 target sequence, and a tenth amplification oligomer comprising a fourth displacer priming segment $D4_p$ having a nucleotide sequence substantially corresponding to D4. In certain variations, the kit or reaction mixture further includes a reverse transcriptase (RT); in some such variations, the kit or reaction mixture further includes an RNA polymerase (e.g., a T7 polymerase), wherein the first amplification oligomer further comprises an RNA polymerase promoter sequence located 5' to T1.

In yet other embodiments, a kit or reaction mixture for amplifying a nucleic acid target region includes (1) a first amplification oligomer comprising (a) a target-binding priming segment (T1) substantially complementary to a 3'-end of the target region, (b) a heterologous universal tag (U1) located 5' to T1, (c) a first heterologous displacer tag (D1) located 5' to U1, and (d) optionally, an intervening spacer segment (S1) between U1 and D1; (2) a second amplification oligomer comprising (a) a target-binding segment T2 substantially complementary to the complement of a 5'-end of the target region and (b) optionally, a heterologous universal tag (U2) located 5' to T2; (3) a third amplification oligomer comprising a universal priming segment $U1_p$ having a nucleotide sequence substantially corresponding to U1; (4) a fourth amplification oligomer comprising a displacer priming segment $D1_p$ having a nucleotide sequence substantially corresponding to D1; and (5) if the second amplification oligomer comprises U2, a fifth amplification oligomer comprising a second universal priming segment $U2_p$ having a nucleotide sequence substantially corresponding to U2. In some such embodiments, the first amplification oligomer further comprises a second heterologous displacer tag (D2) located 5' to D1 and, optionally, a second intervening spacer segment (S2) between D1 and D2; alternatively or additionally, the kit or reaction mixture further includes a sixth amplification oligomer comprising (a) priming segment $D1_p$ and (b) displacer tag D2 located 5' to $D1_p$. In some such variations, the kit or reaction mixture further includes a seventh amplification oligomer comprising a second displacer priming segment $D2_p$ having a nucleotide sequence substantially corresponding to D2. In other embodiments of the above kit or reaction mixture, the first amplification oligomer further comprises a third heterologous displacer tag (D3) located 5' to D2 and, optionally, a third intervening spacer segment (S3) between D2 and D3. In some variations, the kit or reaction mixture further includes an eighth amplification oligomer comprising (a) priming segment $D2_p$ and (b) displacer tag D3 located 5' to $D2_p$. In more particular variations of a kit or reaction mixture comprising a D3 tag, the kit or reaction mixture further includes an eighth amplification oligomer comprising a third displacer priming segment $D3_p$ having a nucleotide sequence substantially corresponding to D3. In some embodiments of a kit or reaction mixture as above, the second amplification oligomer further comprises a fourth heterologous displacer tag (D4) located 5' to T2 and, optionally, a fourth intervening spacer segment (S4) between T2 and D4, and the kit or reaction mixture further includes a tenth amplification oligomer comprising a priming segment $T2_p$ having a nucleotide sequence substantially corresponding to T2 or substantially corresponding to a target sequence that is within the complement of the target region and near or overlapping with the T2 target sequence, and an eleventh amplification oligomer comprising a fourth displacer priming segment $D4_p$ having a nucleotide sequence substantially corresponding to D4. In other embodiments, the second amplification oligomer comprises U2 and further comprises a fourth heterologous displacer tag (D4) located 5' to U2 and, optionally, a fourth intervening spacer segment (S4) between U2 and D4, and the kit or reaction mixture further includes a tenth amplification oligomer comprising a fourth displacer priming segment $D4_p$ having a nucleotide sequence substantially corresponding to D4. In certain variations, the kit or reaction mixture further includes a reverse transcriptase (RT); in some such variations, the kit or reaction mixture further includes an RNA polymerase (e.g., a T7 polymerase), wherein the second amplification oligomer further comprises an RNA polymerase promoter sequence located 5' to T2.

In still other embodiments, a kit or reaction mixture for amplifying a nucleic acid target region includes (1) a first amplification oligomer comprising (a) a target-binding priming segment (T1) substantially complementary to a 3'-end of the target nucleic acid and (b) optionally, a heterologous universal tag (U2) located 5' to T1; (2) a second amplification oligomer comprising (a) a target-binding segment T2 substantially complementary to the complement of a 5'-end of the target region, (b) a heterologous universal tag (U1) located 5' to T2, (c) a first heterologous displacer tag (D1) located 5' to U1, and (d), optionally, an intervening spacer segment between U1 and D1; (3) a third amplification oligomer comprising a universal priming segment $U1_p$ having a nucleotide sequence substantially corresponding to U1; (4) a fourth amplification oligomer comprising a displacer priming segment $D1_p$ having a nucleotide sequence substantially corresponding to D1; and (5) if the first amplification oligomer comprises U2, a fifth amplification oligomer comprising a second universal priming segment $U2_p$ having a nucleotide sequence substantially corresponding to U2. In some such embodiments, the second amplification oligomer further comprises a second heterologous displacer tag (D2) located 5' to D1 and, optionally, a second intervening spacer segment (S2) between D1 and D2; alternatively or additionally, the kit or reaction mixture further includes a sixth amplification oligomer comprising (a) priming segment $D1_p$ and (b) displacer tag D2 located 5' to $D1_p$. In some such variations, the kit or reaction mixture further includes a seventh amplification oligomer comprising a second displacer priming segment $D2_p$ having a nucleotide sequence substantially corresponding to D2. In other embodiments of the kit or reaction mixture, the second amplification oligomer further comprises a third heterologous displacer tag (D3) located 5' to D2 and, optionally, a third intervening spacer segment (S3) between D2 and D3. In some variations, the kit or reaction mixture further includes an eighth amplification oligomer comprising (a) priming segment $D2_p$ and (b) displacer tag D3 located 5' to $D2_p$. In more particular variations of a kit or reaction mixture comprising a D3 tag, the kit or reaction mixture further includes an eighth amplification oligomer comprising a third displacer priming segment $D3_p$ having a nucleotide sequence substantially corresponding to D3. In some embodiments of a kit or reaction mixture as above, the first amplification oligomer further comprises a fourth heterologous displacer tag (D4) located 5' to T1 and, optionally, a fourth intervening spacer segment (S4) between T1 and D4, and the kit or reaction mixture further includes a tenth amplification oligomer comprising a priming segment $T1_p$ having a nucleotide sequence substantially corresponding to T1 or substantially corresponding to the complement of a target sequence that is within the target region and near or overlapping with the T1 target sequence, and an eleventh amplification oligomer comprising a fourth displacer priming segment $D4_p$ having a nucleotide sequence substantially corresponding to D4. In other embodiments, the first amplification oligomer comprises U2 and further comprises a fourth heterologous displacer tag (D4) located 5' to U2 and, optionally, a fourth intervening spacer segment (S4) between U2 and D4, and the kit or reaction mixture further includes a tenth amplification oligomer comprising a fourth displacer priming segment $D4_p$ having a nucleotide sequence substantially corresponding to D4. In certain variations, the kit or reaction mixture further includes a reverse transcriptase (RT); in some such variations, the kit or reaction mixture further includes an RNA polymerase (e.g., a T7 polymerase), wherein the first amplification oligomer further comprises an RNA polymerase promoter sequence located 5' to T1.

These and other aspects of the invention will become evident upon reference to the following detailed description of the invention and the attached drawings.

DEFINITIONS

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "a," "an," and "the" include plural referents, unless the context clearly indicates otherwise. For example, "a nucleic acid" as used herein is understood to represent one or more nucleic acids. As such, the terms "a" (or "an"), "one or more," and "at least one" can be used interchangeably herein.

The term "nucleic acid" is intended to encompass a singular "nucleic acid" as well as plural "nucleic acids," and refers to any chain of two or more nucleotides, nucleosides, or nucleobases (e.g., deoxyribonucleotides or ribonucleotides) covalently bonded together. Nucleic acids include, but are not limited to, viral genomes, or portions thereof, either DNA or RNA, bacterial genomes, or portions thereof, fungal, plant or animal genomes, or portions thereof, messenger RNA (mRNA), ribosomal RNA (rRNA), transfer RNA (tRNA), plasmid DNA, mitochondrial DNA, or synthetic DNA or RNA. A nucleic acid may be provided in a linear (e.g., mRNA), circular (e.g., plasmid), or branched form, as well as a double stranded or single stranded form. Nucleic acids may include modified bases to alter the function or behavior of the nucleic acid, e.g., addition of a 3'-terminal dideoxynucleotide to block additional nucleotides from being added to the nucleic acid. As used herein, a "sequence" of a nucleic acid refers to the sequence of bases which make up a nucleic acid. The term "polynucleotide" may be used herein to denote a nucleic acid chain. Throughout this application, nucleic acids are designated as having a 5'-terminus and a 3'-terminus. Standard nucleic acids, e.g., DNA and RNA, are typically synthesized "3'-to-5'," i.e., by the addition of nucleotides to the 5'-terminus of a growing nucleic acid.

A "nucleotide" is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me). As used herein, methoxy oligonucleotides containing "T" residues have a methoxy group at the 2' position of the ribose moiety, and a uracil at the base position of the nucleotide.

The term "region," with reference to a nucleic acid, refers to a portion of the nucleic acid where the portion is smaller than the entire nucleic acid.

A "target nucleic acid" is a nucleic acid comprising a "target region" to be amplified. Target nucleic acids may be DNA or RNA as described herein, and may be either single-stranded or double-stranded. The target nucleic acid may include other regions besides the target region which may not be amplified. Typical target nucleic acids include viral genomes, bacterial genomes, fungal genomes, plant genomes, animal genomes, rRNA, tRNA, or mRNA from viruses, bacteria or eukaryotic cells, mitochondrial DNA, or chromosomal DNA.

Target nucleic acids may be isolated from any number of sources based on the purpose of the amplification assay being carried out. Sources of target nucleic acids include, but are not limited to, clinical specimens (e.g., blood, either whole blood or platelets, urine, saliva, feces, semen, or spinal fluid), environmental samples (e.g., water or soil samples), food samples, beverages, industrial samples (e.g., products and process materials, including water), seed stocks, cDNA libraries, or total cellular RNA. By "isolated" it is meant that a sample containing a target nucleic acid is taken from its natural milieu; however, the term does not connote any particular degree of purification. If necessary, target nucleic acids of the present invention are made available for interaction with the various oligonucleotides of the present invention. This may include, for example, cell lysis or cell permeabilization to release the target nucleic acid from cells, which then may be followed by one or more purification steps, such as a series of isolation and wash steps. (See, e.g., U.S. Pat. Nos. 5,786,208 and 6,821,770, each incorporated by reference herein.) This may be particularly important where the sample source or cellular material released into the sample can interfere with the amplification reaction. Methods to prepare target nucleic acids from various sources for amplification are well known to those of ordinary skill in the art. Target nucleic acids of the present invention may be purified to some degree prior to the amplification reactions described herein, but in other cases, the sample is added to the amplification reaction without any further manipulations.

The term "nucleic acid target region" or "target region" refers to a particular nucleotide sequence of the target nucleic acid that is to be amplified. The "target region" includes the complexing sequences to which amplification oligomers and any associated detection probe(s) complex during the processes of the present invention. Unless the context clearly dictates otherwise, where the target nucleic acid is originally single-stranded, the term "target region" will also refer to the sequence complementary to the target region as present in the target nucleic acid; and where the target nucleic acid is originally double-stranded, the term "target region" refers to both the sense (+) and antisense (−) strands. Notwithstanding the above, reference to either a 3'- or 5'-end of a target region is understood to refer to a particular strand of the target region (for example, reference to a target-binding priming segment in terms of its substantial complementarity to a "3'-end of the target region" is understood to mean that the target-binding segment is substantially complementary to the 3'-end a single strand of the target region). The optimal length of a target sequence depends on a number of considerations, for example, the amount of secondary structure, or self-hybridizing regions in the sequence. A target sequence of the present invention may be of any practical length. Determining the optimal length is easily accomplished by those of ordinary skill in the art using routine optimization methods. In typical embodiments, a target region ranges from about 100 nucleotides in length to from about 150 to about 250 nucleotides in length. The optimal or preferred length may vary under different conditions, which can easily be tested by one of ordinary skill in the art.

The term "target sequence" generally refers to a smaller nucleic acid sequence region within a larger nucleic acid sequence (e.g., within a nucleic acid target region) that hybridizes specifically to at least a portion of an amplification oligomer or probe oligomer (e.g., detection probe) by standard base pairing.

In choosing a target region, and particularly in choosing a target sequence within the target region, the skilled artisan will understand that a "unique" sequence should be chosen so as to distinguish between unrelated or closely related target nucleic acids. As will be understood by those of ordinary skill in the art, "unique" sequences are judged from the testing environment. At least the sequences recognized by the target-binding segment of an amplification oligonucleotide and any associated detection probe (as described in more detail elsewhere herein) should be unique in the environment being tested, but need not be unique within the universe of all possible sequences. In some embodiments, it may be desirable to choose a target region or target sequence which is common to a class of organisms, for example, a sequence which is common to all E. coli strains that might be in a sample. In other situations, a very highly specific target region, or a target region having at least a highly specific target sequence recognized by a detection probe, would be chosen so as to distinguish between closely related organisms, for example, between pathogenic and non-pathogenic E. coli.

As used herein, the term "oligonucleotide," "oligo," or "oligomer" is intended to encompass a singular "oligonucleotide" as well as plural "oligonucleotides," and refers to any polymer of two or more of nucleotides, nucleosides, nucleobases or related compounds used as a reagent in the amplification methods of the present invention, as well as subsequent detection methods. The oligonucleotide may be DNA and/or RNA and/or analogs thereof. The term oligonucleotide does not denote any particular function to the reagent; rather, it is used generically to cover all such reagents described herein. An oligonucleotide may serve various different functions. For example, it may function as a primer if it is capable of hybridizing to a complementary strand and can further be extended in the presence of a nucleic acid polymerase; it may provide a promoter if it contains a sequence recognized by an RNA polymerase and allows for transcription; and it may function to prevent hybridization or impede primer extension if appropriately situated and/or modified. Specific oligonucleotides of the present invention are described in more detail below. As used herein, an oligonucleotide can be virtually any length, limited only by its specific function in an amplification reaction or in detecting an amplification product of the amplification reaction.

Oligonucleotides of a defined sequence and chemical structure may be produced by techniques known to those of ordinary skill in the art, such as by chemical or biochemical synthesis, and by in vitro or in vivo expression from recombinant nucleic acid molecules, e.g., bacterial or viral vectors. As intended by this disclosure, an oligonucleotide does not consist solely of wild-type chromosomal DNA or the in vivo transcription products thereof.

Oligonucleotides may be modified in any way, as long as a given modification is compatible with the desired function of a given oligonucleotide. One of ordinary skill in the art can easily determine whether a given modification is suitable or desired for any given oligonucleotide of the present invention. Modifications include base modifications, sugar modifications or backbone modifications. Base modifications include, but are not limited to the use of the following bases in addition to adenine, cytidine, guanosine, thymine and uracil: C-5 propyne, 2-amino adenine, 5-methyl cytidine, inosine, and dP and dK bases. The sugar groups of the nucleoside subunits may be ribose, deoxyribose and analogs thereof, including, for example, ribonucleosides having a 2'-O-methyl (2'-O-ME) substitution to the ribofuranosyl moiety. (See, e.g., U.S. Pat. No. 6,130,038, incorporated by reference herein.) Other sugar modifications include, but are not limited to 2'-amino, 2'-fluoro, (L)-alpha-threofuranosyl, and pentopuranosyl modifications. The nucleoside subunits may be joined by linkages such as phosphodiester linkages, modified linkages or by non-nucleotide moieties which do not prevent hybridization of the oligonucleotide to its complementary target nucleic acid sequence. Modified linkages include those linkages in which a standard phosphodiester linkage is replaced with a different linkage, such as a phosphorothioate linkage or a methylphosphonate linkage. The nucleobase subunits may be joined, for example, by replacing the natural deoxyribose phosphate backbone of DNA with a pseudo peptide backbone, such as a 2-aminoethylglycine backbone which couples the nucleobase subunits by means of a carboxymethyl linker to the central secondary amine. (DNA analogs having a pseudo peptide backbone are commonly referred to as "peptide nucleic acids" or "PNA" and are disclosed in U.S. Pat. No. 5,539,082, incorporated by reference herein.) Other linkage modifications include, but are not limited to, morpholino bonds.

Non-limiting examples of oligonucleotides or oligomers contemplated by the present invention include nucleic acid analogs containing bicyclic and tricyclic nucleoside and nucleotide analogs (LNAs). (See, e.g., U.S. Pat. Nos. 6,268,490 and 6,670,461, each incorporated by reference herein.) Any nucleic acid analog is contemplated by the present invention provided the modified oligonucleotide can perform its intended function, e.g., hybridize to a target nucleic acid under stringent hybridization conditions or amplification conditions, or interact with a DNA or RNA polymerase, thereby initiating extension or transcription. In the case of detection probes, the modified oligonucleotides must also be capable of preferentially hybridizing to the target nucleic acid under stringent hybridization conditions.

While design and sequence of oligonucleotides for the present invention depend on their function as described below, several variables must generally be taken into account. Among the most critical are: length, melting temperature ($T_m$), specificity, complementarity with other oligonucleotides in the system, G/C content, polypyrimidine (T, C) or polypurine (A, G) stretches, and the 3'-end sequence. Controlling for these and other variables is a standard and well-known aspect of oligonucleotide design, and various computer programs are readily available to screen large numbers of potential oligonucleotides for optimal ones.

"Substantially complementary" means that a nucleic acid strand (e.g., a target-binding sequence of an amplification oligomer) is capable of hybridizing to a target nucleic acid strand (e.g., to a target sequence within a nucleic acid target region). "Hybridization" means sufficient hydrogen bonding, which can be, e.g., Watson-Crick, Hoogsteen, or reversed Hoogsteen hydrogen bonding, between complementary nucleoside or nucleotide bases such that stable and specific binding occurs between the nucleic acid strands. Hybridization capability is determined according to amplification conditions or stringent hybridization conditions, including suitable buffer concentrations and temperatures, that allow specific hybridization to a nucleic acid strand having a region of full or partial complementarity. Thus, not all nucleotides of the nucleic acid need by complementary. Further, a nucleic acid strand is "substantially complementary" when it hybridizes to all, part, or an overlapping region of a target nucleic acid. Qualitative and quantitative considerations for establishing amplification conditions or stringent hybridization conditions for the design of oligonucleotides according to the present invention are known in the art. Typically, two nucleic acid regions are substantially complementary when, e.g., at least 90% of the respective bases are complementary, more typically when at least 95% and preferably when 100% of the respective bases are complementary.

A nucleotide sequence of an oligonucleotide "substantially corresponds to" a specified reference nucleic acid sequence if the nucleotide sequence is sufficiently similar to the reference sequence such that the oligonucleotide has similar hybridization properties to the reference nucleic acid sequence in that it would hybridize with the same target nucleic acid sequence under the conditions employed (amplification conditions or stringent hybridization conditions). One skilled in the art will understand that "substantially corresponding oligonucleotides" can vary from a reference sequence and still hybridize to the same target nucleic acid sequence. It is also understood that a first nucleic acid corresponding to a second nucleic acid includes the RNA and DNA thereof and includes the complements thereof, unless the context clearly dictates otherwise. In certain variations of a nucleotide sequence described herein as "substantially corresponding" to a specified reference sequence, the nucleotide sequence is identical to the reference sequence.

The 3'-terminus of an oligonucleotide (or other nucleic acid) can be blocked in a variety of ways using a blocking moiety, as described below. A "blocked" oligonucleotide is not efficiently extended by the addition of nucleotides to its 3'-terminus, by a DNA- or RNA-dependent DNA polymerase, to produce a complementary strand of DNA. As such, a "blocked" oligonucleotide cannot be a "primer."

The term "segment," as used herein with reference to an oligonucleotide (e.g., an amplification oligomer), refers to a discrete polynucleotide that may form all or only a part of the oligonucleotide and which is typically associated with a specific function. Thus, an oligonucleotide may contain one more segments as described herein. For example, an amplification oligomer may include a "target-binding segment," which is capable of hybridizing to a target sequence, and a "displacer tag segment," which provides a displacer priming sequence. In another example, an amplification oligomer may comprise a "priming segment" for priming polymerase-mediated nucleotide extension, and such an oligomer may or may not include additional nucleotides in addition to the priming segment. The term "segment" is also used herein to refer to oligonucleotide segments or their complements that have been incorporated into an amplicon.

Reference herein to two specified segments separated by a forward slash ("/") is a reference to the specified segments in the alternative. Thus, for example, reference to a segment as "D1/D1$_p$," means that the specified segment is either D1 or D1$_p$, depending on the particular context.

A "tagged oligonucleotide" as used herein refers to an oligonucleotide that comprises at least a first region and a second region, where the first region is a "target-binding segment" that hybridizes to the 3'-end of a nucleic acid target region of interest, and where the second region is a "tag segment" situated 5' to the target-binding segment and which does not stably hybridize or bind to a target nucleic acid containing the target region. In accordance with the present invention, the target-binding segment of a tagged oligonucleotide is typically a priming sequence. Thus, the tagged oligonucleotide is typically a "tagged priming oligonucleotide" comprising a tag segment and a target-binding priming segment. In certain aspects, the tagged oligonucleotide is a "tagged promoter oligonucleotide" comprising a tag segment, a target-binding priming segment, and a promoter sequence (or "promoter segment") situated 5' to the tag segment and effective for initiating transcription therefrom. The features and design considerations for a target-binding priming segment are the same as for priming oligonucleotides.

The "tag segment" (also referred to herein as "tag," "heterologous tag," or "heterologous tag segment") may have essentially any heterologous nucleotide sequence provided that it does not stably hybridize to the target nucleic acid sequence of interest and, thereby, participate in detectable amplification. The heterologous tag preferably does not stably hybridize to any sequence derived from the genome of an organism being tested or, more particularly, to any target nucleic acid under reaction conditions. A tag segment that is present in a tagged oligonucleotide is preferably designed so as not to substantially impair or interfere with the ability of the target-binding segment to hybridize to its target sequence. Moreover, the tag segment will be of sufficient length and composition such that once a complement of the tag has been incorporated into an initial DNA primer extension product, a tag-specific priming oligonucleotide can then be used to participate in subsequent rounds of amplification as described herein. A tag segment of the present invention is typically at least 10 nucleotides in length, and may extend up to 15, 20, 25, 30, 35, 40, 50 or more nucleotides in length. Skilled artisans will recognize that the design of tag sequences and tagged oligonucleotides for use in the present invention can follow any of a number of suitable strategies, while still achieving the objectives and advantages described herein.

By "amplification" or "nucleic acid amplification" is meant production of multiple copies of a nucleic acid target region. The multiple copies may be referred to as "amplicons" or "amplification products." An amplicon produced by polymerase-mediated extension from an amplification primer (i.e., an amplification oligomer containing at least a 3' priming segment), when hybridized to a target nucleic acid template, is also be referred to herein as an "extension product." In certain embodiments, the amplified target region contains less than the complete target gene sequence (introns and exons) or an expressed target gene sequence (spliced transcript of exons and flanking untranslated sequences). For example, specific amplicons may be produced by amplifying a portion of the target nucleic acid by using amplification primers that hybridize to, and initiate polymerization from, internal positions of the target nucleic acid. Preferably, the amplified portion contains a detectable target sequence that may be detected using any of a variety of well-known methods.

Many well-known methods of nucleic acid amplification require thermocycling to alternately denature double-stranded nucleic acids and hybridize primers; however, other well-known methods of nucleic acid amplification are isothermal. The polymerase chain reaction (see Mullis et al., U.S. Pat. Nos. 4,683,195, 4,683,202, and 4,800,159, each incorporated by reference herein), commonly referred to as PCR, uses multiple cycles of denaturation, annealing of primer pairs to opposite strands, and primer extension to exponentially increase copy numbers of the target sequence. In a variation called RT-PCR, reverse transcriptase (RT) is used to make a complementary DNA (cDNA) from mRNA, and the cDNA is then amplified by PCR to produce multiple copies of DNA (see Gelfand et al., U.S. Pat. Nos. 5,322,770 and 5,310,652, each incorporated by reference herein). Another method is strand displacement amplification, commonly referred to as SDA, which uses cycles of annealing pairs of primer sequences to opposite strands of a target sequence, primer extension in the presence of a dNTP to produce a duplex hemiphosphorothioated primer extension product, endonuclease-mediated nicking of a hemimodified restriction endonuclease recognition site, and polymerase-mediated primer extension from the 3'-end of the nick to displace an existing strand and produce a strand for the next round of primer annealing, nicking and strand displacement, resulting in geometric amplification of product. (See Walker et al., *Proc. Natl. Acad. Sci. USA* 89:392-396, 1992; Walker et al., *Nucleic Acids Research* 20:1691-1696, 1992; and U.S. Pat. No. 5,455,166; each incorporated by reference herein.) Thermophilic SDA (tSDA) uses thermophilic endonucleases and polymerases at higher temperatures in essentially the same method (see European Pat. No. 0 684 315, incorporated by reference herein). Other amplification methods include: nucleic acid sequence based amplification (see Malek et al., U.S. Pat. No. 5,130,238, incorporated by reference herein), commonly referred to as NASBA; one that uses an RNA replicase to amplify the probe molecule itself (see Lizardi et al., *BioTechnol.* 6:1197-1202, 1988, incorporated by reference herein), commonly referred to as Qβ replicase; a transcription-based amplification method (see Kwoh, et al., *Proc. Natl. Acad. Sci. USA* 86:1173-1177, 1989, incorporated by reference herein); self-sustained sequence replication (see Guatelli et al., *Proc. Natl. Acad. Sci. USA* 87, 1874-1878, 1990; Landgren, *Trends in Genetics* 9:199-202, 1993; and Lee et al., NUCLEIC ACID AMPLIFICATION TECHNOLOGIES (1997); each incorporated by reference herein); and, transcription-mediated amplification (see Kacian et al., U.S. Pat. Nos. 5,480,784 and 5,399,491, each incorporated by reference herein), commonly referred to as TMA. For further discussion of known amplification methods see Persing, David H., "In Vitro Nucleic Acid Amplification Techniques" in *Diagnostic Medical Microbiology: Principles and Applications* (Persing et al. eds., 1993), pp. 51-87, incorporated by reference herein. Other illustrative amplification methods suitable for use in accordance with the present invention include rolling circle amplification (RCA) (see Lizardi, U.S. Pat. No. 5,854,033, incorporated by reference herein); Helicase Dependent Amplification (HDA) (see Kong et al., U.S. Pat. Appln. Pub. No. US 2004-0058378 A1, incorporated by reference herein); and Loop-Mediated Isothermal Amplification (LAMP) (see Notomi et al., U.S. Pat. No. 6,410,278, incorporated by reference herein).

Preferred transcription-based amplification systems of the present invention include TMA, which employs an RNA polymerase to produce multiple RNA transcripts of a target region (see, e.g., Kacian et al., U.S. Pat. Nos. 5,480,784 and 5,399,491; and Becker et al., U.S. Pat. No. 7,374,885; each incorporated by reference herein). TMA uses a "promoter oligonucleotide" or "promoter-primer" that hybridizes to a target nucleic acid in the presence of a reverse transcriptase and an RNA polymerase to form a double-stranded promoter from which the RNA polymerase produces RNA transcripts. These transcripts can become templates for further rounds of TMA in the presence of a second primer capable of hybridizing to the RNA transcripts. Unlike PCR, LCR or other methods that require heat denaturation, TMA is an isothermal method that uses an RNAse H activity to digest the RNA strand of an RNA:DNA hybrid, thereby making the DNA strand available for hybridization with a primer or promoter-primer. Typically, the RNAse H activity associated with the reverse transcriptase provided for amplification is used.

In one illustrative TMA method, one amplification primer is an oligonucleotide promoter-primer that comprises a promoter sequence, which becomes functional when double-stranded, located 5' of a target-binding sequence that is capable of hybridizing to a binding site of a target RNA at a location 3' to the sequence to be amplified. A promoter-primer may be referred to as a "T7-primer" when it is specific for T7 RNA polymerase recognition. Under certain circumstances, the 3'-end of a promoter-primer, or a sub-population of such promoter-primers, may be modified to block or reduce primer extension. From an unmodified promoter-primer, reverse transcriptase creates a cDNA copy of the target RNA, while RNAse H activity degrades the target RNA. A second amplification primer then binds to the cDNA. This primer may be referred to as a "non-T7 primer" to distinguish it from a "T7-primer." From this second amplification primer, reverse transcriptase creates another DNA strand, resulting in a double-stranded DNA with a functional promoter at one end. When double-stranded, the promoter sequence is capable of binding an RNA polymerase to begin transcription of the target sequence to which the promoter-primer is hybridized. An RNA polymerase uses this promoter sequence to produce multiple RNA transcripts (i.e., amplicons), generally about 100 to 1,000 copies. Each newly-synthesized amplicon can anneal with the second amplification primer. Reverse transcriptase can then create a DNA copy, while the RNAse H activity degrades the RNA of this RNA:DNA duplex. The promoter-primer can then bind to the newly synthesized DNA, allowing the reverse transcriptase to create a double-stranded DNA, from which the RNA polymerase produces multiple amplicons. Thus, a billion-fold isothermic amplification can be achieved using two amplification primers.

In another illustrative TMA method, one or more features as described in Becker et al., U.S. Pat. Appln. Pub. No. US 2006-0046265 A1, are optionally incorporated. Preferred TMA methods in this respect include the use of blocking moieties, terminating moieties, and other modifying moieties that provide improved TMA process sensitivity and accuracy. Thus, certain preferred embodiments of the present invention employ tagged oligonucleotides and tag-mediated displacement, as described herein, in conjunction with the methods as described in Becker et al., U.S. Pat. Appln. Pub. No. US 2006-0046265 A1.

By "detectable amplification" is meant that a detectable signal associated with an amplification product in an amplification reaction mixture rises above a predetermined background or threshold level (end-point amplification) or rises above a background or threshold level within a predetermined period of time (real-time amplification). (See, e.g., Light et al., U.S. Pat. Appln. Pub. No. US 2006-0276972, paragraphs 506-549, incorporated by reference herein.) The amplification product contains a sequence having sequence identity with a nucleic acid target region or its complement and can be detected with, for example, an intercalating dye or a detection probe having specificity for a target sequence within the target region or its complement.

"Amplification conditions" means conditions permitting nucleic acid amplification according to the present invention. Amplification conditions may, in some embodiments, be less stringent than "stringent hybridization conditions" as described herein. Oligonucleotides used in the amplification reactions of the present invention hybridize to their intended targets under amplification conditions, but may or may not hybridize under stringent hybridization conditions. On the other hand, detection probes of the present invention hybridize under stringent hybridization conditions. While the Examples section infra provides exemplary amplification conditions for amplifying target nucleic acid sequences according to the present invention, other acceptable conditions to carry out nucleic acid amplifications according to the present invention could be easily ascertained by someone having ordinary skill in the art depending on the particular method of amplification employed.

"Nucleic acid hybridization" is the process by which two nucleic acid strands having completely or partially complementary nucleotide sequences come together under predetermined reaction conditions to form a stable, double-stranded hybrid. Either nucleic acid strand may be a deoxyribonucleic acid (DNA) or a ribonucleic acid (RNA) or analogs thereof. Thus, hybridization can involve RNA:RNA hybrids, DNA:DNA hybrids, RNA:DNA hybrids, or analogs thereof. The two constituent strands of this double-stranded structure, sometimes called a hybrid, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs. Non-canonical base pairing is well-known in the art. (See, e.g., Roger L. P. Adams et al., *The Biochemistry of the Nucleic Acids* (11th ed. 1992), incorporated by reference herein.)

"Stringent hybridization conditions" or "stringent conditions" refer to conditions where a specific detection probe is able to hybridize with target nucleic acids over other nucleic acids present in the test sample. It will be appreciated that these conditions may vary depending upon factors including the GC content and length of the probe, the hybridization temperature, the composition of the hybridization reagent or solution, and the degree of hybridization specificity sought. Stringent hybridization conditions can include, for example, 6×NaCl/sodium citrate (SSC) at about 45° C. for a hybridization step, followed by a wash of 2×SSC at 50° C.; or, alternatively, e.g., hybridization at 42° C. in 5×SSC, 20 mM NaPO4, pH 6.8, 50% formamide, followed by a wash of 0.2×SSC at 42° C.

By "nucleic acid hybrid" or "hybrid" or "duplex" is meant a nucleic acid structure containing a double-stranded, hydrogen-bonded region where each strand is substantially complementary to the other, and where the region is sufficiently stable under amplification conditions or stringent hybridization conditions. Such hybrids may comprise RNA:RNA, RNA:DNA, or DNA:DNA duplex molecules.

By "stable" or "stably hybridize" is meant that the temperature of a reaction mixture is at least 2° C. below the melting temperature of a nucleic acid duplex.

"Target-binding sequence" or "target-binding segment" is used herein to refer to a nucleic acid sequence that is substantially complementary to, and thus configured to hybridize with, a target nucleic acid sequence.

An "amplification oligonucleotide" is an oligonucleotide, at least the 3'-end of which is substantially complementary to a target nucleic acid, and which hybridizes to a target nucleic acid, or its complement, and participates in a nucleic acid amplification reaction. An example of an amplification oligonucleotide is a "primer" or "priming oligonucleotide" that hybridizes to a target nucleic acid and contains a 3' OH end that is extended by a polymerase in an amplification process. Another example of an amplification oligonucleotide is an oligonucleotide that is not extended by a polymerase (e.g., because it has a 3' blocked end) but participates in or facilitates amplification. In some embodiments, the 5' region of an amplification oligonucleotide includes a promoter sequence that is non-complementary to the target nucleic acid (which may be referred to as a "promoter primer" or "promoter provider"). Those skilled in the art will understand that an amplification oligonucleotide that functions as a primer may be modified to include a 5' promoter sequence, and thus function as a "promoter primer." Incorporating a 3' blocked end further modifies the promoter primer, which is now capable of hybridizing to a target nucleic acid and providing an upstream promoter sequence that serves to initiate transcription, but does not provide a primer for oligo extension. Such a modified oligo is referred to herein as a "promoter provider" oligonucleotide. Size ranges for amplification oligonucleotides include those that are about 10 to about 70 nt long (not including any promoter sequence or poly-A tails) and contain at least about 10 contiguous bases, or even at least 12 contiguous bases that are complementary to a region of the target nucleic acid sequence (or a complementary strand thereof). An amplification oligonucleotide may optionally include modified nucleotides or analogs, or additional nucleotides that participate in an amplification reaction but are not complementary to or contained in the target nucleic acid, or template sequence.

As is well known in the art, a "promoter" is a specific nucleic acid sequence that is recognized by a DNA-dependent RNA polymerase ("transcriptase") as a signal to bind to the nucleic acid and begin the transcription of RNA at a specific site. For binding, it was generally thought that such transcriptases required DNA which had been rendered double-stranded in the region comprising the promoter sequence via an extension reaction. It is now known that efficient transcription of RNA can take place even under conditions where a double-stranded promoter is not formed through an extension reaction with the template nucleic acid. The template nucleic acid (the sequence to be transcribed) need not be double-stranded. Individual DNA-dependent RNA polymerases recognize a variety of different promoter sequences, which can vary markedly in their efficiency in promoting transcription. When an RNA polymerase binds to a promoter sequence to initiate transcription, that promoter sequence is not part of the sequence transcribed. Thus, the RNA transcripts produced thereby will not include that sequence.

A "promoter provider" is an amplification oligonucleotide comprising first and second regions, and which is preferably modified to prevent the initiation of DNA synthesis from its 3'-terminus. The first region of a promoter oligonucleotide is a "target-binding segment" having a base sequence that hybridizes to a DNA template, where the target-binding segment is situated 3', but not necessarily adjacent to, a promoter region. The hybridizing portion of a promoter oligonucleotide is typically at least 10 nucleotides in length, and may extend up to 15, 20, 25, 30, 35, 40, 50 or more nucleotides in length. The second region is a "promoter segment" comprising a promoter for an RNA polymerase. A promoter provider oligonucleotide is engineered so that it is incapable of being extended by an RNA- or DNA-dependent DNA polymerase, e.g., reverse transcriptase, preferably comprising a blocking moiety at its 3'-terminus as described herein.

A "priming oligonucleotide" is an oligonucleotide, at least the 3'-end of which is complementary to a nucleic acid template, and which complexes (by hydrogen bonding or hybridization) with the template to give a primer:template complex suitable for initiation of synthesis by an RNA- or DNA-dependent DNA polymerase. The at least 3'-end of the priming oligonucleotide that is complementary to the nucleic acid template is also referred to herein a "priming sequence" or "priming segment" and in certain variations a priming oligonucleotide may include additional nucleotide(s) 5' to the priming sequence that do not stably hybridize with the target nucleic acid. A priming oligonucleotide is extended by the addition of covalently bonded nucleotide bases to its 3'-terminus, which bases are complementary to the template. The result is a primer extension product. A priming oligonucleotide of the present invention is typically at least 10 nucleotides in length, and may extend up to 15, 20, 25, 30, 35, 40, 50 or more nucleotides in length. Suitable and preferred priming oligonucleotides are described herein. Virtually all DNA polymerases (including reverse transcriptases) that are known require complexing of an oligonucleotide to a single-stranded template ("priming") to initiate DNA synthesis, whereas RNA replication and transcription (copying of RNA from DNA) generally do not require a primer. By its very nature of being extended by a DNA polymerase, a priming oligonucleotide does not comprise a 3'-blocking moiety.

A "displacer oligonucleotide" is a priming oligonucleotide comprising a "displacer priming sequence" (also referred to herein as a "displacer priming segment") that hybridizes to a template nucleic acid upstream from a neighboring priming oligonucleotide hybridized to the 3'-end of a target sequence (referred to herein as the "forward priming oligonucleotide"). By "upstream" is meant that a 3'-end of the displacer oligonucleotide complexes with the template nucleic acid 5' to a 3'-end of the forward priming oligonucleotide. When hybridized to the template nucleic acid, the 3'-terminal base of the displacer oligonucleotide is preferably adjacent to or spaced from the 5-terminal base of the forward priming oligonucleotide. More preferably, the 3'-terminal base of the displacer oligonucleotide is spaced from 5 to 35 bases from the 5'-terminal base of the forward priming oligonucleotide. The displacer oligonucleotide may be provided to a reaction mixture contemporaneously with the forward priming oligonucleotide or after the forward priming oligonucleotide has had sufficient time to hybridize to the template nucleic acid. Extension of the forward priming oligonucleotide can be initiated prior to or after the displacer oligonucleotide is provided to a reaction mixture. Under amplification conditions, the displacer oligonucleotide is extended in a template-dependent manner, thereby displacing a primer extension product comprising the forward priming oligonucleotide that is complexed with the template nucleic acid. Once displaced from the template nucleic acid, the primer extension product comprising the forward priming oligonucleotide is available for complexing with another amplification oligomer. The forward priming oligonucleotide and the displacer oligonucleotide both preferentially hybridize to the target nucleic acid. Examples of displacer oligonucleotides and their uses are disclosed by Becker et al., U.S. Pat. No. 7,713,697, incorporated by reference herein.

A "displacer tag" or "heterologous displacer tag" as used herein refers to a tag segment having a nucleotide sequence that substantially corresponds to a displacer priming sequence of a displacer oligonucleotide, such that once a complement of the displacer tag has been incorporated into an oligonucleotide primer extension product, the displacer oligonucleotide can then be used to participate in subsequent rounds of amplification as described herein. Typically, the displacer tag sequence is the same as the displacer priming sequence.

A "universal priming oligonucleotide" is a priming oligonucleotide comprising a "universal priming sequence" (also referred to herein as a "universal priming segment") that does not specifically hybridize to a nucleic acid target region, but instead hybridizes to a sequence that is the complement of a heterologous tag (a "universal tag"), such that once a complement of the universal tag has been incorporated into an oligonucleotide primer extension product, the universal priming oligonucleotide can then be used to participate in subsequent rounds of amplification as described herein. Accordingly, a "universal tag" or "heterologous universal tag" as used herein refers to a tag segment having a nucleotide sequence that substantially corresponds to a universal priming sequence of a universal priming oligonucleotide. Typically, the universal tag sequence is the same as the universal priming sequence. A universal tag is typically situated 3' to a displacer tag.

As used herein, a "spacer segment" or "intervening spacer segment" is a nucleotide sequence positioned between and adjacent to two other segments of an oligonucleotide and which is not a target-binding sequence, a sequence substantially corresponding to a priming sequence, or a promoter sequence. Spacer segments are typically 1 to 20 nucleotides in length, more typically 3 to 18 nucleotides in length, and most typically 3 to 12 nucleotides in length, including all whole numbers therebetween. In some aspects, the inclusion of spacer segments in amplification oligomers comprising a displacer tag (e.g., between a target-binding segment and a displacer tag) can improve displacement activity. In other aspects, the inclusion of spacer segments in promoter oligonucleotides (e.g., between a target-binding segment and an RNA polymerase promoter sequence) increases the rate at which RNA amplification products are formed.

As used herein, a "blocking moiety" is a substance used to "block" the 3'-terminus of an oligonucleotide or other nucleic acid so that it cannot be efficiently extended by a nucleic acid polymerase. A blocking moiety may be a small molecule, e.g., a phosphate or ammonium group, or it may be a modified nucleotide, e.g., a 3'2' dideoxynucleotide or 3' deoxyadenosine 5'-triphosphate (cordycepin), or other modified nucleotide. Additional blocking moieties include, for example, the use of a nucleotide or a short nucleotide sequence having a 3'-to-5' orientation, so that there is no free hydroxyl group at the 3'-terminus, the use of a 3' alkyl group, a 3' non-nucleotide moiety (see, e.g., Arnold et al., U.S. Pat. No. 6,031,091, incorporated by reference herein), phosphorothioate, alkane-diol residues, peptide nucleic acid (PNA), nucleotide residues lacking a 3' hydroxyl group at the 3'-terminus, or a nucleic acid binding protein. Preferably, the 3'-blocking moiety comprises a nucleotide or a nucleotide sequence having a 3'-to-5' orientation or a 3' non-nucleotide moiety, and not a 3'2'-dideoxynucleotide or a 3' terminus having a free hydroxyl group. Additional methods to prepare 3'-blocking oligonucleotides are well-known to those of ordinary skill in the art.

A "terminating oligonucleotide" is an oligonucleotide comprising a base sequence that is complementary to a region of the target nucleic acid in the vicinity of the 5'-end of the target sequence, so as to "terminate" primer extension of a nascent nucleic acid that includes a priming oligonucleotide, thereby providing a defined 3'-end for the nascent nucleic acid strand. A terminating oligonucleotide is designed to hybridize to the target nucleic acid at a position sufficient to achieve the desired 3'-end for the nascent nucleic acid strand. The positioning of the terminating oligonucleotide is flexible depending upon its design. A terminating oligonucleotide may be modified or unmodified. In certain embodiments, terminating oligonucleotides are synthesized with at least one or more 2'-O-ME ribonucleotides. These modified nucleotides have demonstrated higher thermal stability of complementary duplexes. The 2'-O-ME ribonucleotides also function to increase the resistance of oligonucleotides to exonucleases, thereby increasing the half-life of the modified oligonucleotides. (See, e.g., Majlessi et al., *Nucleic Acids Res.* 26:2224-9, 1988, incorporated by reference herein.) Other modifications as described elsewhere herein may be utilized in addition to or in place of 2'-O-ME ribonucleotides. For example, a terminating oligonucleotide may comprise PNA or an LNA. (See, e.g., Petersen et al., *J. Mol. Recognit.* 13:44-53, 2000, incorporated by reference herein.) A terminating oligonucleotide of the present invention typically includes a blocking moiety at its 3'-terminus to prevent extension. A terminating oligonucleotide may also comprise a protein or peptide joined to the oligonucleotide so as to terminate further extension of a nascent nucleic acid chain by a polymerase. A terminating oligonucleotide of the present invention is typically at least 10 bases in length, and may extend up to 15, 20, 25, 30, 35, 40, 50 or more nucleotides in length. Suitable and preferred terminating oligonucleotides are described herein. While a terminating oligonucleotide typically or necessarily includes a 3'-blocking moiety, "3'-blocked" oligonucleotides are not necessarily terminating oligonucleotides. Other oligonucleotides of the present invention, e.g., promoter oligonucleotides and capping oligonucleotides are typically or necessarily 3'-blocked as well.

"Detection probe" refers to an oligonucleotide comprising a target-binding segment that hybridizes specifically to a target sequence contained within a nucleic acid target region under conditions that promote hybridization to allow detection of a target nucleic acid comprising the target region, or an amplified nucleic acid comprising the target region. Detection may either be direct (e.g., a probe hybridized directly to its target sequence) or indirect (e.g., a probe linked to its target via an intermediate molecular structure). Detection probes may be DNA, RNA, analogs thereof or combinations thereof and they may be labeled or unlabeled. Detection probes may further include alternative backbone linkages such as, e.g., 2'-O-methyl linkages. A detection probe may comprise target-specific sequences and other sequences that contribute to the three-dimensional conformation of the probe (see, e.g., U.S. Pat. Nos. 5,118,801; 5,312,728; 6,849,412; 6,835,542; 6,534,274; and 6,361,945; and US Patent Application Pub. No. 20060068417; each incorporated by reference herein).

As used herein, a "label" refers to a moiety or compound joined directly or indirectly to a probe that is detected or leads to a detectable signal. Direct labeling can occur through bonds or interactions that link the label to the probe, including covalent bonds or non-covalent interactions, e.g., hydrogen bonds, hydrophobic and ionic interactions, or formation of chelates or coordination complexes. Indirect labeling can occur through use of a bridging moiety or "linker" such as a binding pair member, an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay in which bound labeled probe in a mixture exhibits a detectable change different from that of an unbound labeled probe, e.g., instability or differential degradation properties. A "homogeneous detectable label" can be detected without physically removing bound from unbound forms of the label or labeled probe (see, e.g., U.S. Pat. Nos. 5,283,174; 5,656,207; and 5,658,737; each incorporated by reference herein). Labels include chemiluminescent compounds, e.g., acridinium ester ("AE") compounds that include standard AE and derivatives (see, e.g., U.S. Pat. Nos. 5,656,207; 5,658,737; and 5,639,604; each incorporated by reference herein). Synthesis and methods of attaching labels to nucleic acids and detecting labels are well known. (See, e.g., Sambrook et al., *Molecular Cloning, A Laboratory Manual,* 2nd ed. (Cold Spring Harbor Laboratory Press, Cold Spring Harbor, N.Y., 1989), Chapter 10, incorporated by reference herein. See also U.S. Pat. Nos. 5,658,737; 5,656,207; 5,547,842; 5,283,174; and 4,581,333; each incorporated by reference herein). More than one label, and more than one type of label, may be present on a particular probe, or detection may use a mixture of probes in which each probe is labeled with a compound that produces a detectable signal (see, e.g., U.S. Pat. Nos. 6,180,340 and 6,350,579, each incorporated by reference herein).

"Capture probe" or "capture oligomer" refers to an oligonucleotide comprising a target-binding segment that hybridizes specifically to a target sequence in a target nucleic acid and a moiety that joins to a binding partner on an immobilized probe to capture the target nucleic acid to a support. One example of a capture probe includes two binding regions: the target-binding segment and an immobilized probe-binding region, usually on the same oligomer, although the two regions may be present on two different oligomers joined together by one or more linkers. Another embodiment of a capture oligomer uses a target-binding segment that includes random or non-random poly-GU, poly-GT, or poly U sequences to bind non-specifically to a target nucleic acid and link it to an immobilized probe on a support.

"Immobilized oligonucleotide" or "immobilized probe" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligonucleotide joined to a support that facilitates separation of bound target nucleic acid from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size±5%), to which an immobilized probe is joined directly (via covalent linkage, chelation, or ionic interaction), or indirectly (via one or more linkers), where the linkage or interaction between the probe and support is stable during hybridization conditions.

"Sample preparation" refers to any steps or method that treats a sample for subsequent amplification and/or detection of target nucleic acids present in the sample. Samples may be complex mixtures of components of which the target nucleic acid is a minority component. Sample preparation may include any known method of concentrating components, such as microbes or nucleic acids, from a larger sample volume, such as by filtration of airborne or waterborne particles from a larger volume sample or by isolation of microbes from a sample by using standard microbiology methods. Sample preparation may include physical disruption and/or chemical lysis of cellular components to release intracellular components into a substantially aqueous or organic phase and removal of debris, such as by using filtration, centrifugation or adsorption. Sample preparation may include use of a nucleic acid oligonucleotide that selectively or non-specifically capture a target nucleic acid and separate it from other sample components (e.g., as described in U.S. Pat. No. 6,110,678 and International Patent Application Pub. No. WO 2008/016988, each incorporated by reference herein).

"Separating" or "purifying" means that one or more components of a sample are removed or separated from other sample components. Sample components include target nucleic acids usually in a generally aqueous solution phase, which may also include cellular fragments, proteins, carbohydrates, lipids, and other nucleic acids. Separating or purifying removes at least 70%, or at least 80%, or at least 95% of the target nucleic acid from other sample components.

The term "specificity," in the context of an amplification and/or detection system, is used herein to refer to the characteristic of the system which describes its ability to distinguish between target and non-target nucleic acids dependent on sequence and assay conditions. In terms of nucleic acid amplification, specificity generally refers to the ratio of the number of specific amplicons produced to the number of side-products (e.g., the signal-to-noise ratio). In terms of detection, specificity generally refers to the ratio of signal produced from target nucleic acids to signal produced from non-target nucleic acids.

The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, e.g., the ratio of specific amplicons to side-products.

As used herein, the term "relative light unit" ("RLU") is an arbitrary unit of measurement indicating the relative number of photons emitted by the sample at a given wavelength or band of wavelengths. RLU varies with the characteristics of the detection means used for the measurement.

DETAILED DESCRIPTION OF THE INVENTION

Figure 1A:
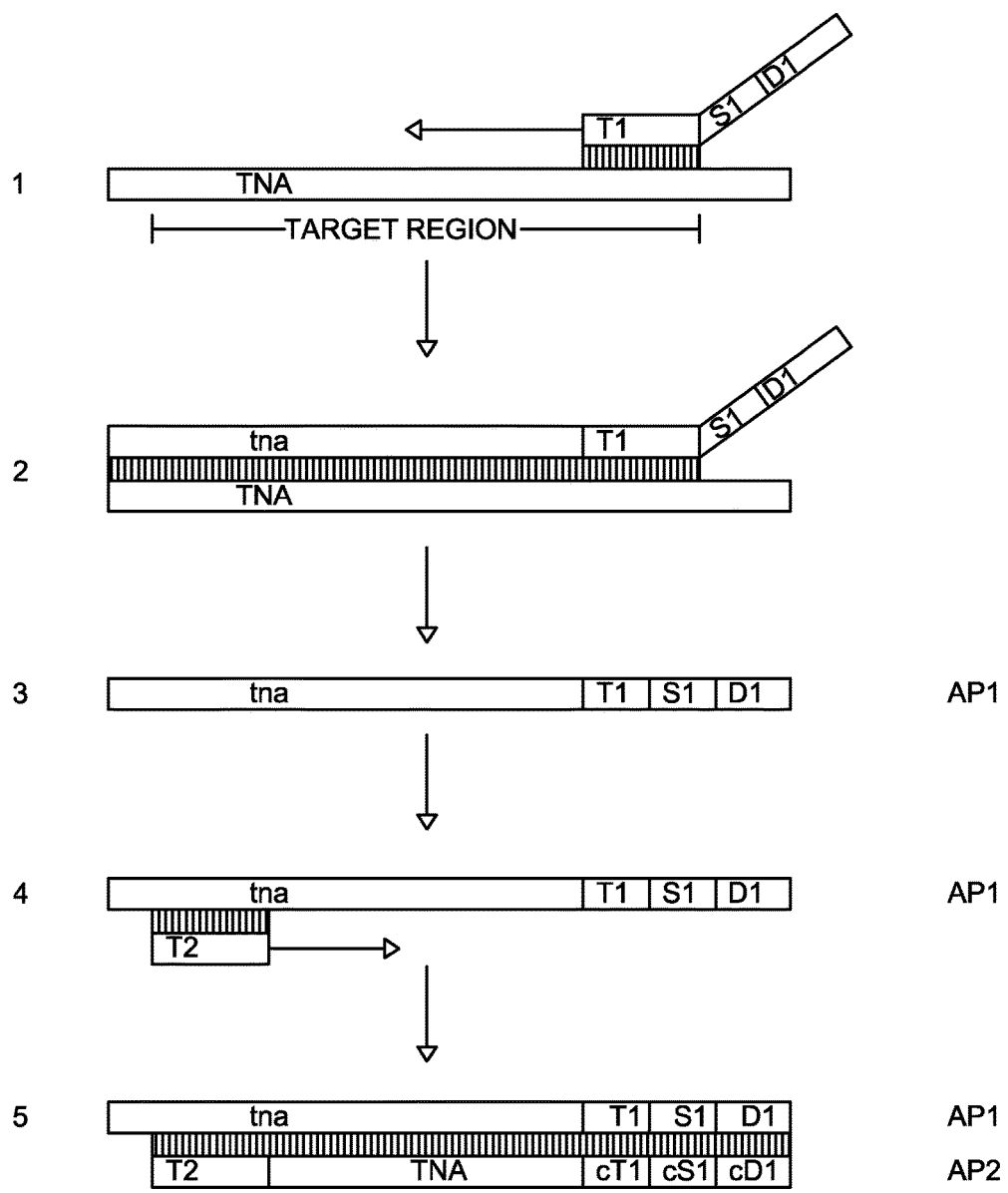
FIGS. 1A and 1B depict the steps of a tag-mediated displacement amplification reaction utilizing a first heterologous displacer tag. TNA: initial target nucleic acid or non-primer, amplicon portion thereof in +polarity; T1: target-binding priming segment; D1: first heterologous displacer tag segment; S1: first intervening spacer segment; tna: non-primer, amplicon portion of target nucleic acid in −polarity; T2: priming segment substantially corresponding to 2nd amplicon; c[X]: amplicon regions complementary to segment [X]; $T1_p$: priming segment substantially corresponding to T1; $D1_p$: priming segment substantially corresponding to D1; AP[#]: amplification product.

The present invention provides methods, kits, and reaction mixtures for amplification of nucleic acids using a tag-mediated displacement strategy. An amplification oligonucleotide is equipped with a heterologous displacer tag situated 5' to a target-binding segment and having a sequence that substantially corresponds to the priming sequence of a displacer oligonucleotide. In this manner, once the complement of the displacer tag has been incorporated into an amplification product, thereby providing a displacer priming site, the displacer oligonucleotide can participate in subsequent rounds of amplification for displacement of an extension product primed from a site within the amplification product 5' to the displacer priming site, thereby increasing overall amplification output and increasing assay kinetics and sensitivity.

This strategy can be used to improve the kinetics of amplification reactions as well as amplification capacity. For example, an amplification oligomer can be designed to include one or more additional displacer tags, each situated in succession 5' to the initial displacer tag. Additional displacer oligomers may then be included in the amp reaction, each corresponding to at least one additional tag and designed to bind an amplicon at a site 3' to at least one other displacer oligomer. Using multiple displacer tags and oligomers in this manner, additional amplification products can be efficiently produced in each round of the amp reaction, thereby increasing overall amplification output and increasing assay kinetics and sensitivity.

Tag-mediated displacement as described herein is also advantageous, for example, when using heterologous tags to introduce universal priming sites. A non-target-specific "universal" priming site can be incorporated into an amplification product using an amplification oligomer equipped with a universal tag substantially corresponding to the universal tag and located 5' to an initial target-specific priming segment. Once a complement of the universal tag has been incorporated into an amplification product, a universal priming oligonucleotide can be used to participate in subsequent rounds of amplification. Such a scenario would preclude the use of known displacement methods, which rely on the use of target-specific displacer priming sites. Using, however, a tag-mediated displacement strategy, a heterologous displacer tag can be incorporated into an amplification oligomer at a site 5' to the universal tag, such that the amplification product comprising the universal priming site further comprises a 3' displacer priming site, thereby allowing the use of a displacer oligomer in subsequent amplification. Not only will extension of a universal primer from the universal priming site be displaced, but extension of the displacer oligomer will produce an additional amplification product, thereby increasing overall amplification output and increasing assay kinetics and sensitivity.

The present invention can be adapted for use in essentially any amplification procedure requiring a template-binding priming oligonucleotide capable of extension in the presence of a nucleic acid polymerase. Incorporation of heterologous displacer tags into such amplification procedures can be achieved without substantially modifying the reagents and reaction conditions of such procedures. Any needed modifications would be well within the knowledge and capabilities of a skilled molecular biologist in view of the instant description. Descriptions of various amplification procedures adopting tag-mediated displacement are further provided herein.

Figure 1B:
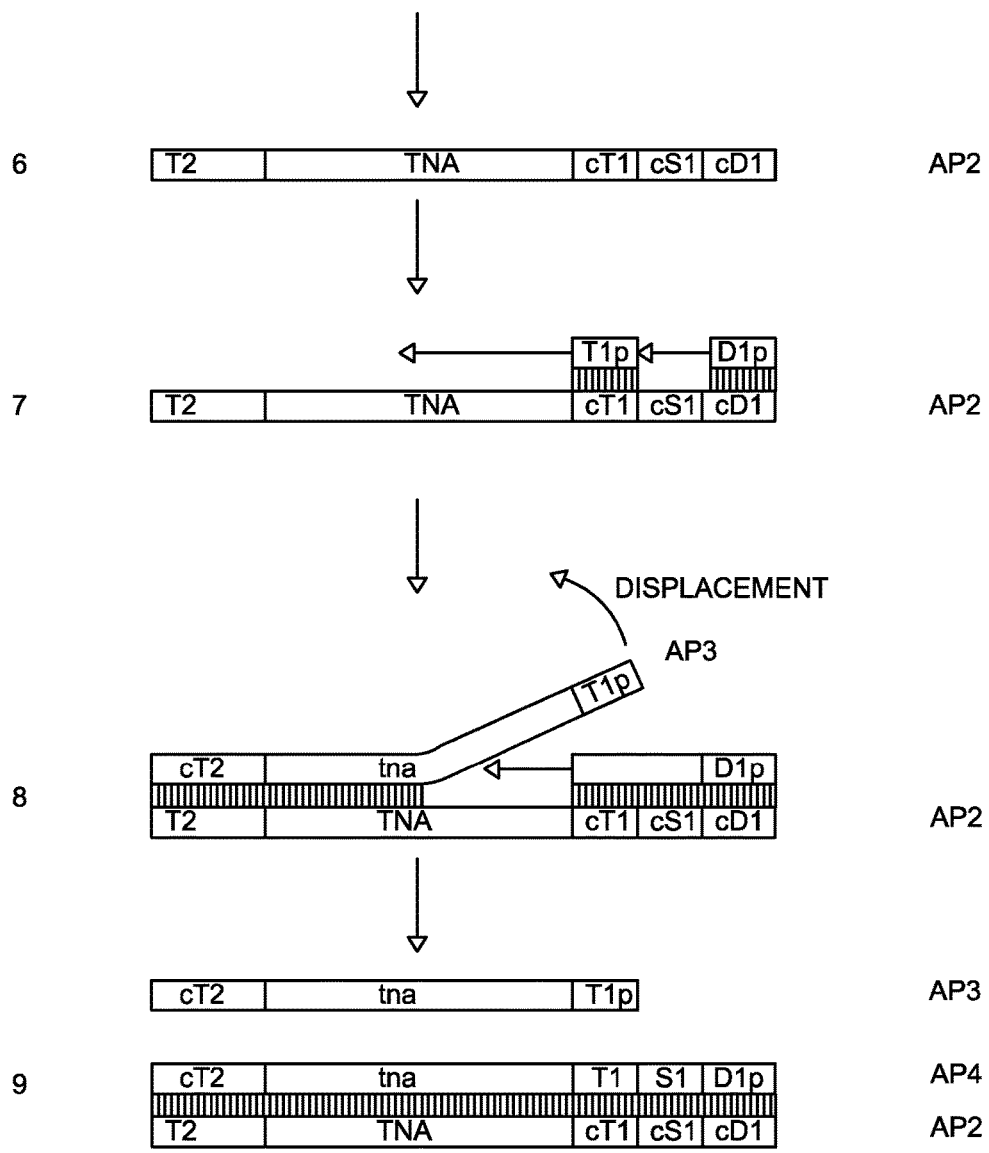

FIGS. 1A and 1B illustrate one embodiment of the nucleic acid amplification method utilizing tag-mediated displacement. Step 1 shows a first amplification oligonucleotide comprising a target-binding priming segment (T1) and a heterologous displacer tag (D1) located 5' to T1. The first amplification oligonucleotide further includes an optional intervening spacer segment (S1) between T1 and D1. The target-binding priming segment hybridizes to a target nucleic acid (TNA) at a 3'-end of a target region. An extension reaction is initiated from the 3'-end of the hybridized, tagged oligonucleotide with a DNA polymerase to produce a first amplicon comprising the displacer tag D1 and a region complementary to the target nucleic acid (tna). See FIG. 1A, Steps 1 and 2. The first amplicon is separated from the target nucleic acid (see Step 3), and a second amplification oligonucleotide comprising a target-binding segment T2, substantially complementary to the complement of a 5'-end of the target region, hybridizes to the first extension product (see Step 4). An amplification reaction (e.g., an extension reaction, as indicated in the Figure) is initiated from the second amplification oligomer to produce a second amplicon comprising segments cT1 and cD1, respectively complementary to T1 and D1. See FIG. 1A, Steps 4 to 6. A third amplification oligomer comprising priming segment $T1_p$, having a sequence substantially corresponding to T1, then hybridizes to the second amplicon to form a $T1_p$:cT1 duplex. See id., Steps 6 and 7. In addition, a fourth oligonucleotide primer comprising a displacer priming segment $D1_p$, having a sequence substantially corresponding to D1, hybridizes to the second amplicon upstream from $T1_p$ to form a $D1_p$:cD1 duplex, and extension reactions are initiated from both $T1_p$ and $D1_p$. See id., Step 7. Extension of the third amplification oligomer produces a third amplicon, which is displaced from the second amplicon as the fourth amplification oligomer is extended. See FIG. 1B, Step 8. Full extension of the fourth amplification oligomer produces a fourth amplicon and results in complete separation of the third amplicon from its template, thereby making the third amplicon available for further rounds of amplification. See id., Step 9.

Figure 2A:
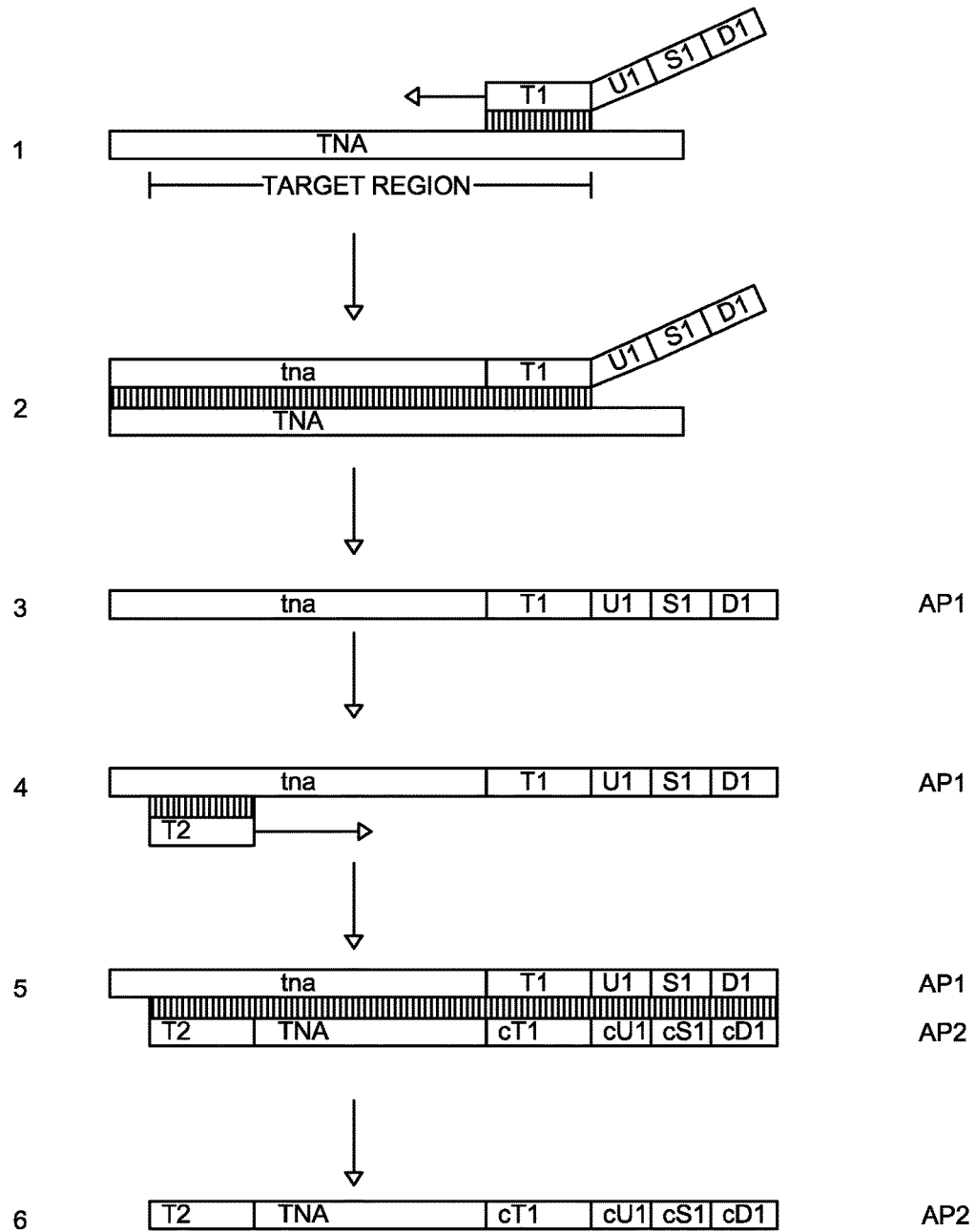
FIGS. 2A and 2B depict the steps of a tag-mediated displacement amplification reaction utilizing a first heterologous displacer tag together with a heterologous universal tag. TNA: initial target nucleic acid or non-primer, amplicon portion thereof in +polarity; T1: target-binding priming segment; U1: heterologous universal tag segment; D1: first heterologous displacer tag segment; S1: first intervening spacer segment; tna: non-primer, amplicon portion of target nucleic acid in −polarity; T2: priming segment substantially corresponding to 2nd amplicon; c[X]: amplicon regions complementary to segment [X]; $U1_p$: priming segment substantially corresponding to U1; $D1_p$: priming segment substantially corresponding to D1; AP[#]: amplification product.
Figure 2B:
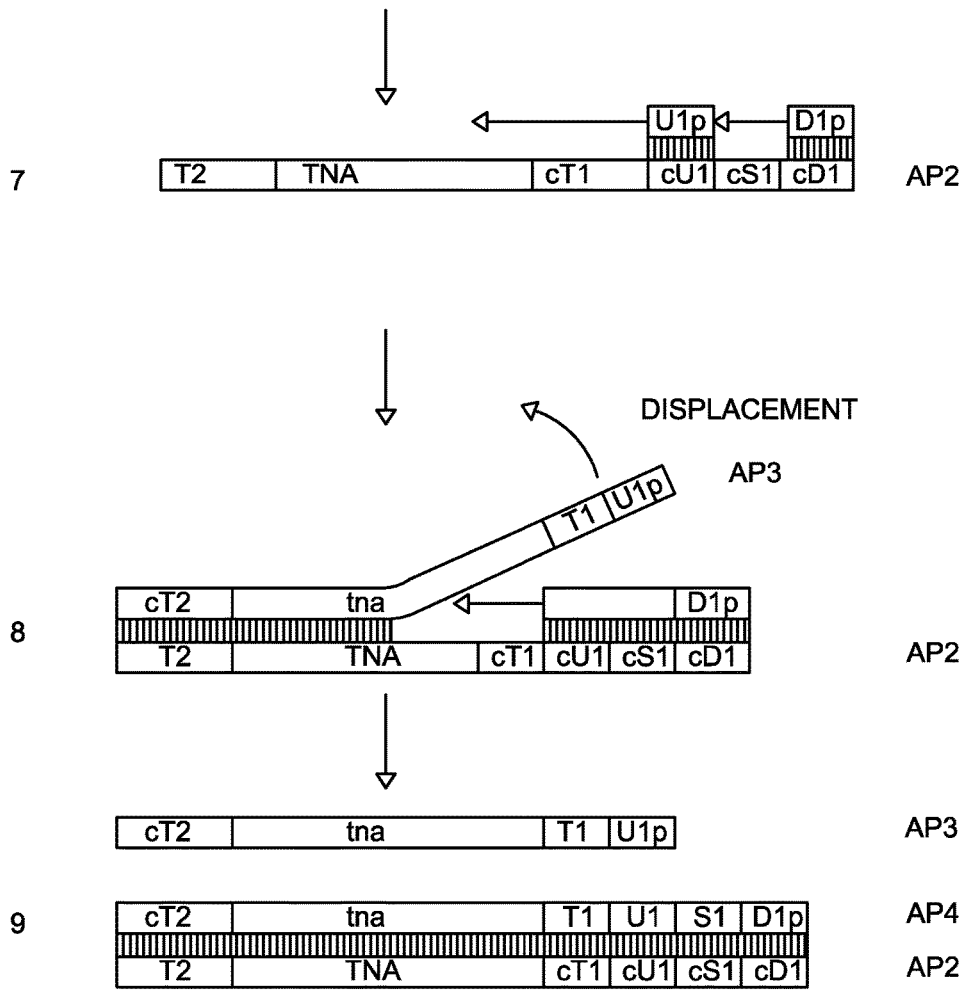

FIGS. 2A and 2B illustrate an embodiment utilizing a universal tag, together with the displacer tag, to incorporate a universal priming site in an amplification product. In this embodiment, the first amplification oligomer from FIG. 1A further includes a heterologous universal tag (U1) situated 5' to the target-binding priming segment T1 and 3' to both the heterologous displacer tag D1 and optional spacer segment S1. See FIG. 2A, Step 1. Steps 1 to 4 parallel those shown in FIG. 1A, whereby a first amplicon is initiated from priming segment T1 hybridized to the target nucleic acid, and a second amplicon is initiated from a second amplification oligomer T2 hybridized to the first amplicon. Amplification from the second oligomer produces a second amplicon comprising segments cU1 and cD1, respectively complementary to U1 and D1. See id., Step 5 and 6. A third amplification oligomer comprising universal priming segment $U1_p$, having a sequence substantially corresponding to U1, then hybridizes to the second amplicon to form a $U1_p$:cU1 duplex. See id., Step 7. In addition, a fourth oligonucleotide primer comprising displacer priming segment $D1_p$ hybridizes to the second extension product upstream from $U1_p$ to form a $U1_p$:cU1 duplex, and extension reactions are initiated from both $U1_p$ and $U1_p$. See id., Step 7. Steps 8 and 9 (FIG. 2B) illustrate a displacement reaction parallel to that shown in FIG. 1B. Specifically, extension of the third amplification oligomer produces a third amplicon, which is displaced from the second amplicon as the fourth amplification oligomer is extended. See FIG. 2B, Step 8. Full extension of the fourth amplification oligomer produces a fourth amplicon and results in complete separation of the third amplicon from its template, thereby making the third amplicon available for further rounds of amplification. See id., Step 9. As also illustrated in this figure, once the universal tag and its complement, cU1, are incorporated into the amplification products, amplification can utilize cU1 as a universal priming site instead of a target-specific priming site. Any variation of the methods described can be similarly modified to incorporate the use of universal priming sites and primers following initial amplification of a target nucleic acid.

Figure 3A:
FIGS. 3A and 3B depict the use of a second heterologous displacer tag in the amplification reaction of FIGS. 1A and 1B. TNA: initial target nucleic acid or non-primer, amplicon portion thereof in +polarity; T1: target-binding priming segment; D1: first heterologous displacer tag segment; S1: first intervening spacer segment; D2: second heterologous displacer segment; S2: second intervening spacer segment; tna: non-primer, amplicon portion of target nucleic acid in −polarity; T2: priming segment substantially corresponding to 2nd amplicon; c[X]: amplicon regions complementary to segment [X]; T1$_p$: priming segment substantially corresponding to T1; D1$_p$: priming segment substantially corresponding to D1; D2$_p$: priming segment substantially corresponding to D1; AO1: first amplification oligonucleotide; AP[#]: amplification product.
Figure 3A:
Figure 3B:
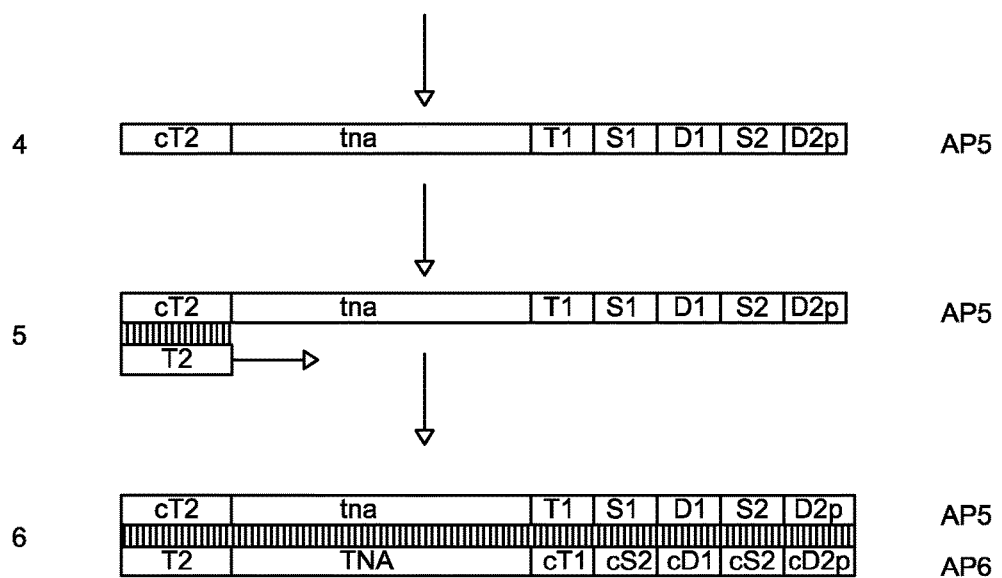

In certain embodiments of the method, multiple displacer tags are incorporated in a tagged oligonucleotide. For example, FIGS. 3A and 3B illustrate an embodiment in which the first amplification oligomer from FIG. 1A further includes a second heterologous displacer tag D2 situated 5' to D1, with an optional second spacer segment S2 situated between D1 and D2. See FIG. 3A, First Amp Oligo. Using this modified first oligomer in Steps 1 through 6 of FIG. 1A results in a second amplicon further comprising segment cD2, complementary to D2, located 3' to cD1. See FIG. 3A, EP2. Referring to Step 1 of FIG. 3A, in addition to hybridization of the third and fourth amplification oligomers (comprising $T1_p$ and $D1_p$, respectively) to the second amplicon, a fifth amplification oligomer comprising a second displacer priming segment $D2_p$, having a sequence substantially corresponding to D2, hybridizes to the second amplicon upstream from $D1_p$ to form a $D2_p$:cD2 duplex, and extension reactions are initiated from each of $T1_p$, $D1_p$, and $D2_p$. See id., Step 1. Extension of the third amplification oligomer from $T1_p$ produces a third amplicon, which is displaced from the second amplicon template as the fourth amplification oligomer is extended from $D1_p$. See FIG. 3A, Step 2. Similarly, the fourth amplicon, produced by extension of the fourth amplification oligomer, is displaced from the template as the fifth amplification oligomer is extended from $D2_p$. See id. Production of the fourth amplicon results in complete separation of the third amplicon from the template strand, while full extension of the fifth amplification oligomer produces a fifth amplicon, resulting in complete separation of the fourth amplicon from its template, thereby making both the third and fourth amplicons available for further rounds of amplification. See id., Step 3. The fifth amplicon then serves as a template for amplification from the second amplification oligomer comprising segment T2, thereby producing a sixth amplicon comprising segments cT1, cD1 and $cD2_p$ (see Steps 5 and 6), which can serve as a template for further amplification (e.g., using one or more of oligomers comprising $T1_p$, $D1_p$, or $D2_p$).

In other embodiments, an additional displacer oligonucleotide comprising a second heterologous displacer tag is added to the reaction to further increase amplification capacity. For example, in some variations, an amplification oligonucleotide comprising displacer priming segment $D1_p$ and displacer tag D2, situated 5' to $D1_p$, may be added to an amplification reaction as depicted in FIGS. 3A and 3B. Such an oligomer is particularly useful, e.g., for further amplification of an amplicon comprising displacer priming site cD1 (or $cD1_p$) while also incorporating a second displacer priming site corresponding to D2. For example, referring to FIG. 4, AP7 represents a seventh amplicon comprising $cD1_p$, but not cD2, which can be produced by amplification from oligomer T2 hybridized to the fourth amplicon (AP4) of FIG. 3A. An amplification oligomer comprising priming segment $D1_p$, an optional spacer segment S2, and displacer tag D2 hybridizes to the seventh extension product to form a $D1_p$:$cD1_p$ duplex, and extension of the amplification oligomer produces an eighth amplicon. See FIG. 4, Steps 1 and 2. The eighth extension product then serves as a template for amplification from the second amplification oligomer, comprising segment T2, to produce a ninth amplicon comprising cD2 in addition to cT1 and $cD1_p$. See id., Steps 3 and 4. This ninth amplicon may then be used as a template for, e.g., extension of a $D2_p$ displacer priming segment (in addition or alternatively to extension from $T1_p$ and/or $D1_p$).

In certain variations, an additional displacer oligonucleotide comprising displacer priming segment $D1_p$ and a second displacer tag D2, as described above, is used in conjunction with an initial amplification oligomer comprising priming segment T1 and both displacer tags D1 and D2. In such variations, the $D1_p$-D2 oligomer may increase the generation of amplicons comprising the D2 tag. For example, as indicated above, the $D1_p$-D2 can prime from amplicons comprising a $cD1_p$ priming site but lacking cD2 (in addition to the capability of priming from amplicons comprising both $cD1/cD1_p$ and cD2).

Alternatively, a displacer oligomer comprising $D1_p$ and D2 is used together with an initial amplification oligomer that includes priming segment T1 and displacer tag D1 in the absence of D2. In such variations, the $D1_p$-D2 oligomer is also useful for the initial incorporation of the D2 tag into an amplification product. For example, the $D1_p$-D2 oligomer may utilize an amplicon such as that shown in Step 6 of FIG. 1A (AP2) as a template for extension from a $D1_p$:cD1 duplex to produce an amplicon incorporating the D2 displacer tag. This amplicon may then serve as a template for primer extension to produce a complementary amplicon incorporating a cD2 displacer priming site.

Figure 5:
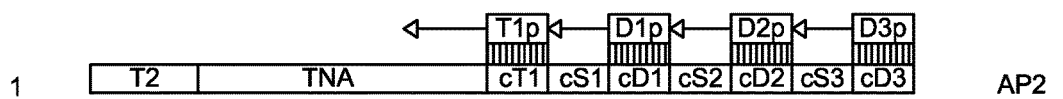
FIG. 5 depicts the use of a third heterologous displacer tag in the amplification reaction of FIGS. 1A and 1B. TNA: initial target nucleic acid or non-primer, amplicon portion thereof in +polarity; T1: target-binding priming segment; D1: first heterologous displacer tag segment; S1: first intervening spacer segment; D2: second heterologous displacer segment; S2: second intervening spacer segment; D3: third heterologous displacer segment; S3: third intervening spacer segment; tna: non-primer, amplicon portion of target nucleic acid in –polarity; T2: priming segment substantially corresponding to 2nd amplicon; c[X]: amplicon regions complementary to segment [X]; T1$_p$: priming segment substantially corresponding to T1; D1$_p$: priming segment substantially corresponding to D1; D2$_p$: priming segment substantially corresponding to D1; D3$_p$: priming segment substantially corresponding to D1; AO1: first amplification oligonucleotide; AP[#]: amplification product.
Figure 5:
Figure 5:

In variations of the method utilizing multiple displacer tags, three or more displacer tags are employed, together with corresponding displacer priming oligonucleotide(s), to still further increase amplification capacity. FIG. 5 illustrates one such embodiment in which the first amplification oligomer from FIG. 3A further includes a third heterologous displacer tag D3 situated 5' to D2, with an optional third spacer segment S3 situated between D2 and D3. See FIG. 5, First Amp Oligo. Using this modified first oligomer in Steps 1 through 6 of FIG. 1A results in a second amplicon further comprising segment cD3, complementary to D3, located 3' to cD2. See FIG. 5, EP2. Referring to Step 1 of FIG. 5, in addition to hybridization of the third, fourth, and fifth amplification oligomers (comprising $T1_p$, and $D1_p$, and $D2_p$, respectively) to the second amplicon, an additional amplification oligomer comprising a third displacer priming segment $D3_p$, having a sequence substantially corresponding to D3, hybridizes to the second amplicon upstream from $D2_p$ to form a $D3_p$:cD3 duplex, and extension reactions are initiated from each of $T1_p$, $D1_p$, $D2_p$, and $D3_p$. See id., Step 1. Extension of the third amplification oligomer from $T1_p$ produces a third amplicon, which is displaced from the second amplicon template as the fourth amplification oligomer is extended from $D1_p$ to produce a fourth amplicon, which in turn is displaced as the fifth amplification oligomer is extended from $D2_p$ to produce a fifth amplicon, as previously depicted in Step 2 of FIG. 3A. Here, by inclusion of an additional cD3 priming site and a $D3_p$ priming oligomer, the fifth amplicon is similarly displaced from the template with extension from $D3_p$ to produce a tenth amplicon. Primer extension and displacement thus results in third, fourth, and fifth amplicons completely separated from the template strand, together with the production of an additional extension product, here designated as a tenth amplicon, AP10. See FIG. 5, Step 2. Upon separation of the tenth amplicon from the template strand, the tenth amplicon serves as a template for amplification from the second amplification oligomer comprising segment T2, thereby producing an eleventh amplicon comprising segments cT1, cD1, cD2, and $cD3_p$ (see Step 3), which can serve as a template for further amplification (e.g., using one or more of oligomers comprising $T1_p$, $D1_p$, $D2_p$, or $D3_p$).

Figure 4:
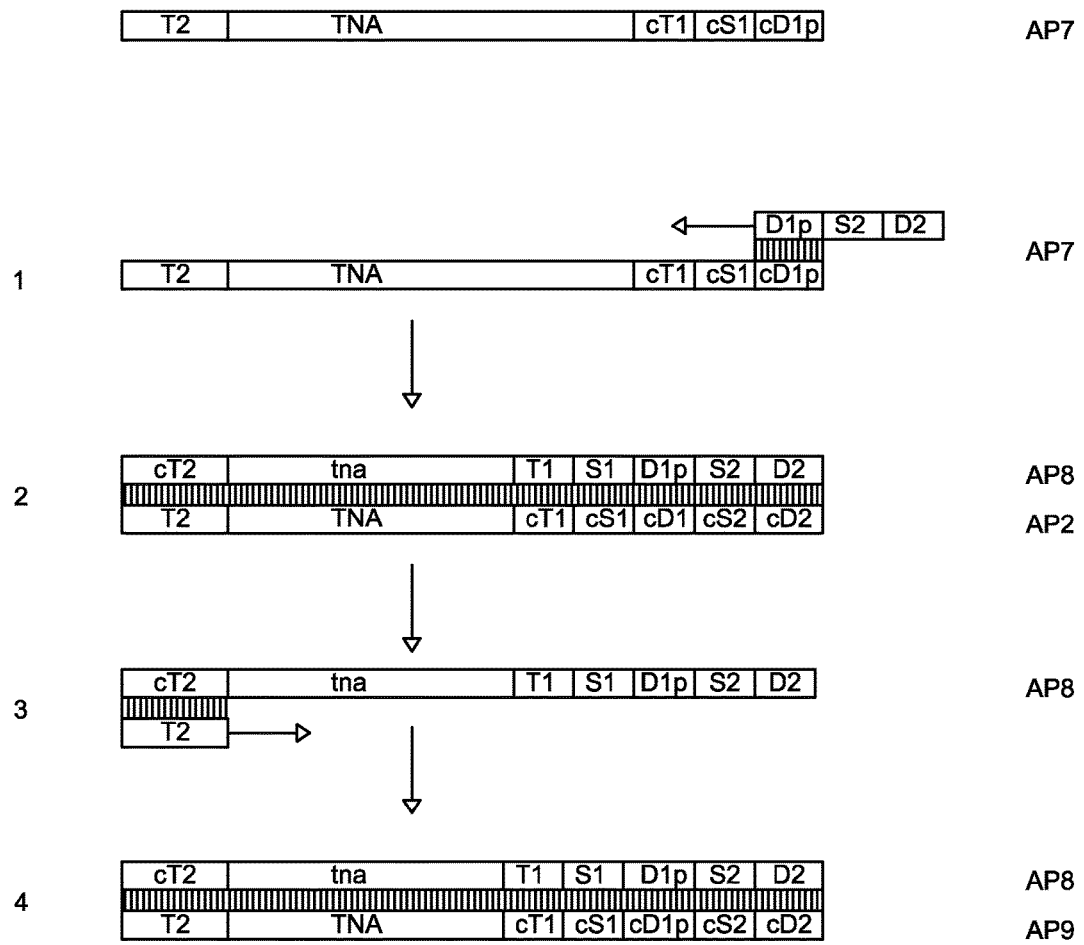
FIG. 4 depicts the use of an additional displacer oligonucleotide comprising a first displacer priming segment and a second heterologous displacer tag in the amplification reaction of FIGS. 3A and 3B. TNA: initial target nucleic acid or non-primer, amplicon portion thereof in +polarity; T1: target-binding priming segment; D1: first heterologous displacer tag segment; S1: first intervening spacer segment; D2: second heterologous displacer segment; S2: second intervening spacer segment; tna: non-primer, amplicon portion of target nucleic acid in –polarity; T2: priming segment substantially corresponding to 2nd amplicon; c[X]: amplicon regions complementary to segment [X]; D1$_p$: priming segment substantially corresponding to D1; D2$_p$: priming segment substantially corresponding to D1; AP[#]: amplification product.
Figure 6:
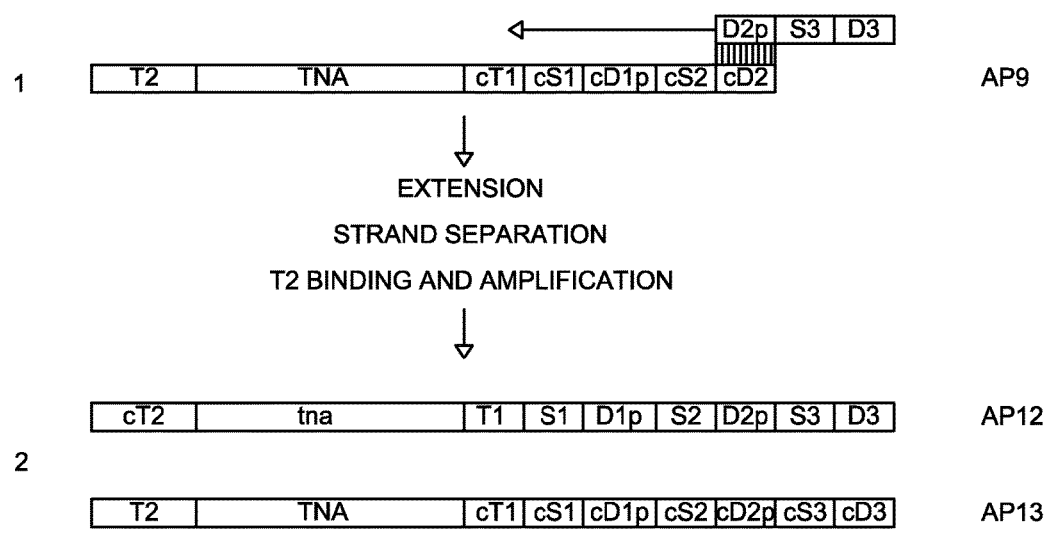
FIG. 6 depicts the use of an additional displacer oligonucleotide comprising a second displacer priming segment and a third heterologous displacer tag in the amplification reaction of FIGS. 3A and 3B. TNA: initial target nucleic acid or non-primer, amplicon portion thereof in +polarity; T1: target-binding priming segment; D1: first heterologous displacer tag segment; S1: first intervening spacer segment; D2: second heterologous displacer segment; S2: second intervening spacer segment; D3: third heterologous displacer segment; S3: third intervening spacer segment; tna: non-primer, amplicon portion of target nucleic acid in –polarity; T2: priming segment substantially corresponding to 2nd amplicon; c[X]: amplicon regions complementary to segment [X]; D1$_p$: priming segment substantially corresponding to D1; D2$_p$: priming segment substantially corresponding to D1; AP[#]: amplification product.

In other embodiments employing the use of three or more displacer tags, a third or further displacer tag(s) may be incorporated into an additional displacer oligonucleotide in a similar manner previously depicted in FIG. 4. In certain variations, for example, an amplification oligonucleotide comprising displacer priming segment $D2_p$ and a third displacer tag D3, situated 5' to $D2_p$, may be added to an amplification reaction as depicted in FIG. 4. Such an oligomer may be used, e.g., for further amplification of an amplicon comprising a second displacer priming site cD2 (or $cD2_p$) while also incorporating a third displacer priming site corresponding to D3. For example, referring to FIG. 6, AP9 represents a ninth amplicon comprising cD2, such as that produced by the amplification reaction depicted in FIG. 4. An amplification oligonucleotide comprising priming segment $D2_p$, an optional spacer segment S3, and displacer tag D3 hybridizes to the ninth amplicon to form a $cD2_p$:cD2 duplex. See FIG. 6, Step 1. Extension of the oligonucleotide produces a twelfth amplicon, which can bind the second amplification oligomer comprising target-binding segment T2 and serve as a template for amplification of a thirteenth amplicon comprising cD3 in addition to cT1, $cD1_p$, and $cD2_p$. See id., Step 2. This thirteenth amplicon may then be used as a template for, e.g., extension of a $D3_p$ displacer priming segment (in addition or alternatively to extension from $T1_p$, $D1_p$, and/or $D2_p$).

Figure 7:
FIG. 7 depicts the use of a reverse priming oligonucleotide comprising a displacer tag in the amplification reaction of FIGS. 1A and 1B. TNA: initial target nucleic acid or non-primer, amplicon portion thereof in +polarity; T1: target-binding priming segment; D1: first heterologous displacer tag segment; S1: first intervening spacer segment; D4: fourth heterologous displacer tag segment; S4: fourth intervening spacer segment; tna: non-primer, amplicon portion of target nucleic acid in –polarity; T2: priming segment substantially corresponding to 2nd amplicon; c[X]: amplicon regions complementary to segment [X]; T1$_p$: priming segment substantially corresponding to T1; D1$_p$: priming segment substantially corresponding to D1; D4$_p$: priming segment substantially corresponding to D4; AO2: second amplification oligonucleotide; AP[#]: amplification product.
Figure 7:

In various embodiments of the method, the tag-mediated displacement strategy as described herein may be employed using either a forward or reverse amplification oligonucleotide comprising one or more displacer tags. In other embodiments, both a forward and a reverse amplification oligonucleotide include one or more displacer tags. For example, in the amplification reaction previously depicted in FIGS. 1A and 1B, the second amplification oligomer comprising target-binding segment T2 may also include a heterologous displacer tag in addition to the first amplification oligomer. FIG. 7 illustrates such a variation, in which the second amplification oligomer comprises displacer tag D4 and an optional intervening spacer segment situated 5' to T2. See FIG. 7, Second Amp Oligo. Using this tagged T2 oligonucleotide in the reverse amplification reaction previously depicted in Steps 4 to 6 of FIG. 1A generates a second amplicon AP2 comprising D4 as shown in FIG. 7. Primer extension from the $D1_p$ displacer oligomer on this AP2 template (as previously depicted in Steps 7 to 9 of FIGS. 1A and 1B) then produces a fourth amplicon AP4 comprising a cD4 displacer priming site as shown in FIG. 7. Using this fourth amplicon as a template for further amplification, a amplification oligomer comprising priming segment $T2_p$, having a sequence substantially corresponding to T2, hybridizes to the second amplicon to form a $T2_p$:cT2 duplex, and a displacer oligonucleotide primer comprising a displacer priming segment $D4_p$, having a sequence substantially corresponding to D4, hybridizes to the fourth amplicon upstream from T2 to form a $D4_p$:cD4 duplex, and extension reactions are initiated from both $T2_p$ and $D4_p$. See FIG. 7, Step 1. Extension of the $T2_p$ amplification oligomer produces an extension product designated here as a fourteenth amplicon AP14, which is displaced from the AP2 template as the displacer oligomer is extended to produce an extension product designated here as a fifteenth amplicon AP 15. See id., Step 2.

Some preferred variations of the amplification method utilize an isothermal, transcription-based amplification reaction known as transcription-based amplification (TMA), various aspects of which are disclosed in Becker et al., U.S. Pat. No. 7,374,885. As previously discussed herein, TMA employs an RNA polymerase to produce multiple RNA copies of a target region. A promoter primer or promoter provider oligonucleotide is utilized to incorporate a promoter sequence for the RNA polymerase. Upon formation of a double-stranded promoter, produced by a primer extension reaction on the initial promoter sequence as a template, the RNA polymerase binds to the promoter and produces multiple RNA transcripts, which can become templates for further rounds of amplification in the presence of a priming oligonucleotide capable of hybridizing to the RNA transcripts.

Figure 8:
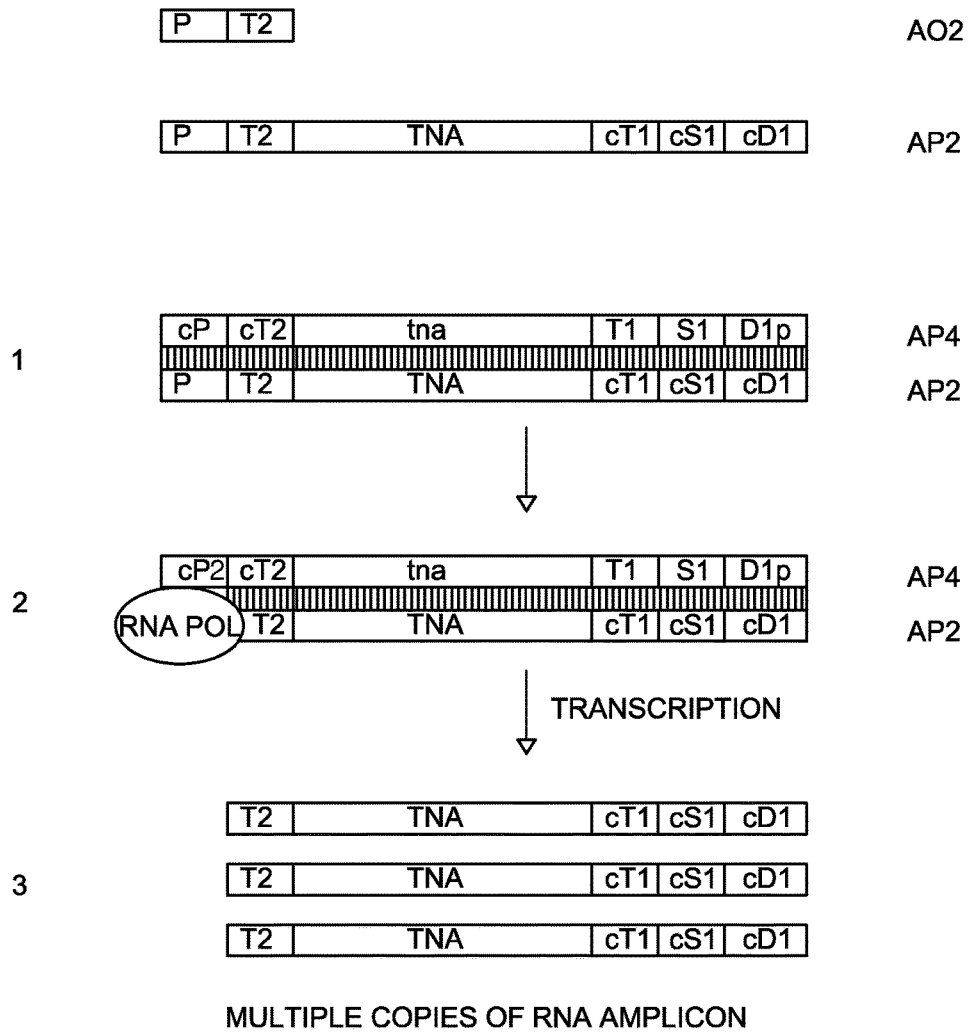
FIG. 8 depicts the use of a promoter primer in the amplification reaction of FIGS. 1A and 1B. TNA: initial target nucleic acid or non-primer, amplicon portion thereof in +polarity; T1: target-binding priming segment; D1: first heterologous displacer tag segment; S1: first intervening spacer segment; tna: non-primer, amplicon portion of target nucleic acid in –polarity; T2: priming segment substantially corresponding to 2nd amplicon; P: promoter segment; c[X]: amplicon regions complementary to segment [X]; D1$_p$: priming segment substantially corresponding to D1; AO2: second amplification oligonucleotide; AP[#]: amplification product; RNA POL: RNA polymerase.

Accordingly, particular variations of the present method include the use of a promoter primer in the amplification reaction. For example, in the amplification reaction previously depicted in FIGS. 1A and 1B, the second amplification oligomer comprising target-binding segment T2 may further include an RNA polymerase promoter sequence. FIG. 8 illustrates such a variation, in which the second amplification oligomer is a promoter primer comprising a priming segment T2 and a promoter sequence P situated 5' to T2. See FIG. 8, Second Amp Oligo. Using this promoter primer in the reverse amplification reaction previously depicted in Steps 4 to 6 of FIG. 1A generates a second amplicon AP2 comprising P as shown in FIG. 8. Primer extension from the $D1_p$ displacer oligomer on this AP2 template (as previously depicted in Steps 7 to 9 of FIGS. 1A and 1B) then produces a fourth amplicon AP4 comprising a segment cP complementary to the promoter sequence, thereby forming a double-stranded promoter region. See FIG. 8, Step 1. This fourth amplicon is used a template to transcribe multiple copies of an RNA amplicon complementary to the fourth amplicon, not including the promoter portion, using an RNA polymerase that recognizes the double-stranded promoter and initiates transcription therefrom. See FIG. 8, Steps 2 and 3. The resulting RNA amplicons comprise segments cT and $cD1_p$, complementary to the T1 and $D1_p$ priming sequences, and may thus be used as templates for further amplification using the third and fourth amplification oligomers comprising priming segments $T1_p$ and $D1_p$, respectively. Amplicons produced by extension from $T1_p$ or $D1_p$ on the RNA amplicon template may then serve as templates for further amplification upon hybridization of the second amplification oligomer via segment T2, formation of a double-stranded promoter, and RNA transcription as summarized above.

Figure 9:
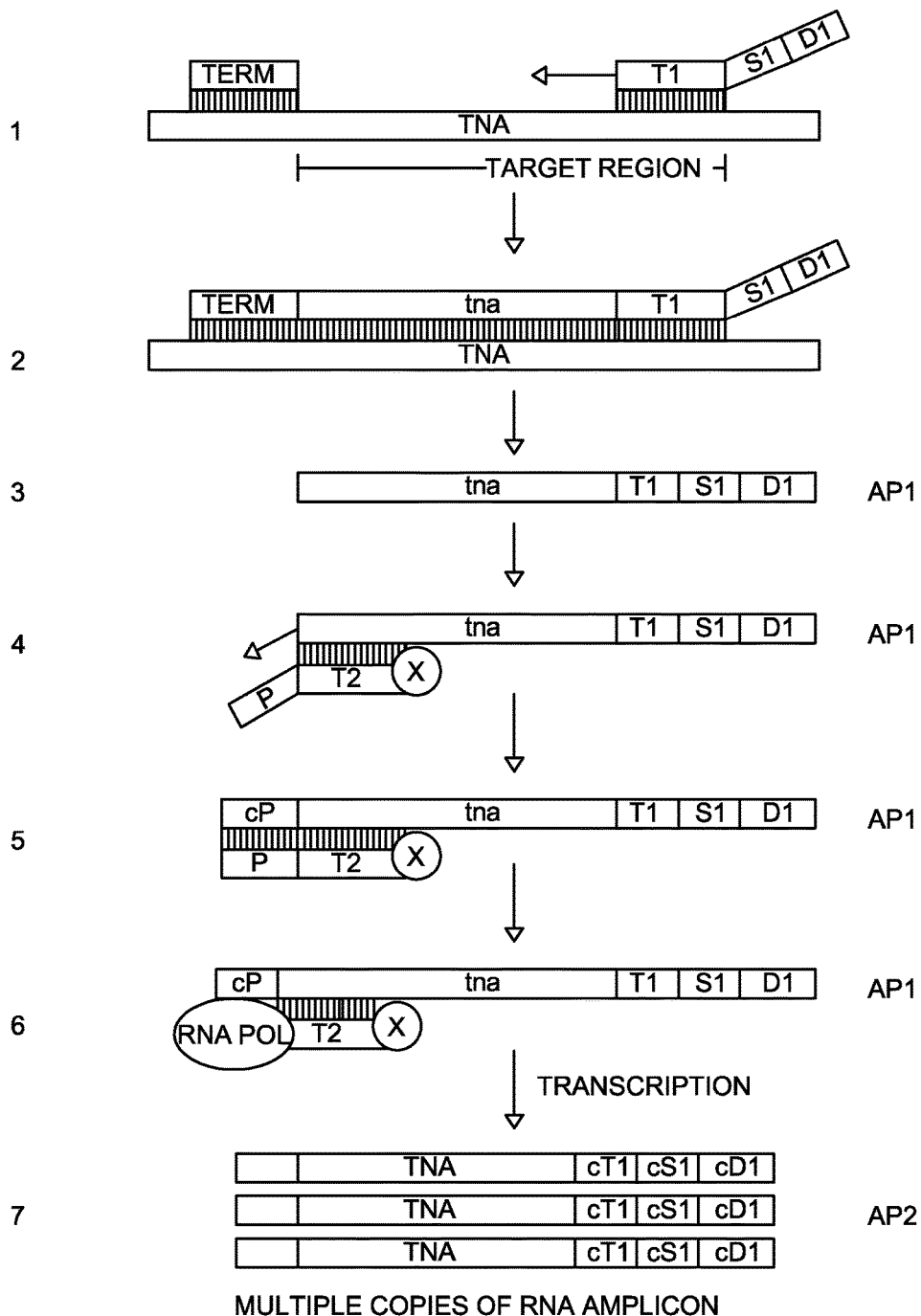
FIG. 9 depicts the use of a promoter provider in a tag-mediated displacement amplification reaction utilizing a first heterologous displacer tag. TNA: initial target nucleic acid or non-primer, amplicon portion thereof in +polarity; T1: target-binding priming segment; D1: first heterologous displacer tag segment; S1: first intervening spacer segment; tna: non-primer, amplicon portion of target nucleic acid in –polarity; TERM: terminating oligonucleotide; T2: target-binding segment substantially corresponding to 2nd amplicon; P: promoter segment; X: blocking moiety; c[X]: amplicon regions complementary to segment [X]; T1$_p$: priming segment substantially corresponding to T1; AP[#]: amplification product; RNA POL: RNA polymerase.

In other embodiments employing TMA, a promoter provider is used is used in the amplification reaction. FIG. 9 illustrates such a variation, in which the target nucleic acid is contacted with a termination oligonucleotide (TERM) in addition to a first amplification oligonucleotide comprising priming segment T1 and displacer tag D1. See FIG. 9, Step 1. The terminating oligonucleotide hybridizes to a target sequence that is adjacent to the 5'-end of the target region, such that extension of the first amplification oligomer (shown in FIG. 9 as comprising priming segment T1, displacer tag D1, and spacer S1) is terminated at the 3'-end of the terminating oligonucleotide, thereby providing a defined 3'-end for the first amplicon (AP1) that corresponds to the 5'-end of the target region. See id., Steps 1 and 2. The first amplicon is then separated from the target sequence (e.g., using an enzyme that selectively degrades that target sequence, such as, for example, RNAse H for an RNA target nucleic acid). See id., Step 3. The first amplicon is then contacted with a second amplification oligonucleotide comprising target-binding segment T2, substantially complementary to the defined 3'-end of the first amplicon, and a promoter sequence P situated 5' to T2. See id., Step 4. The second amplification oligomer is modified to prevent initiation of DNA synthesis, preferably by situating a blocking moiety (X) at the 3'-end of the oligonucleotide. See id. The T2 segment of the second amplification oligonucleotide hybridizes to the 3'-end of the first amplicon, and the 3'-end of the first amplicon is extended to add segment cP having a sequence complementary to the promoter sequence P, resulting in the formation of a double-stranded promoter sequence. See id., Steps 4 and 5. The first amplicon is used a template to transcribe multiple copies of a second amplicon AP2 complementary to the first amplicon, not including the promoter portion, using an RNA polymerase that recognizes the double-stranded promoter and initiates transcription therefrom. See id., Steps 6 and 7. As in the previous example depicted in FIG. 8, the resulting RNA amplicons comprise segments cT and cD1$_p$, complementary to the T1 and D1$_p$ priming sequences, and may thus be used as templates for further amplification using third and fourth amplification oligomers comprising priming segments T1$_p$ and D1$_p$, respectively. Amplicons produced by extension from T1$_p$ or D1$_p$ on the AP2 template may then serve as templates for further amplification upon hybridization of the second amplification oligomer via segment T2, formation of a double-stranded promoter, and RNA transcription.

In more particular variations of embodiments employing TMA, a promoter primer or promoter primer further includes one or more displacer tags situated 5' to a target-binding segment. In such embodiments, the one or more displacer tag(s) of a promoter primer or promoter primer are preferably situated 3' to the promoter sequence. In this manner, extension of the 3'-end of the template amplicon, upon hybridization of target-binding segment T2, produces a template comprising segments complementary to the displacer tag(s) and incorporation of the displacer tag(s) into the resulting RNA amplicon. Subsequent amplification of the RNA amplicon may then further include the use of displacer oligonucleotides to initiate displacement reactions in accordance with the present invention.

In some embodiments of the method, amplification of target region utilizes a target-specific priming site situated downstream from (5' to) a displacer priming site. For example, in particular variations utilizing a T1-D1 first amplification oligomer, a third amplification oligomer comprises a priming segment T1$_p$ having a nucleotide sequence substantially corresponding to T1 (and hence configured to hybridize to cT1, see, e.g., FIGS. 1A and 1B.) In alternative variations, a target-specific priming sequence substantially corresponds to the complement of a target sequence near or overlapping with the initial target sequence recognized by the target-binding segment of a displacer-tagged amplification oligomer. For example, in alternative variations of the amplification reaction depicted in FIGS. 1A and 1B, the third amplification oligomer T1$_p$ can be configured to hybridize to a target-specific sequence cT1' that is within the second amplicon AP2 and is different from cT1 (i.e., a sequence different from that corresponding to the initial target-specific priming site), wherein cT1' is situated within the target region 5' to cD1 and is near or overlapping with cT1. Similarly, e.g., in alternative variations of the amplification reaction depicted in FIG. 7, utilizing a displacer-tagged reverse amplification oligomer comprising a target-binding segment T2, an amplification oligomer T2$_p$ can be configured to hybridize to a target-specific sequence cT2' that is within the fourth amplicon AP4 and is different from cT2, wherein cT2' is near or overlapping with cT2 and is situated 5' to cD4. More preferably, the 3'-terminal base of the displacer oligonucleotide is spaced from 5 to 35 bases from the 5'-terminal base of the forward priming oligonucleotide. A target sequence is "near" a reference target sequence (e.g., near cT1 or cT2) if the 3'-end of the target sequence is within 50 bases, preferably within 40 bases, more preferably within 30 bases, and most preferably within 20, within 10, or within 5 bases of the 5'-end of the reference target sequence.

As previously discussed, certain variations of the method incorporate the use of universal priming sites and primers following initial amplification of a target nucleic acid. In such embodiments, an amplification oligomer comprising a target-specific hybridizing sequence (e.g., target-binding segment T1 of a first amplification oligonucleotide, or target-binding segment T2 of a second amplification oligonucleotide) includes a heterologous universal tag segment situated 5' to the target-specific segment T1. In this manner, subsequent rounds of amplification can employ the use of an amplification oligonucleotide comprising a universal priming segment (e.g., "U1$_p$") corresponding to the universal tag, in place of an oligonucleotide comprising a target-binding priming segment (e.g., "T1$_p$") specific for the target region of the target nucleic acid. In certain embodiments, both a forward and a reverse amplification oligomer (e.g., first and second amplification oligonucleotides as discussed herein) include a universal tag situated 5' to a target-binding segment. In particular embodiments employing a promoter primer or promoter primer for TMA, a universal tag is included 5' to the target-binding segment and 3' to the promoter sequence. Any variation of the methods discussed herein can be adapted for use with universal priming sites and primers following initial amplification of a target nucleic acid and such embodiments are within the scope of the present invention.

In each of the embodiments described herein, a wide variety of identities and functionalities can be designed into the displacer tag sequences. For example, in some embodiments, where two or more displacer sequences are used, at least two of these sequence can be different from each other. In other embodiments, at least two of the multiple displacer tags can be the same as each other. Similarly, in some variations where a universal priming sequence is used, one or more displacer tag sequence(s) is the same as the universal sequence; in other variations, one or more of the displacer tag sequence(s) are different from the universal sequence. Thus, in some embodiments, wherever two or more heterologous sequences (universal and displacer) are employed, there can be at least two unique sequences, or more depending on the number of displacer sequences added. In a more specific variation employing multiple displacer tags with a universal tag, each of the multiple displacer tags sequences are the same but different from the universal sequence.

In other more particular variations, sequences are designed to have different affinities for their complements. For example, in certain embodiments the affinity of a first displacer tag D1 for its complement is lower than that of a target-specific site T1 (or lower than that of a universal site U1 if a universal tag is used). Similarly, where multiple displacers are used, each successive displacer may be designed to have a lower affinity for its complement that the one situate 3' to it (e.g., D2 can be designed to have a lower affinity for its complement than D1; D3 can be designed to have a lower affinity for its complement than D2; etc.). In this way, the displacing potential of the oligonucleotide constructs can be increased by increasing, for example, the potential that a target-specific or universal priming site is available for binding before binding and extension of a D1 displacer oligomer (e.g., allowing a D1 displacer oligomer to bind to its priming site "after" binding of a target-specific or universal primer having a higher affinity), thereby maximizing the potential for binding and extension from both priming oligonucleotides together with a displacement reaction. The skilled artisan will appreciate that affinities of various displacer and universal sequences may be varied as desired based upon such known factors as, e.g., GC content and length of the hybridizing sequence.

Figure 10:
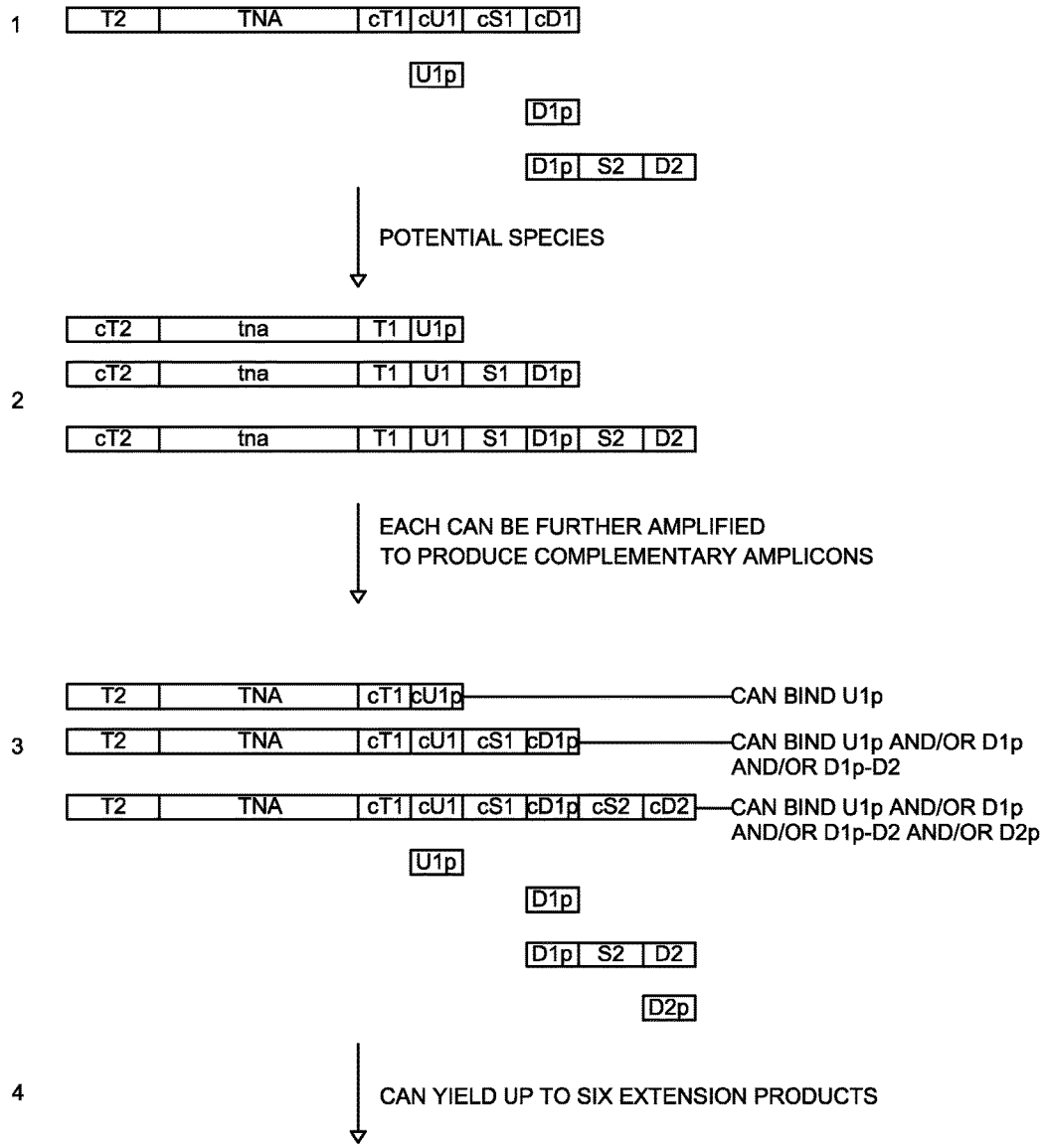
FIG. 10 depicts the amplification capacity of a tag-mediated displacement amplification reaction utilizing a universal priming site and a displacer priming site incorporated into an amplicon, together with three amplification oligomers: a universal priming oligomer, a displacer priming oligomer comprising a displacer priming segment; and a second displacer priming oligomer comprising the displacer priming segment and a heterologous displacer tag. TNA: initial target nucleic acid or non-primer, amplicon portion thereof in +polarity; T1: target-binding priming segment; U1: heterologous universal tag segment; D1: first heterologous displacer tag segment; S1: first intervening spacer segment; D2: second heterologous displacer segment; S2: second intervening spacer segment; tna: non-primer, amplicon portion of target nucleic acid in –polarity; T2: priming segment substantially corresponding to 2nd amplicon; c[X]: amplicon regions complementary to segment [X]; U1$_p$: priming segment substantially corresponding to U1; D1$_p$: priming segment substantially corresponding to D1; D2$_p$: priming segment substantially corresponding to D1; AP[#]: amplification product.

In addition to improving the kinetics of an amplification reaction via displacement of extension products from their template strands, tag-mediated displacement reactions can also increase amplification capacity. This advantage of the present invention is illustrated in FIG. 10, which shows a particular embodiment of a tag-mediated displacement strategy utilizing a universal priming site cU1 and a displacer priming site cD1 incorporated into an amplicon, together with three priming oligonucleotides—universal priming oligomer $U1_p$, substantially complementary to cU1; displacer priming oligonucleotide $D1_p$, substantially complementary to cD1; and a priming oligonucleotide comprising priming segment $D1_p$, optional spacer S2, and heterologous displacer tag D2 (the "$D1_p$-D2 oligomer"). See FIG. 10, Step 1. Extension reactions initiated from these three amplification oligomers yields up to three potential species as shown in Step 2. Each of these potential species can be further amplified in the next round to produce the three complementary amplicons as depicted in Step 3. In this example, in the next round of amplification, four amplification oligomers are depicted for use in further amplification: the $U1_p$ oligomer, the $D1_p$ oligomer, the $D1_p$-D2 oligomer, and a fourth oligomer which is a displacer priming oligonucleotide $D2_p$. In such a scenario, in the next amplification reaction, the first complementary amplicon can bind $U1_p$ to produce one amplicon; the second complementary amplicon can bind $U1_p$ together with $D1_p$ or $D1_p$-D2 to produce up to two amplicons; and the third complementary amplicon can bind $U1_p$ together with $D1_p$ and $D2_p$, or together with $D1_p$-D2, to yield up to three amplicons, thereby yielding up to six amplicons in the next round of the amplification reaction. See FIG. 10, Steps 3 and 4.

The methods of the present invention are useful in assays for detecting and/or quantitating specific target nucleic acids in clinical, water, environmental, industrial, beverage, food, seed stocks, and other samples or to produce large numbers of nucleic acid amplification products from a specific target sequence for a variety of uses. For example, the present invention is useful to screen clinical samples (e.g., blood, urine, feces, saliva, semen, or spinal fluid), food, water, laboratory and/or industrial samples for the presence of specific nucleic acids, specific organisms (e.g., using species-specific oligonucleotides) and/or specific classes of organisms (e.g., using class-specific oligonucleotides) in applications such as in sterility testing. The present invention can be used to detect the presence of, for example, viruses, bacteria, fungi, or parasites.

Samples suspected of containing a target nucleic acid are prepared for subsequent amplification as described herein using methods generally known in the art. Typically, a target nucleic acid is separated or purified from one or more other components of a sample. Such purification may include may include methods of separating and/or concentrating organisms contained in a sample from other sample components. In particular embodiments, purifying the target nucleic acid includes capturing the target nucleic acid to specifically or non-specifically separate the target nucleic acid from other sample components. Non-specific target capture methods may involve selective precipitation of nucleic acids from a substantially aqueous mixture, adherence of nucleic acids to a support that is washed to remove other sample components, or other means of physically separating nucleic acids from a mixture that contains target nucleic acid and other sample components.

In some embodiments, a target nucleic acid is selectively separated from other sample components by specifically hybridizing the target nucleic acid to a capture probe oligomer. The capture probe comprises a target-binding segment configured to specifically hybridize to a target sequence so as to form a target-nucleic-acid:capture-probe ("target:capture-probe") complex that is separated from sample components. In a preferred variation, the specific target capture further comprises binding the target:capture-probe complex to an immobilized probe to form a target:capture-probe:immobilized-probe complex that is separated from the sample and, optionally, washed to remove non-target sample components (see, e.g., U.S. Pat. Nos. 6,110,678; 6,280,952; and 6,534,273; each incorporated by reference herein). In such variations, the capture probe oligomer further comprises a sequence or moiety that binds attaches the capture probe, with its bound target-binding segment, to an immobilized probe attached to a solid support, thereby permitting the hybridized target nucleic acid to be separated from other sample components. In more specific embodiments, the capture probe oligomer includes a tail portion (e.g., a 3' tail) that is not complementary to the target nucleic acid but that specifically hybridizes to a nuclei acid sequence on the immobilized probe, thereby serving as the moiety allowing the target nucleic acid to be separated from other sample components, such as previously described in, e.g., U.S. Pat. No. 6,110,678, incorporated herein by reference. Any sequence may be used in a tail region, which is generally about 5 to 50 nt long, and preferred embodiments include a substantially homopolymeric tail of about 10 to 40 nt (e.g., $A_{10}$ to $A_{40}$), more preferably about 14 to 33 nt (e.g., $A_{14}$ to $A_{30}$ or $T_3A_{14}$ to $T_3A_{30}$), that bind to a complementary immobilized sequence (e.g., poly-T) attached to a solid support, e.g., a matrix or particle.

Target capture typically occurs in a solution phase mixture that contains one or more capture probes that hybridize specifically to the target nucleic acid under hybridizing conditions, usually at a temperature higher than the $T_m$ of the tail-sequence:immobilized-probe-sequence duplex. For embodiments comprising a capture probe tail, the target:capture-probe complex is captured by adjusting the hybridization conditions so that the capture probe tail hybridizes to the immobilized probe, and the entire complex on the solid support is then separated from other sample components. The support with the attached target:capture-probe:immobilized-probe may be washed one or more times to further remove other sample components. Certain embodiments use a particulate solid support, such as paramagnetic beads, so that particles with the attached target:capture-probe:immobilized-probe complex may be suspended in a washing solution and retrieved from the washing solution, preferably by using magnetic attraction. To limit the number of handling steps, the nucleic acid target region may be amplified by simply mixing the target nucleic acid in the complex on the support with amplification oligomers and proceeding with amplification steps.

For amplification of a target nucleic acid, a variety of nucleic acid amplification methods are known and may be readily adapted for use to incorporate a tag-mediated displacement strategy in accordance with the present invention (see above). Generally, certain amplification steps as described herein are "extension reactions" in which the 3'-end of a priming oligonucleotide is extended by the addition of nucleotides complementary to a nucleic acid template to which the priming oligonucleotide is hybridized, thereby synthesizing a complementary copy of the template. Conditions for extension reactions are well-known and generally utilize a polymerization agent (e.g., DNA polymerase) to synthesize the complementary DNA copy. A DNA polymerase may be characterized as "DNA-dependent" or "RNA-dependent," depending on whether the polymerase utilizes a DNA template or RNA template, respectively. Examples of DNA-dependent DNA polymerases are DNA polymerase I from *E. coli*, bacteriophage T7 DNA polymerase, or DNA polymerases from bacteriophages T4, Phi-29, M2, or T5. DNA-dependent DNA polymerases may be the naturally occurring enzymes isolated from bacteria or bacteriophages or expressed recombinantly, or may be modified or "evolved" forms which have been engineered to possess certain desirable characteristics, e.g., thermostability, or the ability to recognize or synthesize a DNA strand from various modified templates. It is known that under suitable conditions a DNA-dependent DNA polymerase may synthesize a complementary DNA copy from an RNA template. Alternatively, in some variations, an RNA-dependent DNA polymerase, or "reverse transcriptase" ("RT"), is utilized in a primer extension reaction. A reverse transcriptase synthesizes a complementary DNA copy from an RNA template. All known reverse transcriptases also have the ability to make a complementary DNA copy from a DNA template, and are thus both RNA- and DNA-dependent. RTs may also have an RNAse H activity.

Other amplification steps as described herein do not necessarily require an extension reaction. For example, certain amplification reactions may be catalyzed using a DNA-dependent RNA polymerase or "transcriptase," which synthesizes multiple RNA copies from a double-stranded or partially double-stranded DNA molecule having a promoter sequence that is usually double-stranded. The RNA molecules ("transcripts") are synthesized in the 5'-to-3' direction beginning at a specific position just downstream of the promoter. Examples of transcriptases are the DNA-dependent RNA polymerase from *E. coli* and bacteriophages T7, T3, and SP6. As previously discussed, in certain embodiments, a promoter region is introduced into an amplification reaction by the use of an amplification oligomer further comprising a promoter sequence situated 5' to a target-binding segment.

Certain embodiments of the present invention relate to amplification of a target nucleic acid utilizing transcription-mediated amplification (TMA). Some such embodiments relate more specifically to amplification of a target nucleic acid comprising an RNA target region. In certain cases, the target nucleic acid has indeterminate 3'- and 5'-ends relative to the desired RNA target region. The target nucleic acid is treated with a priming oligonucleotide which has a base region sufficiently complementary to a 3'-end of the RNA target region to hybridize therewith and, as discussed above, further comprises at least one heterologous displacer tag and optionally a universal tag in the first primer extension reaction. Priming oligonucleotides are designed to hybridize to a suitable region of any desired target sequence, according to primer design methods well-known to those of ordinary skill in the art. While the presence of the displacer tag sequence in a priming oligonucleotide may alter the binding characteristics of a target hybridizing region to a target nucleic acid sequence, the artisan skilled in the molecular arts can readily design priming oligonucleotides which contain both a target-binding segment and tag segments that can be used in accordance with the methods described herein. Additionally, the 5'-end of a priming oligonucleotide (preferably not a tagged priming oligonucleotide) may include one or modifications which improve the binding properties (e.g., hybridization or base stacking) of the priming oligonucleotide to a DNA extension product or to an RNA amplification product, provided the modifications do not substantially interfere with the priming function of the priming oligonucleotide or cleavage of an RNA amplification product to which the priming oligonucleotide is hybridized. The 3'-end of the priming oligonucleotide is extended by an appropriate DNA polymerase, e.g., an RNA-dependent DNA polymerase (reverse transcriptase) in an extension reaction using the RNA target region or amplification product as a template to give a DNA primer extension product which is complementary to the RNA template or amplification product.

DNA primer extension products may be separated (at least partially) from an RNA template using an enzyme which degrades the RNA template or amplification product. Suitable enzymes, i.e., "selective RNAses," are those which act on the RNA strand of an RNA:DNA complex, and include enzymes which comprise an RNAse H activity. Some reverse transcriptases include an RNAse H activity, including those derived from Moloney murine leukemia virus and avian myeloblastosis virus. According to preferred amplification embodiments, the selective RNAse may be provided as an RNAse H activity of a reverse transcriptase, or may be provided as a separate enzyme, e.g., as an *E. coli* RNAse H or a *T. thermophilus* RNAse H. Other enzymes which selectively degrade RNA present in an RNA:DNA duplex may also be used.

Following initial amplification of an RNA target region so as to incorporate one or more displacer tags into an amplification product, subsequent strand separation may be achieved using displacer oligonucleotides corresponding to the displacer tag sequences as described herein. For example, referring FIG. 9, which depicts the use of a promoter provider in transcription-mediated amplification of a target nucleic acid (which may be, e.g., an RNA target nucleic acid), multiple RNA amplicons (AP2) are produced comprising the complement of the D1 displacer tag (cD1) situated 5' to the complement of the T1 priming segment (cT1). See FIG. 9, Step 7. Subsequent amplification of an AP2 amplicon may utilize both $T1_p$ and $D1_p$ priming oligonucleotides substantially complementary to cT1 and cD1, respectively, such as previously illustrated, e.g., in FIGS. 1A and 1B. Briefly, referring to the further amplification of AP2 depicted in FIGS. 1A and 1B, in the presence of a DNA polymerase, the 3'-end of the $T1_p$ priming oligonucleotide is extended in a template-dependent manner to form a one extension product (a "third amplicon" or "AP3"), while the 3'-end of the $D1_p$ displacer oligonucleotide is also extended to form another extension product ("AP4") that displaces the AP3 extension product from the target nucleic acid (see Steps 7 to 9). In this manner, an extension product produced on an RNA amplicon template is made available for hybridization to an amplification oligomer for further amplification (e.g., hybridization to a promoter primer or promoter provider oligonucleotide) without the need for RNAse-mediated degradation of the RNA template.

When the initial target nucleic acid is DNA, then a first forward amplification oligomer can be a DNA primer comprising a 3' target-binding priming segment and a 5' first heterologous displacer tag. The first forward amplification oligomer can be used to make a first DNA primer extension product. When the amplification reaction is a PCR amplification reaction, then the first DNA primer extension product can be separated from the target nucleic acid by a number of methods, including using the temperature cycling parameters of a PCR reaction. Alternatively, and also for use with isothermal amplification reactions, the first DNA primer extension product can be separated from the from the target nucleic acid using a displacer primer comprising a target-specific priming segment that hybridizes to the DNA target nucleic acid at a position upstream from the forward priming oligonucleotide binding site (a first amplification oligomer such as described herein). In this manner, the first amplicon produced by extension of the first amplification oligomer can be displaced from the template strand by extension of the target-specific displacer primer, thereby making it available for hybridization to an amplification oligonucleotide (e.g., a promoter primer or promoter provider, or other amplification oligomer as described herein) for further amplification to produce a second amplicon. In a further alternative approach, conditions can be established whereby an oligonucleotide gains access to the first DNA primer extension product through strand invasion facilitated by, for example, DNA breathing (e.g., AT rich regions), low salt conditions, and/or the use of DMSO and/or osmolytes, such as betaine. A particularly suitable amplification oligomer for this embodiment is a promoter provider oligonucleotide such as that described herein, which is modified to prevent the promoter oligonucleotide from functioning as a priming oligonucleotide for a DNA polymerase (e.g., the promoter oligonucleotide includes a blocking moiety at its 3'-terminus). Irrespective of the method used to separate the first amplicon from a DNA template, once the first amplicon is made available to produce a second amplicon and with the use of heterologous displacer tags to incorporate heterologous displacer priming sites in amplicons as described herein, tag-mediated displacement can be utilized in subsequent amplification rounds to separate nucleic acid strands.

In certain embodiments, the methods of the present invention further comprise treating a target nucleic acid as described above to limit the length of a primer extension product to a certain desired length. Such length limitation is typically carried out through use of a "binding molecule" which hybridizes to or otherwise binds to the target nucleic acid adjacent to or near the 5'-end of the desired target sequence. In certain embodiments, a binding molecule comprises a base region. The base region may be DNA, RNA, a DNA:RNA chimeric molecule, or an analog thereof. Binding molecules comprising a base region may be modified in one or more ways, as described elsewhere herein. Suitable binding molecules include, but are not limited to, a binding molecule comprising a terminating oligonucleotide or a terminating protein that binds RNA and/or DNA and prevents primer extension past its binding region, or a binding molecule comprising a modifying molecule, for example, a modifying oligonucleotide such as a "digestion" oligonucleotide that directs hydrolysis of that portion of the RNA and/or DNA target hybridized to the digestion oligonucleotide, or a sequence-specific nuclease that cuts the RNA and/or DNA target.

Illustrative terminating oligonucleotides of the present invention have a 5'-base region sufficiently complementary to the target nucleic acid at a region adjacent to, near to, or overlapping with the 5'-end of the target sequence, to hybridize therewith. In certain embodiments, a terminating oligonucleotide is synthesized to include one or more modified nucleotides. For example, certain terminating oligonucleotides of the present invention comprise one or more 2'-O-ME ribonucleotides, or are synthesized entirely of 2'-O-ME ribonucleotides. See, e.g., Majlessi et al., *Nucleic Acids Res.*, 26, 2224-2229, 1998. A terminating oligonucleotide of the present invention typically also comprises a blocking moiety at its 3'-end to prevent the terminating oligonucleotide from functioning as a primer for a DNA polymerase. In some embodiments, the 5'-end of a terminating oligonucleotide of the present invention overlaps with and is complementary to at least about 2 nucleotides of the 5'-end of the target region. Typically, the 5'-end of a terminating oligonucleotide of the present invention overlaps with and is complementary to at least 3, 4, 5, 6, 7, or 8 nucleotides of the 5'-end of the target sequence, but no more than about 10 nucleotides of the 5'-end of the target region. (As used herein, the term "end" refers to a 5'- or 3'-region of an oligonucleotide, nucleic acid or nucleic acid region which includes, respectively, the 5'- or 3'-terminal base of the oligonucleotide, nucleic acid or nucleic acid region.)

In particular embodiment employing transcription-mediated amplification, a single-stranded DNA primer extension product, or "first" DNA primer extension product, which has either a defined 3'-end or an indeterminate 3'-end, is treated with a promoter oligonucleotide (a promoter primer or promoter provider) that comprises a target-binding segment substantially complementary to a 3'-region of the DNA primer extension product to hybridize therewith, and a second segment comprising a promoter for an RNA polymerase, e.g., T7 polymerase, which is situated 5' to the first segment (e.g., immediately 5' to or spaced from the first region). In some variations, the promoter oligonucleotide is a promoter provider modified to prevent the promoter oligonucleotide from functioning as a primer for a DNA polymerase (e.g., the promoter oligonucleotide includes a blocking moiety attached at its 3'-terminus). In particular variations, a promoter oligonucleotide further includes one or more heterologous displacer tags situated 5' to the target-binding segment and, most typically, 3' to the promoter region. In other embodiments, a promoter oligonucleotide includes a universal tag segment 5' to the target-binding segment and 3' to the promoter and any displacer tag(s). Upon identifying a desired target-binding segment and any desired displacer or universal tags, suitable promoter oligonucleotides can be constructed by one of ordinary skill in the art using only routine procedures. Those of ordinary skill in the art will readily understand that a promoter region has certain nucleotides which are required for recognition by a given RNA polymerase. In addition, certain nucleotide variations in a promoter sequence might improve the functioning of the promoter with a given enzyme, including the use of an intervening spacer segment between the promoter sequence and the target-binding segment (also referred to as an "insertion sequence"). Insertion sequences may be positioned between the target-binding and promoter segments of promoter oligonucleotides and function to increase amplification rates. (A displacer or universal tag segment of a tagged promoter oligonucleotide may provide this beneficial effect.)

Assaying promoter oligonucleotides with variations in the promoter sequences is easily carried out by the skilled artisan using routine methods. Furthermore, if it is desired to utilize a different RNA polymerase, the promoter sequence in the promoter oligonucleotide is easily substituted by a different promoter. Substituting different promoter sequences is well within the understanding and capabilities of those of ordinary skill in the art. For real-time TMA, promoter oligonucleotides provided to the amplification reaction mixture are modified to prevent efficient initiation of DNA synthesis from their 3'-termini, and preferably comprise a blocking moiety attached at their 3'-termini. Furthermore, terminating oligonucleotides and capping oligonucleotides, and even probes used in certain embodiments of the present invention also optionally comprise a blocking moiety attached at their 3'-termini.

Where a terminating oligonucleotide is used in a TMA reaction, the first, target-binding segment of a promoter oligonucleotide is designed to hybridize with a desired 3'-end of the first DNA primer extension product with substantial, but not necessarily exact, precision. Subsequently, the second segment of the promoter oligonucleotide may act as a template, allowing the first DNA primer extension product to be further extended to add a base region complementary to the second segment of the promoter oligonucleotide, i.e., the segment comprising the promoter sequence, rendering the promoter double-stranded. Alternatively, where a terminating oligonucleotide or other binding molecule is not used in a TMA reaction, a promoter primer may be used as the promoter oligonucleotide, thereby allowing the incorporation of a promoter sequence into a second extension product initiated from and thus comprising the promoter primer. In this case, priming of a third extension product using the second extension product as a template produces a double-stranded DNA that includes the double-stranded promoter. An RNA polymerase which recognizes the promoter then binds to the promoter sequence, and initiates transcription of multiple RNA copies complementary to the DNA primer extension product, which copies are substantially identical to the target region. By "substantially identical" it is meant that the multiple RNA copies may have additional nucleotides either 5' or 3' relative to the target sequence, or may have fewer nucleotides either 5' or 3' relative to the target sequence, depending on, e.g., the boundaries of the target region, the transcription initiation point, or whether the priming oligonucleotide comprises additional nucleotides 5' of the primer region. Where a target region is DNA, the sequence of the RNA copies is described herein as being "substantially identical" to the target region. It is to be understood, however, that an RNA sequence which has uridine residues in place of the thymidine residues of the DNA target region still has a "substantially identical" sequence. The RNA transcripts so produced may automatically recycle in the above system without further manipulation. Thus, this reaction is autocatalytic.

Promoters or promoter sequences suitable for incorporation in promoter oligonucleotides used in the methods of the present invention are nucleic acid sequences (either naturally occurring, produced synthetically or a product of a restriction digest) that are specifically recognized by an RNA polymerase that recognizes and binds to that sequence and initiates the process of transcription, whereby RNA transcripts are produced. Typical, known and useful promoters include those which are recognized by certain bacteriophage polymerases, such as those from bacteriophage T3, T7, and SP6, and a promoter from *E. coli*. The sequence may optionally include nucleotide bases extending beyond the actual recognition site for the RNA polymerase which may impart added stability or susceptibility to degradation processes or increased transcription efficiency. Promoter sequences for which there is a known and available polymerase that is capable of recognizing the initiation sequence are particularly suitable to be employed.

Suitable DNA polymerases for use in accordance with the methods of the invention, particularly for use with embodiments employing TMA, include reverse transcriptases. Particularly suitable DNA polymerases include AMV reverse transcriptase and MMLV reverse transcriptase. Some of the reverse transcriptases suitable for use in the methods of the present invention, such as AMV and MMLV reverse transcriptases, have an RNAse H activity. Indeed, according to certain embodiments of the present invention, the only selective RNAse activity in the amplification reaction is provided by the reverse transcriptase—no additional selective RNAse is added. However, in some situations it may also be useful to add an exogenous selective RNAse, such as *E. coli* RNAse H. Although the addition of an exogenous selective RNAse is not required, under certain conditions, the RNAse H activity present in, e.g., AMV reverse transcriptase may be inhibited or inactivated by other components present in the reaction mixture. In such situations, addition of an exogenous selective RNAse may be desirable. For example, where relatively large amounts of heterologous DNA are present in the reaction mixture, the native RNAse H activity of the AMV reverse transcriptase may be somewhat inhibited and thus the number of copies of the target sequence produced accordingly reduced. In situations where the target nucleic acid comprises only a small portion of the nucleic acid present (e.g., where the sample contains significant amounts of heterologous DNA and/or RNA), it is particularly useful to add an exogenous selective RNAse. See, e.g., Kacian et al, U.S. Pat. No. 5,399,491, incorporated by reference herein.

RNA amplification products produced by TMA methods may serve as templates to produce additional amplification products related to the target sequence through mechanisms described herein. The system is autocatalytic and amplification by the methods of the present invention occurs without the need for repeatedly modifying or changing reaction conditions such as temperature, pH, ionic strength and the like. These methods do not require an expensive thermal cycling apparatus, nor do they require several additions of enzymes or other reagents during the course of an amplification reaction.

The amplification product can be detected by any conventional means. For example, amplification product can be detected by hybridization with a detectably labeled probe and measurement of the resulting hybrids. Design criteria in selecting probes for detecting particular target sequences are well-known in the art and are described in, for example, Hogan et al., U.S. Pat. No. 6,150,517, incorporated by reference herein. Generally, probes should be designed to maximize homology for the target sequence(s) and minimize homology for possible non-target sequences. To minimize stability with non-target sequences, guanine and cytosine rich regions should be avoided, the probe should span as many destabilizing mismatches as possible, and the length of perfect complementarity to a non-target sequence should be minimized. Contrariwise, stability of the probe with the target sequence(s) should be maximized, adenine and thymine rich regions should be avoided, probe:target hybrids are preferably terminated with guanine and cytosine base pairs, extensive self-complementarity is generally to be avoided, and the melting temperature of probe:target hybrids should be about 2-10° C. higher than the assay temperature.

In a particular embodiment, the amplification product is assayed by the Hybridization Protection Assay ("HPA"), which involves hybridizing a chemiluminescent oligonucleotide probe (e.g., an acridinium ester-labeled ("AE") probe) to its target sequence, selectively hydrolyzing the chemiluminescent label present on unhybridized probe, and measuring the chemiluminescence produced from the remaining probe in a luminometer. See, e.g., Arnold et al., U.S. Pat. No. 5,283,174 and Norman C. Nelson et al., *Nonisotopic Probing, Blotting, and Sequencing*, Ch. 17 (Larry J. Kricka ed., 2d ed. 1995), each incorporated by reference herein.

In further embodiments, the present invention provides quantitative evaluation of the amplification process in real-time. Evaluation of an amplification process in "real-time" involves determining the amount of amplicon in the reaction mixture either continuously or periodically during the amplification reaction, and the determined values are used to calculate the amount of target sequence initially present in the sample. There are a variety of known methods for determining the amount of initial target sequence present in a sample based on real-time amplification. These include those disclosed by Wittwer et al., U.S. Pat. No. 6,303,305, and Yokoyama et al., U.S. Pat. No. 6,541,205, each incorporated by reference herein. Another method for determining the quantity of target sequence initially present in a sample, but which is not based on a real-time amplification, is disclosed by Ryder et al., U.S. Pat. No. 5,710,029, incorporated by reference herein.

Amplification products may be detected in real-time through the use of various self-hybridizing detection probes, most of which have a stem-loop structure. Such self-hybridizing probes are labeled so that they emit differently detectable signals, depending on whether the detection probes are in a self-hybridized state or an altered state through hybridization to a target sequence. By way of example, "molecular torches" are a type of self-hybridizing detection probe that includes distinct regions of self-complementarity (referred to as "the target binding domain" and "the target closing domain") that are connected by a joining region (e.g., non-nucleotide linker) and hybridize to each other under predetermined hybridization assay conditions. In a preferred embodiment, molecular torches contain single-stranded base regions in the target-binding domain that are from 1 to about 20 bases in length and are accessible for hybridization to a target sequence present in an amplification product under strand displacement conditions. Under strand displacement conditions, hybridization of the two complementary regions (which may be fully or partially complementary) of the molecular torch is favored, except in the presence of the target sequence, which will bind to the single-stranded region present in the target-binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed by Becker et al., U.S. Pat. No. 6,534,274, incorporated by reference herein.

Another example of a detection probe having self-complementarity is a "molecular beacon." Molecular beacons include nucleic acid molecules having a target complement sequence, an affinity pair (or nucleic acid arms) holding the probe in a closed conformation in the absence of a target sequence present in an amplification product, and a label pair that interacts when the probe is in a closed conformation. Hybridization of the target sequence and the target complement sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed by Tyagi et al., U.S. Pat. No. 5,925,517, and Tyagi et al., U.S. Pat. No. 6,150,097, each incorporated by reference herein.

Other self-hybridizing probes for use in the present invention are well-known to those of ordinary skill in the art. By way of example, probe binding pairs having interacting labels, such as those disclosed by Morrison, U.S. Pat. No. 5,928,862, and Gelfand et al., U.S. Pat. No. 5,804,375 for PCR reactions (each incorporated by reference herein), might be adapted for use in the present invention. Additional detection systems include "molecular switches," as disclosed by Arnold et al., U.S. Pat. Appln. Pub. No. US 2005-0042638 A1, incorporated by reference herein. And other probes, such as those comprising intercalating dyes and/or fluorochromes, might be useful for detection of amplification products in the present invention. See, e.g., Ishiguro et al., U.S. Pat. No. 5,814,447, incorporated by reference herein.

In those methods of the present invention where the initial target sequence and the RNA transcription product share the same sense, it may be desirable to initiate amplification before adding probe for real-time detection. Adding probe prior to initiating an amplification reaction may slow the rate of amplification since probe which binds to the initial target sequence has to be displaced or otherwise remove during the primer extension step to complete a primer extension product having the complement of the target sequence. The initiation of amplification is judged by the addition of amplification enzymes (e.g., a reverse transcriptase and an RNA polymerase).

Also provided by the subject invention is a reaction mixture for amplification of a target nucleic acid. A reaction mixture in accordance with the present invention at least comprises a combination of amplification oligomers as described herein for amplification of a nucleic acid target region. In certain embodiments, a reaction mixture also includes a capture probe for purifying the target nucleic acid and/or a detection probe for determining the presence or absence of an amplification product. The reaction mixture may further include a number of optional components such as, for example, arrays of capture probe nucleic acids. For an amplification reaction mixture, the reaction mixture will typically include other reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase), and will typically include test sample components, in which a target nucleic acid may or may not be present. In addition, for a reaction mixture that includes a detection probe together with an amplification oligomer combination, selection of amplification oligomers and detection probe oligomers for a reaction mixture are linked by a common target region (i.e., the reaction mixture will include a probe that binds to a sequence amplifiable by an amplification oligomer combination of the reaction mixture).

Also provided by the subject invention are kits for practicing the methods as described herein. A kit in accordance with the present invention at least comprises a combination of amplification oligomers as described herein for amplification of a nucleic acid target region. In certain embodiments, a reaction mixture also includes a capture probe for purifying the target nucleic acid and/or a detection probe for determining the presence or absence of an amplification product. The kits may further include a number of optional components such as, for example, arrays of capture probe nucleic acids. Other reagents that may be present in the kits include reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase). Oligomers as described herein may be packaged in a variety of different embodiments, and those skilled in the art will appreciate that the invention embraces many different kit configurations. For example, a kit may include amplification oligomers for only one target region, or it may include amplification oligomers for multiple target regions. In addition, for a kit that includes a detection probe together with an amplification oligomer combination, selection of amplification oligomers and detection probe oligomers for a kit are linked by a common target region (i.e., the kit will include a probe that binds to a sequence amplifiable by an amplification oligomer combination of the kit). In certain embodiments, the kit further includes a set of instructions for practicing methods in accordance with the present invention, where the instructions may be associated with a package insert and/or the packaging of the kit or the components thereof.

The invention is further illustrated by the following non-limiting examples.

Reagents

Various reagents are identified in the examples below, the formulations and pH values (where relevant) of these reagents were as follows.

A "Lysis Buffer" contains 15 mM sodium phosphate monobasic monohydrate, 15 mM sodium phosphate dibasic anhydrous, 1.0 mM EDTA disodium dihydrate, 1.0 mM EGTA free acid, and 110 mM lithium lauryl sulfate, pH 6.7.

A "Urine Lysis Buffer" contains 150 mM HEPES free acid, 294 mM lithium lauryl sulfate, 57 mM lithium hydroxide monohydrate, 100 mM ammonium sulfate, pH 7.5.

A "Target Capture Reagent" contains 250 mM HEPES free acid dihydrate, 310 mM lithium hydroxide monohydrate, 1.88 M lithium chloride, 100 mM EDTA free acid, 2 M lithium hydroxide to pH 6.4, and 250 µg/ml 1 micron magnetic particles Sera-Mag™ MG-CM Carboxylate Modified (Seradyn, Inc.; Indianapolis, Ind.; Cat. No. 24152105-050450) having oligo(dT)$_{14}$ covalently bound thereto.

A "Wash Solution" contains 10 mM HEPES free acid, 6.5 mM sodium hydroxide, 1 mM EDTA free acid, 0.3% (v/v) ethyl alcohol absolute, 0.02% (w/v) methyl paraben, 0.01% (w/v) propyl paraben, 150 mM sodium chloride, 0.1% (w/v) lauryl sulfate, sodium (SDS), and 4 M sodium hydroxide to pH 7.5.

An "Amplification Reagent" is a lyophilized form of a 3.6 mL solution containing 26.7 mM rATP, 5.0 mM rCTP, 33.3 mM rGTP and 5.0 mM rUTP, 125 mM HEPES free acid, 8% (w/v) trehalose dihydrate, 1.33 mM dATP, 1.33 mM dCTP, 1.33 mM dGTP, 1.33 mM dTTP, and 4 M sodium hydroxide to pH 7.5. The Amplification Reagent is reconstituted in 9.7 mL of "Amplification Reagent Reconstitution Solution" described below.

An "Amplification Reagent Reconstitution Solution" contains 0.4% (v/v) ethyl alcohol absolute, 0.10% (w/v) methyl paraben, 0.02% (w/v) propyl paraben, 33 mM KCl, 30.6 mM MgCl$_2$, 0.003% phenol red.

A "Primer Reagent" contains 1 mM EDTA disodium dihydrate, ACS, 10 mM Trizma7 base, and 6M hydrochloric acid to pH 7.5.

An "Enzyme Reagent" is a lyophilized form of a 1.45 mL solution containing 20 mM HEPES free acid dihydrate, 125 mM N-acetyl-L-cysteine, 0.1 mM EDTA disodium dihydrate, 0.2% (v/v) TRITON® X-100 detergent, 0.2 M trehalose dihydrate, 0.90 RTU/mL Moloney murine leukemia virus ("MMLV") reverse transcriptase, 0.20 U/mL T7 RNA polymerase, and 4M sodium hydroxide to pH 7.0. (One "unit" or "RTU" of activity is defined as the synthesis and release of 5.75 fmol cDNA in 15 minutes at 37° C. for MMLV reverse transcriptase, and for T7 RNA polymerase, one "unit" or "U" of activity is defined as the production of 5.0 fmol RNA transcript in 20 minutes at 37° C.) The Enzyme Reagent is reconstituted in 3.6 mL of "Enzyme Reagent Reconstitution Solution" described below.

An "Enzyme Reagent Reconstitution Solution" contains 50 mM HEPES free acid, 1 mM EDTA free acid, 10% (v/v) TRITON X-100 detergent, 120 mM potassium chloride, 20% (v/v) glycerol anhydrous, and 4 M sodium hydroxide to pH 7.0.

A "Probe Reagent" is a lyophilized form of a 3.6 mL solution containing 110 mM lithium lauryl sulfate, 10 mM of mercaptoethane sulfonic acid, 100 mM lithium succinate, and 3% PVP. The Probe Reagent is reconstituted in 36 mL of "Probe Reagent Reconstitution Solution" described below.

A "Probe Reagent Reconstitution Solution" contains 100 mM succinic acid, 73 mM lithium lauryl sulfate, 100 mM lithium hydroxide monohydrate, 15 mM aldrithiol, 1.2 M lithium chloride, 20 mM EDTA, 3% (v/v) ethyl alcohol, and 2M lithium hydroxide to pH 4.7.

A "Selection Reagent" contains 600 mM boric acid, ACS, 182.5 mM sodium hydroxide, ACS, 1% (v/v) TRITON X-100 detergent, and 4 M sodium hydroxide to pH 8.5.

A "Detection Reagents" comprises Detect Reagent I, which contains 1 mM nitric acid and 32 mM hydrogen peroxide, 30% (v/v), and Detect Reagent II, which contains 1.5 M sodium hydroxide.

An "Oil Reagent" is a silicone oil.

Example 1: S-Complex Preparation

S-Complexes were made in a reagent mixture made up of Target Capture Reagent (minus the magnetic particles), Lysis Buffer and water in a 1:2:2 ratio respectively. T7 oligonucleotide, non-T7 oligonucleotide, and S-Oligo were added to the reagent mixture at 6, 5, and 6 picomoles (pmol) per microliter (ul) respectively. The reagent mixture with the oligonucleotides was incubated at 95° C. for one minute in a hot block, followed by a 4° C. incubation for 5 minutes, followed by a room temperature incubation for approximately 20 minutes. The S-Complex (1 ul) was added to the Target Capture Reagent.

Example 2: Universal Tagged TMA with and without Displacer Oligonucleotides

In this example, several non-T7 amplification oligonucleotide variations, with and without displacer oligonucleotides were compared. The non-T7 sequence variations were (5' to 3'): displacer tag:spacer:tag:target specific (SEQ ID NO:6); tag:spacer:tag:target specific (SEQ ID NO:7); displacer tag: tag:target specific (SEQ ID NO:8); and tag:target specific (SEQ ID NO:9). A T7 promoter-based amplification oligomer (SEQ ID NO:11) was used with each of the 4 nonT7 amplification oligomers. The amplification oligomers (nonT7 and T7 pairs) were joined using the s-oligo SEQ ID NO:12 (see, e.g., Brentano et al. WO 2008/080029 describing reagents and methods for amplification using forward and reverse amplification oligomers joined with an s-oligo, incorporated herein by reference). The amplification oligonucleotide combinations were analyzed using target capture to extract target nucleic acid from a sample; single primer transcription mediated amplification (spTMA) to amplify the target nucleic acid; and molecular torches to detect the amplification product (i.e. amplicons) in "real-time" (i.e. continuous monitoring of fluorescent levels over time). Target Capture is described in Weisburg et al, U.S. Pat. No. 6,110,678 (the contents of which are incorporated by reference), spTMA is described in Becker et al., U.S. Pat. No. 7,374,885 and U.S. App. No. 20060046265A1 (the contents of which are incorporated by reference), and molecular torches are described in Becker et al, U.S. Pat. Nos. 6,849,412, 6,835,542, 6,534,274, and 6,361,945, US App. No. 20060068417A1; and Arnold et al. US App. No. US20060194240A1 (the contents of which are incorporated by reference). The protocols for each method are briefly described below.

The prostate specific antigen (PSA) gene was cloned and transected into competent cells. In vitro transcript (IVT) from the cloned PSA was used as the target nucleic acid. PSA IVT was spiked into a 1:1 mixture of Lysis Buffer and water at 0, 10.sup.2, and 10.sup.4 copies per 400 microliters (ul) and 400 ul of the spiked, diluted Lysis Buffer was transferred to a 96 deep well plate. Target Capture Reagent (100 ul) containing 5 pmol of SEQ ID NO:1, 1 ul of the S-Complex prepared according to Example 1 and using the combinations of nonT7, T7 and s-oligomer described directly above (see Table 1 for S-Complex primer combinations), and 2 pmol of SEQ ID NO:3 blocker was added to each well. The 96 well plate was sealed, a 90° C. heat block was placed on top of the plate, and the plate was vortexed on a low setting for 10 seconds. The 96 well plate was incubated at 60° C. for 25 and then cooled to room temperature for 25 minutes. The magnetic beads were pelleted using a KingFisher® instrument (Thermo Scientific) and the supernatant was removed. The magnetic beads were resuspended in 400 ul of Wash Solution, repelletted, and the wash solution was removed. Following capture and wash, the remaining complex was—a magnetic bead:immobilized probe:capture probe:target nucleic acid:s-oligo complex according to each of the combinations in Table 1. The magnetic beads were then resuspended in 60 ul of Amplification Reagent containing 10 pmol of SEQ ID NO:4, 15 pmol of each of SEQ ID NO:10, 10 pmol of SEQ ID NO:2 (labeled with ROX and FAM), and for half of the samples, 15 pmol of SEQ ID NO:5. The 96 well plate was placed in a Chromo4® instrument (Bio-Rad Laboratories, Inc., Hercules, Calif.) pre-warmed to 42° C. for 5 minutes. Enzyme Reagent (20 ul) was added to each well, the plate was briefly vortexed for 20 seconds, and returned to the Chromo4 instrument to start the fluorescence monitoring.

Four replicates were run for each assay condition. The results were measured by the amount of fluorescence over time. The reported Ct is the cycle time when the fluorescence level becomes higher than the background level. The results are summarized in Table 2, below and indicate that the use of tag-mediated displacer technology reduced the average Ct for each condition. That is, a fluorescent signal was detected earlier when using displacers than when not indicating that the amount of amplification product generated in a condition is greater when using the tag-mediated displacer than when not.

TABLE 1

| S-Oligomer Complexes | | |
|---|---|---|
| T7 SEQ ID NO: | Non-T7 SEQ ID NO: | S-oligo SEQ ID NO: |
| 11 | 6 | 12 |
| 11 | 7 | 12 |
| 11 | 8 | 12 |
| 11 | 9 | 12 |

TABLE 2

| Amt. of PSA IVT | S-Complex | Displacer | Ave. Ct (minutes) |
|---|---|---|---|
| 0 | 11, 6, 12 | No | No signal |
| 100 | 11, 6, 12 | No | 50 |
| 10,000 | 11, 6, 12 | No | 49.5 |
| 0 | 11, 6, 12 | Yes | No signal |
| 100 | 11, 6, 12 | Yes | 41.5 |
| 10,000 | 11, 6, 12 | Yes | 39 |
| 0 | 11, 7, 12 | No | No signal |
| 100 | 11, 7, 12 | No | 45 |
| 10,000 | 11, 7, 12 | No | 43 |
| 0 | 11, 7, 12 | Yes | No signal |
| 100 | 11, 7, 12 | Yes | 42.5 |
| 10,000 | 11, 7, 12 | Yes | 41 |
| 0 | 11, 8, 12 | No | No signal |
| 100 | 11, 8, 12 | No | 47 |
| 10,000 | 11, 8, 12 | No | 44 |
| 0 | 11, 8, 12 | Yes | No signal |
| 100 | 11, 8, 12 | Yes | 45 |
| 10,000 | 11, 8, 12 | Yes | 41 |
| 0 | 11, 9, 12 | No | No signal |
| 100 | 11, 9, 12 | No | 46.5 |
| 10,000 | 11, 9, 12 | No | 46 |

Example 3: Sensitivity of Universal Tagged TMA with and without Displacer Oligonucleotides In this example, the sensitivity of a non-T7 amplification oligonucleotide (SEQ ID NO:6, displacer:spacer:tag:target specific) with and without displacer oligonucleotides was evaluated. The procedures and oligonucleotide concentrations were the same as those described in Example 2 with the following changes. The PSA IVT was tested at 0, 100, 1000, 10000, 100000, and 1000000 copies per reaction. Four replicates were run for each assay condition. The results are summarized in Table 3, below and indicate that the use of displacers reduced the average Ct for a condition. Tag-mediated displacer technology increases the number of amplification products generated in a reaction to provide an earlier emergence of fluorescent signal.

TABLE 3

| Amt. of PSA IVT | Displacer | Ct (minutes) |
|---|---|---|
| 0 | No | No signal |
| 100 | No | 60 |
| 1000 | No | 56 |
| 10000 | No | 50 |
| 100000 | No | 46 |
| 1000000 | No | 39 |
| 0 | Yes | No signal |
| 100 | Yes | 52 |
| 1000 | Yes | 50 |
| 10000 | Yes | 43 |
| 100000 | Yes | 40 |
| 1000000 | Yes | 34 |

These examples show that tag-mediated displacement increased overall output and increased assay kinetics and sensitivity.

TABLE 4

| SEQ ID NO | Sequence 5' → 3' | Preferred Function |
|---|---|---|
| 1 | CGAACUUGCGCACACACGUCAUUGGAtttaaaaaaaaaaaaaaaaaaaaaaaaaaaaaaa | Target Capture |
| 2 | UGUGUCUUCAGGAUGAAACACACA | Torch |
| 3 | GAUGCAGUGGGCAGCUGUGAGGA | Blocker |
| 4 | aatttaatacgactcactatagggaga<u>*CCACAACGGTTT*</u> | T7 |
| 5 | *GAGGTCGTGGCTGGAGTCAT* | Displacer |
| 6 | *GAGGTCGTGGCTGGAGTCAT*atgtcaacgt<u>GTCATATGCG ACGATCTCAG</u>GCTGTGGCTGACCTGAAATACC | Non-T7 |
| 7 | <u>GTCATATGCGACGATCTCAG</u>atgtcaacgt<u>GTCATATGCG ACGATCTCAG</u>GCTGTGGCTGACCTGAAATACC | Non-T7 |
| 8 | *GAGGTCGTGGCTGGAGTCAT*<u>GTCATATGCGACGATCTCAG</u>GCTGTGGCTGACCTGAAATACC | Non-T7 |
| 9 | <u>GTCATATGCGACGATCTCAG</u>GCTGTGGCTGACCTGAAATACC | Non-T7 |
| 10 | <u>GTCATATGCGACGATCTCAG</u> | Non-T7 |
| 11 | aatttaatacgactcactatagggaga<u>*CCACAACGGTTTA*</u>CCCAGCAAGATCACGCTTTTG | T7 |
| 12 | <u>*AAACCGTTGTGG*</u>TCTCCCTATA<u>CTGAGATCGTCGCATATG AC</u> | s-oligo |

Table 4 illustrates oligonucleotide sequences such as those used in the examples. The legend for Table 4 is as follows. Bold=target specific; Italics=displacer tag; Underline=tag non-T7; Underline italics=tag T7; lowercase=promoter or capture tail.

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes.

What is claimed is:

1. A method of amplifying a nucleic acid target region, the method comprising:
   contacting a target nucleic acid comprising the target region with
   (1) a first amplification oligomer comprising
      (a) a target-binding priming segment (T1) complementary to a 3'-end of the target region;
      (b) a first heterologous displacer tag (D1) located 5' to T1; and
      (c) an intervening spacer segment (S1) between T1 and D1;
   said contacting comprising conditions whereby the target nucleic acid serves as a template for extension from the first amplification oligomer to produce a first amplification product comprising T1 and D1;
   (2) a second amplification oligomer comprising a target-binding segment T2 complementary to a region of the first amplicon that is the complement of a 5'-end of the target region, and wherein said contacting further comprises conditions whereby the first amplicon serves as a template to produce a second amplicon comprising segments cT1 and cD1, complementary to T1 and D1, respectively;
   (3) a third amplification oligomer comprising target-binding priming segment $T1_p$ having a nucleotide sequence complementary to T1, or complementary to the complement of a second amplicon target sequence cT1' near or overlapping with cT1 and situated 5' to cD1; and
   (4) a fourth amplification oligomer comprising a displacer priming segment $D1_p$ having a nucleotide sequence complementary to D1;
   wherein said contacting further comprises conditions whereby the second amplicon serves as a template for extension from both the third and fourth amplification oligomers, wherein extension of $T1_p$ from a $T1_p$:cT1/cT1' hybrid produces a third amplicon, and wherein extension of $D1_p$ from a $D1_p$:cD1 hybrid produces a fourth amplicon while displacing the third amplicon.

2. The method of claim 1, wherein the first amplification oligomer further comprises a second heterologous displacer tag (D2) located 5' to D1, whereby the first amplicon further comprises D2 and the second amplicon further comprises segment cD2, complementary to D2; and wherein the target nucleic acid is further contacted with
   (5) a fifth amplification oligomer comprising a second displacer priming segment $D2_p$ having a nucleotide sequence complementary to D2;
   wherein the contacting comprises conditions whereby
   (i) the second amplicon serves as a template for extension from the fifth amplification oligomer, wherein extension of $D2_p$ from a $D2_p$:cD2 hybrid produces a fifth amplicon comprising T1, D1, and $D2_p$; and
   (ii) the fifth amplicon serves as a template for amplification from the second amplification oligomer to produce a sixth amplicon comprising cT1, cD1, and $cD2_p$.

3. The method of claim 2, wherein the first amplification oligomer further comprises a second intervening spacer segment (S2) between D1 and D2.

4. The method of claim 1, wherein the target nucleic acid is further contacted with
   (5) a fifth amplification oligomer comprising (a) priming segment $D1_p$ and (b) displacer tag D2 located 5' to $D1_p$; and
   (6) a sixth amplification oligomer comprising a second displacer priming segment $D2_p$ having a nucleotide sequence complementary to D2;
   wherein the contacting comprises conditions whereby
   (i) the fourth amplicon serves as a template for amplification from the second amplification oligomer to produce a fifth amplicon comprising segments cT1 and $cD1_p$;
   (ii) at least one of the second and fifth amplicons serves as a template for extension from the fifth amplification oligomer, wherein extension of $D1_p$ from a $D1_p$:cD1 or $D1_p$:$cD1_p$ hybrid produces a sixth amplicon comprising T1, $D1_p$, and D2;
   (iii) the sixth amplicon serves as a template for amplification from the second amplification oligomer to produce a seventh amplicon comprising cT1, $cD1_p$, and cD2;
   (iv) the seventh amplicon serves as a template for extension from the sixth amplification oligomer, wherein extension of $D2_p$ from a $D2_p$:cD2 hybrid produces an eighth amplicon comprising T1, $D1_p$, and $D2_p$; and
   (v) the eighth amplicon serves as a template for amplification from the second amplification oligomer to produce a ninth amplicon comprising cT1, $cD1_p$, and $cD2_p$.

5. The method of claim 2, wherein the target nucleic acid is further contacted with
   (6) a sixth amplification oligomer comprising (a) priming segment $D1_p$ and (b) displacer tag D2 located 5' to $D1_p$;
   wherein the contacting comprises conditions whereby
   (i) the fourth amplicon serves as a template for amplification from the second amplification oligomer to produce a seventh amplicon comprising segments cT1 and $cD1_p$;
   (ii) at least one of the second, sixth, and seventh amplicons serves as a template for extension from the sixth amplification oligomer, wherein extension of $D1_p$ from a $D1_p$:cD1 or $D1_p$:$cD1_p$ hybrid produces an eighth amplicon comprising T1, $D1_p$, and D2; and
   (iii) the eighth amplicon serves as a template for amplification from the second amplification oligomer to produce a ninth amplicon comprising cT1, $cD1_p$, and cD2.

6. The method of claim 2,
   wherein the first amplification oligomer further comprises a third heterologous displacer tag (D3) located 5' to D2, whereby the first amplicon further comprises D3 and the second amplicon further comprises a segment cD3, complementary to D3; and wherein the target nucleic acid is further contacted with
   (7) a seventh oligonucleotide amplification oligomer comprising a third displacer priming segment $D3_p$ having a nucleotide sequence complementary to D3;
   wherein the contacting comprises conditions whereby
   (i) the second amplicon serves as a template for extension from the seventh amplification oligomer, wherein extension of $D3_p$ from a $D3_p$:cD3 hybrid produces a tenth amplicon comprising T1, D1, D2, and $D3_p$; and
   (ii) the tenth amplicon serves as a template for amplification from the second amplification oligomer to produce an eleventh amplicon comprising cT1, cD1, cD2, and $cD3_p$.

7. The method of claim 6, wherein the first amplification oligomer further comprises a third intervening spacer segment (S3) between D2 and D3.

8. The method of claim 4, wherein the target nucleic acid is further contacted with
   (7) a seventh amplification oligomer comprising (a) priming segment $D2_p$ and (b) displacer tag D3 located 5' to $D2_p$; and
   (8) an eighth oligonucleotide amplification oligomer comprising a third displacer priming segment $D3_p$ having a nucleotide sequence complementary to D3;
   wherein the contacting comprises conditions whereby
   (i) at least one of the seventh and ninth amplicons serves as a template for extension from the seventh amplification oligomer, wherein extension of $D2_p$ from a $D2_p$:cD2 or $D2_p$:$cD2_p$ hybrid produces a tenth amplicon comprising T1, $D1/D1_p$, $D2_p$, and D3;
   (ii) the tenth amplicon serves as a template for amplification from the second amplification oligomer to produce an eleventh amplicon comprising cT1, $cD1/cD1_p$, $cD2_p$, and cD3;
   (iii) the eleventh amplicon serves as a template for extension from the eighth amplification oligomer, wherein extension of $D3_p$ from a $D3_p$:cD3 hybrid produces a twelfth amplicon comprising T1, D1, D2, and $D3_p$; and
   (iv) the twelfth amplicon serves as a template for amplification from the second amplification oligomer to produce a thirteenth amplicon comprising cT1, cD1, cD2, and $cD3_p$.

9. The method of claim 5, wherein the target nucleic acid is further contacted with
   (8) an eighth amplification oligomer comprising (a) priming segment $D2_p$ and (b) displacer tag D3 located 5' to $D2_p$;
   wherein the contacting comprises conditions whereby
   (i) at least one of the second, sixth, ninth, and eleventh amplicons serves as a template for extension from the eighth amplification oligomer, wherein extension of $D2_p$ from a $D2_p$:cD2 or $D2_p$:$cD2_p$ hybrid produces a twelfth amplicon comprising T1, $D1/D1_p$, $D2_p$, and D3; and
   (ii) the twelfth amplicon serves as a template for amplification from the second amplification oligomer to produce a thirteenth amplicon comprising cT1, $cD1/cD1_p$, $cD2_p$, and cD3.

10. The method of claim 6, wherein the second amplification oligomer further comprises a fourth heterologous displacer tag (D4) located 5' to T2, whereby the second amplicon comprises T2 and D4; and whereby each of the third and fourth amplicons comprises segments cT2 and cD4, complementary to T2 and D4, respectively;
    wherein the target nucleic acid is further contacted with
    (9) a ninth amplification oligomer comprising a priming segment $T2_p$ having a nucleotide sequence complementary to T2, or complementary to the complement of a third or fourth amplicon target sequence cT2' near or overlapping with cT2 and situated 5' to cD4; and
    (10) a tenth amplification oligomer comprising a fourth displacer priming segment $D4_p$ having a nucleotide sequence complementary to D4; and
    wherein said contacting comprises conditions whereby at least one of the third and fourth amplicons serves as a template for extension from both the ninth and tenth amplification oligomers, wherein extension of $T2_p$ from a $T2_p$:cT2/cT2' hybrid produces a fourteenth amplicon, and wherein extension of $D4_p$ from a $D4_p$:cD4 hybrid produces a fifteenth amplicon while displacing the fourteenth amplicon.

11. The method of claim 10, wherein the second amplification oligomer further comprises a fourth intervening spacer segment (S4) between T2 and D4.

12. The method of claim 1, wherein the affinity of $D1_p$ for its complement is lower than that of T1.

13. The method of claim 2, wherein at least one of the following conditions is present:
    (a) the affinity of $D1_p$ for its complement is lower than that of T1;
    (b) the affinity of $D2_p$ for its complement is lower than that of $D1_p$.

14. A method of amplifying a nucleic acid target region, the method comprising:
    contacting a target nucleic acid comprising the target region with
    (1) a first amplification oligomer comprising a target-binding priming segment (T1) complementary to a 3'-end of the target region;
    said contacting comprising conditions whereby the target nucleic acid serves as a template for extension from the first amplification oligomer to produce a first amplicon;
    (2) a second amplification oligomer comprising
    (a) a target-binding segment T2 complementary to a region of the first amplicon that is the complement of a 5'-end of the target region;
    (b) a first heterologous displacer tag (D1) located 5' to T2; and (c) an intervening spacer segment (S1) between T2 and D1;

said contacting further comprising conditions whereby the first amplicon serves as a template for amplification from the second amplification oligomer to produce a second amplicon comprising T2 and D1; and whereby the second amplicon serves as a template for extension from the first amplification oligomer to produce a third amplicon comprising segments cT2 and cD1, complementary to T2 and D1, respectively;

(3) a third amplification oligomer comprising target-binding priming segment $T2_p$ having a nucleotide sequence complementary to T2, or complementary to the complement of a third amplicon target sequence cT2' near or overlapping with cT2 and situated 5' to cD1; and (4) a fourth amplification oligomer comprising a displacer priming segment $D1_p$ having a nucleotide sequence complementary to D1;

wherein said contacting further comprises conditions whereby the third amplicon serves as a template for extension from both the third and fourth amplification oligomers, wherein extension of $T2_p$ from a $T2_p$:cT2/cT2' hybrid produces a fourth amplicon, and wherein extension of $D1_p$ from a $D1_p$:cD1 hybrid produces a fifth amplicon while displacing the fourth amplicon.

15. The method of claim 14, wherein the second amplification oligomer further comprises a second heterologous displacer tag (D2) located 5' to D1, whereby the second amplicon further comprises D2 and the third amplicon further comprises segment cD2, complementary to D2; and wherein the target nucleic acid is further contacted with (5) a fifth amplification oligomer comprising a second displacer priming segment $D2_p$ having a nucleotide sequence complementary to D2;

wherein the contacting comprises conditions whereby (i) the third amplicon serves as a template for extension from the fifth amplification oligomer, wherein extension of $D2_p$ from a $D2_p$:cD2 hybrid produces a sixth amplicon comprising T2, D1, and $D2_p$; and (ii) the sixth amplicon serves as a template for extension from the first amplification oligomer to produce a seventh amplicon comprising cT2, cD1, and $cD2_p$.

16. The method of claim 15, wherein the second amplification oligomer further comprises a second intervening spacer segment (S2) between D1 and D2.

17. The method of claim 14, wherein the target nucleic acid is further contacted with (5) a fifth amplification oligomer comprising (a) priming segment $D1_p$ and (b) displacer tag D2 located 5' to $D1_p$; and (6) a sixth amplification oligomer comprising a second displacer priming segment $D2_p$ having a nucleotide sequence complementary to D2;

wherein the contacting comprises conditions whereby (i) the fifth amplicon serves as a template for extension from the first amplification oligomer to produce a sixth amplicon comprising segments cT2 and $cD1_p$;

(ii) at least one of the third and sixth amplicons serves as a template for extension from the fifth amplification oligomer, wherein extension of $D1_p$ from a $D1_p$:cD1 or $D1_p$:$cD1_p$ hybrid produces a seventh amplicon comprising T2, $D1_p$, and D2;

(iii) the seventh amplicon serves as a template for extension from the first amplification oligomer to produce an eighth amplicon comprising cT2, $cD1_p$, and cD2;

(iv) the eighth amplicon serves as a template for extension from the sixth amplification oligomer, wherein extension of $D2_p$ from a $D2_p$:cD2 hybrid produces a ninth amplicon comprising T2, D1, and $D2_p$; and (v) the ninth amplicon serves as a template for extension from the first amplification oligomer to produce a tenth amplicon comprising cT2, cD1, and $cD2_p$.

18. The method of claim 15, wherein the target nucleic acid is further contacted with (6) a sixth amplification oligomer comprising (a) priming segment $D1_p$ and (b) displacer tag D2 located 5' to $D1_p$;

wherein the contacting comprises conditions whereby (i) the fifth amplicon serves as a template for extension from the first amplification oligomer to produce an eighth amplicon comprising segments cT2 and $cD1_p$;

(ii) at least one of the third, seventh, and eighth amplicons serves as a template for extension from the sixth amplification oligomer, wherein extension of $D1_p$ from a $D1_p$:cD1 or $D1_p$:$cD1_p$ hybrid produces a ninth amplicon comprising T2, $D1_p$, and D2; and (iii) the ninth amplicon serves as a template for extension from the first amplification oligomer to produce a tenth amplicon comprising cT2, $cD1_p$, and cD2.

19. The method of claim 15, wherein the second amplification oligomer further comprises a third heterologous displacer tag (D3) located 5' to D2, whereby the second amplicon further comprises D3 and the third amplicon further comprises a segment cD3, complementary to D3; and wherein the target nucleic acid is further contacted with (7) a seventh amplification oligomer comprising a third displacer priming segment $D3_p$ having a nucleotide sequence complementary to D3;

wherein the contacting comprises conditions whereby (i) the third amplicon serves as a template for extension from the seventh amplification oligomer, wherein extension of $D3_p$ from a $D3_p$:cD3 hybrid produces an eleventh amplicon comprising T2, D1, D2, and $D3_p$; and (ii) the eleventh amplicon serves as a template for extension from the first amplification oligomer to produce a twelfth amplicon comprising cT2, cD1, cD2, and $cD3_p$.

20. The method of claim 19, wherein the second amplification oligomer further comprises a third intervening spacer segment (S3) between D2 and D3.

21. The method of claim 17, wherein the target nucleic acid is further contacted with (7) a seventh amplification oligomer comprising (a) priming segment $D2_p$ and (b) displacer tag D3 located 5' to $D2_p$; and (8) an eighth amplification oligomer comprising a third displacer priming segment $D3_p$ having a nucleotide sequence complementary to D3;

wherein the contacting comprises conditions whereby (i) at least one of the eighth and tenth amplicons serves as a template for extension from the seventh amplification oligomer, wherein extension of $D2_p$ from a $D2_p$:cD2 or $D2_p$:$cD2_p$ hybrid produces an eleventh amplicon comprising T2, D1/$D1_p$, $D2_p$, and D3;

(ii) the eleventh amplicon serves as a template for extension from the first amplification oligomer to produce a twelfth amplicon comprising cT2, cD1/$cD1_p$, $cD2_p$, and cD3;

(iii) the twelfth amplicon serves as a template for extension from the eighth amplification oligomer, wherein extension of $D3_p$ from a $D3_p$:cD3 hybrid produces an thirteenth amplicon comprising T2, D1, D2, and $D3_p$; and (iv) the thirteenth amplicon serves as a template for extension from the first amplification oligomer to produce a fourteenth amplicon comprising cT2, cD1, cD2, and $cD3_p$.

22. The method of claim 18, wherein the target nucleic acid is further contacted with (8) an eighth amplification oligomer comprising (a) priming segment $D2_p$ and (b) displacer tag D3 located 5' to $D2_p$;

wherein the contacting comprises conditions whereby (i) at least one of the third, seventh, tenth, and twelfth amplicons serves as a template for extension from the eighth amplification oligomer, wherein extension of $D2_p$ from a $D2_p$:cD2 or $D2_p$:$cD2_p$ hybrid produces a thirteenth amplicon comprising T2, D1/$D1_p$, $D2_p$, and D3; and (ii) the thirteenth amplicon serves as a template for extension from the first amplification oligomer to produce a fourteenth amplicon comprising cT2, cD1/$cD1_p$, $cD2_p$, and cD3.

23. The method of claim 14, wherein the affinity of $D1_p$ for its complement is lower than that of T1.

24. The method of claim 15, wherein at least one of the following conditions is present:

(a) the affinity of $D1_p$ for its complement is lower than that of T2;

(b) the affinity of $D2_p$ for its complement is lower than that of D1p.

25. A method of amplifying a nucleic acid target region, the method comprising:

(A) contacting a target nucleic acid comprising the target region with (1) a first amplification oligomer comprising
(a) a target-binding priming segment (T1) complementary to a 3'-end of the target region;
(b) a heterologous universal tag (U) located 5' to T1;
(c) a first heterologous displacer tag (D1) located 5' to U1; and
(d) an intervening spacer segment (S1) between U1 and D1;

said contacting comprising conditions whereby the target nucleic acid serves as a template for extension from the first amplification oligomer to produce a first amplicon comprising U1 and D1;

(2) a second amplification oligomer comprising
(a) a target-binding segment T2 complementary to a region of the first amplicon that is the complement of a 5'-end of the target region; and
(b) optionally, a heterologous universal tag (U2) located 5' to T2;

wherein said contacting further comprises conditions whereby the first amplicon serves as a template for amplification from the second amplification oligomer to produce a second amplicon comprising segments cU1 and cD1, complementary to U1 and D1, respectively, and optionally comprising U2;

(3) a third amplification oligomer comprising a universal priming segment $U1_n$ having a nucleotide sequence complementary to U1;

(4) a fourth amplification oligomer comprising a displacer priming segment $D1_p$ having a nucleotide sequence complementary to D1; and (5) if the second amplification oligomer comprises U2, a fifth amplification oligomer comprising a second universal priming segment $U2_p$ having a nucleotide sequence complementary to U2;

wherein said contacting further comprises conditions whereby the second amplicon serves as a template for extension from both the third and fourth amplification oligomers, wherein extension of $U1_p$ from a $U1_p$:cU1 hybrid produces a third amplicon, and wherein extension of $D1_p$ from a $D1_p$:cD1 hybrid produces a fourth amplicon while displacing the third amplicon;

or (B) contacting a target nucleic acid comprising the target region with (1) a first amplification oligomer comprising
(a) a target-binding priming segment (T1) complementary to a 3'-end of the target region; and
(b) optionally, a heterologous universal tag (U2) located 5' to T1;

said contacting comprising conditions whereby the target nucleic acid serves as a template for extension from the first amplification oligomer to produce a first amplicon;

(2) a second amplification oligomer comprising
(a) a target-binding segment T2 complementary to a region of the first amplicon that is the complement of a 5'-end of the target region;
(b) a heterologous universal tag (U1) located 5' to T2;
(c) a first heterologous displacer tag (D1) located 5' to U1;
(d) an intervening spacer segment (S1) between U1 and D1 said contacting further comprising conditions whereby the first amplicon serves as a template for amplification from the second amplification oligomer to produce a second amplicon comprising U1 and D1; and whereby the second amplicon serves as a template for extension from the first amplification oligomer to produce a third amplicon comprising segments cU1 and cD1, complementary to U1 and D1, respectively;

(3) a third amplification oligomer comprising a universal priming segment $U1_n$ having a nucleotide sequence complementary to U1;

(4) a fourth amplification oligomer comprising a displacer priming segment $D1_p$ having a nucleotide sequence complementary to D1; and (5) if the first amplification oligomer comprises U2, a fifth amplification oligomer comprising a second universal priming segment $U2_p$ having a nucleotide sequence complementary to U2;

wherein said contacting further comprises conditions whereby the third amplicon serves as a template for extension from both the third and fourth amplification oligomers, wherein extension of $U1_p$ from a $U1_p$:cU1 hybrid produces a fourth amplicon, and wherein extension of $D1_p$ from a $D1_p$:cD1 hybrid produces a fifth amplicon while displacing the fourth amplicon.

* * * * *